US008192782B2

(12) United States Patent
Søe et al.

(10) Patent No.: US 8,192,782 B2
(45) Date of Patent: Jun. 5, 2012

(54) ENZYMATIC OIL-DEGUMMING METHOD

(75) Inventors: Jorn Borch Søe, Tilst (DK); Mark Turner, Horshølm (DK)

(73) Assignee: Danisco A/S, Copenhagen (DK)

( * ) Notice: Subject to any disclaimer, the term of this patent is extended or adjusted under 35 U.S.C. 154(b) by 400 days.

(21) Appl. No.: 11/623,689

(22) Filed: Jan. 16, 2007

(65) Prior Publication Data

US 2007/0298157 A1    Dec. 27, 2007

Related U.S. Application Data

(63) Continuation-in-part of application No. PCT/GB2005/002823, filed on Jul. 18, 2005.

(60) Provisional application No. 60/591,185, filed on Jul. 26, 2004.

(30) Foreign Application Priority Data

Jul. 16, 2004  (GB) .................................. 0416035.4
Jul. 7, 2005   (GB) .................................. 0513859.9

(51) Int. Cl.
  A23D 7/00    (2006.01)
  C12N 9/00    (2006.01)
  C12N 9/10    (2006.01)
  C12N 15/00   (2006.01)
  C07H 21/04   (2006.01)
(52) U.S. Cl. ..... 426/601; 435/183; 435/193; 435/320.1; 536/23.2
(58) Field of Classification Search .................. None
  See application file for complete search history.

(56) References Cited

U.S. PATENT DOCUMENTS

| 2,888,385 A | 5/1959 | Grandel |
| 3,260,606 A | 7/1966 | Azuma |
| 3,368,903 A | 2/1968 | Johnson |
| 3,520,702 A | 7/1970 | Menzi |
| 3,634,195 A | 1/1972 | Melachouris |
| 3,652,397 A | 3/1972 | Pardun |
| 3,677,902 A | 7/1972 | Aunstrup |
| 3,817,837 A | 6/1974 | Rubenstein et al. |
| 3,850,752 A | 11/1974 | Schuurs et al. |
| 3,852,260 A | 12/1974 | Knutsen |
| 3,939,350 A | 2/1976 | Kronick et al. |
| 3,973,042 A | 8/1976 | Kosikowski |
| 3,996,345 A | 12/1976 | Ullman et al. |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,275,149 A | 6/1981 | Litman et al. |
| 4,277,437 A | 7/1981 | Maggio |
| 4,366,241 A | 12/1982 | Tom et al. |
| 4,399,218 A | 8/1983 | Gauhl |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,816,567 A | 3/1989 | Cabilly et al. |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |

(Continued)

FOREIGN PATENT DOCUMENTS

AR        331094        2/1995

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreij.
Acker, L. "Die Lipide des Getreides, ihre Zusammense und inre Bedeutung", Getreide Mehl Brot (1974) 28:181-187.
Adamzcak, Marek, et al., "Application of Enzymatic Glycerolysis for Production of Monoglycerides from Waste Fats", Polish Journal of Food and Nutrition Science, Mar. 1994.
Adhikari, B., et al., "Stickiness in Foods: A Review of Mechanisms and Test Methods", International Journal of Food Properties, vol. 4, No. 1, 2001.

(Continued)

*Primary Examiner* — Christian Fronda
(74) *Attorney, Agent, or Firm* — Vedder Price P.C.; Thomas J. Kowalski; Deborah L. Lu

(57) ABSTRACT

A process of enzymatic degumming edible oils, comprising treating edible oil with a lipid acyltransferase so as to transfer an acyl group from a major part of the phospholipid to one or more acyl acceptors, wherein the acyl acceptor may be any compound comprising a hydroxyl group. In one embodiment preferably the acyl acceptor is water and in another embodiment preferably the acyl acceptor is one or more sterols and/or stanols. When the acyl acceptor is a stanol and/or sterol, one or more sterol esters and/or stanol esters are produced. The lipid acyltransferase for use in the process of the present invention may comprise one or more of the following amino acid sequences: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, SEQ ID NO: 16, SEQ ID NO: 17, SEQ ID NO: 18, SEQ ID NO: 36, SEQ ID NO: 38, SEQ ID NO: 40, SEQ ID NO: 41, SEQ ID NO: 45, SEQ ID NO: 47, SEQ ID NO: 50 or an amino acid sequence which has 75% or more identity thereto. A novel lipid acyltransferase comprising the amino acid sequence shown as SEQ ID NO: 16 is also taught.

20 Claims, 37 Drawing Sheets

U.S. PATENT DOCUMENTS

| | | | |
|---|---|---|---|
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,310,679 A | 5/1994 | Artiss et al. |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,674,707 A | 10/1997 | Hintz et al. |
| 5,677,160 A | 10/1997 | Oester |
| 5,695,802 A | 12/1997 | Van Den Ouweland |
| 5,716,654 A | 2/1998 | Groenendaal |
| 5,741,665 A | 4/1998 | Kato et al. |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,824,354 A | 10/1998 | Ritter et al. |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,254,903 B1 | 7/2001 | Schuster et al. |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Soe et al. |
| 6,730,346 B2 | 5/2004 | Rey |
| 6,815,190 B1 | 11/2004 | Abo |
| 6,852,346 B2 | 2/2005 | Soe |
| 6,866,837 B2 | 3/2005 | Reubi et al. |
| 6,936,289 B2 | 8/2005 | Olsen et al. |
| 6,964,944 B1 | 11/2005 | Callisen et al. |
| 6,967,035 B2 | 11/2005 | Bojsen et al. |
| 7,226,771 B2 | 6/2007 | Gramatikova et al. |
| 7,718,204 B2 | 5/2010 | Soe et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2002/0182734 A1 | 12/2002 | Diaz-Torres |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0142441 A1 | 7/2004 | Weiss et al. |
| 2004/0235106 A1 | 11/2004 | Kapeller-Libermann |
| 2004/0235119 A1 | 11/2004 | Hoppe et al. |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell |
| 2006/0040357 A1 | 2/2006 | Bandaru et al. |
| 2006/0075518 A1 | 4/2006 | Yaver et al. |
| 2006/0141457 A1 | 6/2006 | Lindqvist et al. |
| 2007/0026106 A1 | 2/2007 | Kreij et al. |
| 2007/0122525 A1 | 5/2007 | Kreij |
| 2008/0063783 A1 | 3/2008 | Kreij et al. |
| 2008/0070287 A1 | 3/2008 | Soe et al. |
| 2008/0131936 A1 | 6/2008 | Miasnikov et al. |
| 2008/0187643 A1 | 8/2008 | Horlacher |

FOREIGN PATENT DOCUMENTS

| | | |
|---|---|---|
| AR | 249546 | 12/1996 |
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CA | 2403025 | 4/2004 |
| CN | 97181706.5 | 12/1997 |
| CN | 036151 | 2/2002 |
| CN | 172509 | 6/2003 |
| CN | 97181706.5 | 10/2003 |
| CN | 101200754 | 12/2007 |
| DE | 2817087 | 11/1978 |
| DE | 19620649 | 11/1997 |
| DE | 69129988 | 3/1999 |
| DE | 69330066 | 10/2001 |
| DE | 10018787 | 5/2002 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69551538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |

| | | | | | | |
|---|---|---|---|---|---|---|
| DK | PA1096/95 | 9/1995 | | EP | 1145637 | 10/2001 |
| DK | 152763 | 3/1998 | | EP | 0191217 | 2/2002 |
| DK | PA0543/98 | 4/1998 | | EP | 0869167 | 2/2002 |
| DK | PA199801572 | 11/1998 | | EP | 1193314 | 4/2002 |
| DK | PA5677000 | 12/1998 | | EP | 0746618 | 8/2002 |
| DK | PA199801604 | 12/1998 | | EP | 1233676 | 8/2002 |
| DK | PA199901736 | 12/1999 | | EP | 0648263 | 9/2002 |
| DK | PA200000989 | 6/2000 | | EP | 0784674 | 9/2002 |
| DK | PA200000991 | 6/2000 | | EP | 1073339 | 11/2002 |
| DK | PA200100285 | 2/2001 | | EP | 1275711 | 1/2003 |
| DK | PA200100843 | 5/2001 | | EP | 1285969 | 2/2003 |
| DK | EP659049 | 6/2001 | | EP | 1298205 | 4/2003 |
| DK | EP0784674 | 11/2002 | | EP | 0635053 | 6/2003 |
| DK | EP0869167 | 1/2003 | | EP | 0675944 | 6/2003 |
| DK | EP1073339 | 1/2003 | | EP | 0817838 | 6/2003 |
| DK | PA200300634 | 4/2003 | | EP | 1280919 | 6/2003 |
| DK | 5559215 | 7/2003 | | EP | 0746608 | 8/2003 |
| DK | EP0746608 | 10/2003 | | EP | 0851913 | 5/2004 |
| DK | EP1042458 | 3/2004 | | EP | 1262562 | 6/2004 |
| EP | 0064855 | 11/1982 | | EP | 1433852 | 6/2004 |
| EP | 0010296 | 12/1982 | | EP | 0977869 | 7/2004 |
| EP | 0109244 | 5/1984 | | EP | 0743017 | 9/2004 |
| EP | 0130064 | 1/1985 | | EP | 0675949 | 10/2004 |
| EP | 0140542 | 5/1985 | | EP | 0880590 | 10/2004 |
| EP | 0167309 | 1/1986 | | EP | 0897423 | 10/2004 |
| EP | 0171995 | 2/1986 | | EP | 1466980 | 10/2004 |
| EP | 0205208 | 12/1986 | | EP | 0839186 | 11/2004 |
| EP | 0206390 | 12/1986 | | EP | 1162889 | 2/2005 |
| EP | 0214761 | 3/1987 | | EP | 1532863 | 5/2005 |
| EP | 0257388 | 3/1988 | | EP | 1559788 | 8/2005 |
| EP | 0260573 | 3/1988 | | EP | 1363506 | 11/2005 |
| EP | 0334462 | 9/1989 | | EP | 1 624 047 A1 | 2/2006 |
| EP | 0195311 | 6/1990 | | EP | 01624047 A1 | 2/2006 |
| EP | 0375102 | 6/1990 | | EP | 1 624 047 B1 | 10/2006 |
| EP | 0426211 | 5/1991 | | EP | 1762622 | 3/2007 |
| EP | 0445692 | 9/1991 | | EP | 1 788 080 | 5/2007 |
| EP | 0449375 | 10/1991 | | EP | 1788080 | 5/2007 |
| EP | 0468731 | 1/1992 | | ES | 535608 | 9/1984 |
| EP | 0493045 | 7/1992 | | ES | 535602 | 10/1984 |
| EP | 0583265 | 10/1992 | | ES | 535609 | 3/1985 |
| EP | 0513709 | 11/1992 | | GB | 1086550 | 10/1967 |
| EP | 0542351 | 5/1993 | | GB | 1442418 | 7/1976 |
| EP | 0558112 | 9/1993 | | GB | 1577933 | 10/1980 |
| EP | 0258068 | 11/1993 | | GB | 2 264 429 | 9/1993 |
| EP | 0238023 | 12/1993 | | GB | 2264429 | 9/1993 |
| EP | 0575133 | 12/1993 | | GB | 0028701.1 | 11/2000 |
| EP | 0580252 | 1/1994 | | GB | 2358784 | 8/2001 |
| EP | 0258068 | 8/1994 | | GB | 0301117.8 | 1/2003 |
| EP | 0622446 | 11/1994 | | GB | 0301118.6 | 1/2003 |
| EP | 0652289 | 5/1995 | | GB | 0301119.4 | 1/2003 |
| EP | 0654527 | 5/1995 | | GB | 0301120.2 | 1/2003 |
| EP | 0396162 | 9/1995 | | GB | 0301121.0 | 1/2003 |
| EP | 0687414 | 12/1995 | | GB | 0301122.8 | 1/2003 |
| EP | 0585988 | 3/1996 | | GB | 2379165 | 3/2003 |
| EP | 0721981 | 7/1996 | | GB | 2267033 | 11/2003 |
| EP | 0752008 | 1/1997 | | GB | 0330016.7 | 12/2003 |
| EP | 0776604 | 6/1997 | | JP | 59183881 | 4/1960 |
| EP | 0531104 | 8/1997 | | JP | 480116612 | 5/1973 |
| EP | 0808903 | 11/1997 | | JP | 54-76892 | 6/1979 |
| EP | 0682116 | 12/1997 | | JP | 55131340 | 10/1980 |
| EP | 0812910 | 12/1997 | | JP | 57-189638 | 11/1982 |
| EP | 0305216 | 3/1998 | | JP | 57-189637 | 12/1982 |
| EP | 0847701 | 6/1998 | | JP | 60078529 | 5/1985 |
| EP | 0548228 | 8/1998 | | JP | 62118883 | 11/1985 |
| EP | 0866796 | 9/1998 | | JP | 63042691 | 8/1986 |
| EP | 0702712 | 12/1998 | | JP | 62061590 | 3/1987 |
| EP | 0882797 | 12/1998 | | JP | 62285749 | 12/1987 |
| EP | 0897667 | 2/1999 | | JP | 10203974 | 8/1988 |
| EP | 0913092 | 5/1999 | | JP | 1252294 | 10/1989 |
| EP | 0913468 | 5/1999 | | JP | 2-49593 | 2/1990 |
| EP | 0321811 | 12/1999 | | JP | 2-153997 | 6/1990 |
| EP | 1131416 | 6/2000 | | JP | 04075592 | 3/1992 |
| EP | 0739985 | 11/2000 | | JP | 6014773 | 3/1992 |
| EP | 1057415 | 12/2000 | | JP | 4121186 | 4/1992 |
| EP | 1071734 | 1/2001 | | JP | 15626492 | 6/1992 |
| EP | 0659049 | 3/2001 | | JP | 04200339 | 7/1992 |
| EP | 1103606 | 5/2001 | | JP | 4300839 | 10/1992 |
| EP | 1108360 | 6/2001 | | JP | 4327536 | 11/1992 |
| EP | 1138763 | 10/2001 | | JP | 04-370055 | 12/1992 |

| | | | | | |
|---|---|---|---|---|---|
| JP | 5211852 | 8/1993 | WO | 97/41736 | 11/1997 |
| JP | 6345800 | 12/1994 | WO | WO 98/00029 | 1/1998 |
| JP | 07-079687 | 3/1995 | WO | 98/08939 | 3/1998 |
| JP | 8268882 | 4/1995 | WO | 98/14594 | 4/1998 |
| JP | 7231788 | 9/1995 | WO | WO 98/13479 | 4/1998 |
| JP | 7330794 | 12/1995 | WO | WO 98/16112 | 4/1998 |
| JP | 8143457 | 6/1996 | WO | 98/18912 | 5/1998 |
| JP | 8266213 | 10/1996 | WO | 98/26057 | 6/1998 |
| JP | 9040689 | 2/1997 | WO | WO 98/23162 | 6/1998 |
| JP | 10155493 | 6/1998 | WO | 98/31790 | 7/1998 |
| JP | 10155493 A | 6/1998 | WO | WO 98/31790 | 7/1998 |
| JP | 11 228986 | 8/1999 | WO | 98/41623 | 9/1998 |
| JP | 11-228986 | 8/1999 | WO | 98/44804 | 10/1998 |
| JP | 11290078 | 10/1999 | WO | 98/45453 | 10/1998 |
| JP | 2000226335 | 8/2000 | WO | 98/50532 | 11/1998 |
| JP | 03/024096 | 7/2001 | WO | 98/51163 | 11/1998 |
| JP | 3553958 | 5/2004 | WO | 98/59028 | 12/1998 |
| KR | 93-700773 | 3/1993 | WO | 99/33964 | 7/1999 |
| KR | 94-10252 | 10/1994 | WO | 99/34011 | 7/1999 |
| KR | 95-700043 | 1/1995 | WO | 99/37782 | 7/1999 |
| KR | 95-702583 | 6/1995 | WO | 99/42566 | 8/1999 |
| KR | 96-704602 | 8/1996 | WO | 99/50399 | 10/1999 |
| KR | 2001-7012115 | 9/2001 | WO | 99/53001 | 10/1999 |
| KR | 2003-7008997 | 10/2003 | WO | 99/53769 | 10/1999 |
| NL | 0784674 | 12/2002 | WO | 99/55883 | 11/1999 |
| NL | 0869167 | 1/2003 | WO | 00/05396 | 2/2000 |
| NL | 1073339 | 2/2003 | WO | WO 00/23461 | 4/2000 |
| NL | 0746608 | 11/2003 | WO | 00/28044 | 5/2000 |
| PH | 31068 | 11/1984 | WO | 00/32758 | 6/2000 |
| RU | 2140751 | 6/1997 | WO | 00/34450 | 6/2000 |
| RU | 2235775 | 11/1999 | WO | 00/36114 | 6/2000 |
| RU | 2001117497 | 6/2001 | WO | 00/43036 | 7/2000 |
| SE | 9802548 | 7/1998 | WO | 00/49164 | 8/2000 |
| TR | 200101551 | 12/1999 | WO | 00/58517 | 10/2000 |
| WO | 88/02775 | 4/1988 | WO | 00/59307 | 10/2000 |
| WO | 88/03365 | 5/1988 | WO | 00/60063 | 10/2000 |
| WO | 8901969 | 3/1989 | WO | 00/61771 | 10/2000 |
| WO | 89/06803 | 7/1989 | WO | 00/71808 | 11/2000 |
| WO | 91/00920 | 1/1991 | WO | 00/75295 | 12/2000 |
| WO | 91/06661 | 5/1991 | WO | 01/16308 | 3/2001 |
| WO | 91/14772 | 10/1991 | WO | 01/27251 | 4/2001 |
| WO | WO 91/17243 | 11/1991 | WO | 01/29222 | 4/2001 |
| WO | 92/05249 | 4/1992 | WO | 01/34835 | 5/2001 |
| WO | 92/14830 | 9/1992 | WO | WO 01/39544 | 5/2001 |
| WO | 92/18645 | 10/1992 | WO | 01/39602 | 6/2001 |
| WO | 93/01285 | 1/1993 | WO | 01/42433 | 6/2001 |
| WO | 93/11249 | 6/1993 | WO | 01/47363 | 7/2001 |
| WO | 93/12812 | 7/1993 | WO | 01/66711 | 9/2001 |
| WO | 94/01541 | 1/1994 | WO | 01/78524 | 10/2001 |
| WO | 94/04035 | 3/1994 | WO | WO 01/75083 | 10/2001 |
| WO | 94/14940 | 7/1994 | WO | 01/83559 | 11/2001 |
| WO | 94/14951 | 7/1994 | WO | 01/83770 | 11/2001 |
| WO | 94/26883 | 11/1994 | WO | 01/92502 | 12/2001 |
| WO | 95/06720 | 3/1995 | WO | 02/00852 | 1/2002 |
| WO | 95/09909 | 4/1995 | WO | 02/03805 | 1/2002 |
| WO | 95/22606 | 8/1995 | WO | 02/06457 | 1/2002 |
| WO | 95/22615 | 8/1995 | WO | WO 02/06508 | 1/2002 |
| WO | 95/22625 | 8/1995 | WO | 02/14490 | 2/2002 |
| WO | 95/29996 | 11/1995 | WO | 02/24881 | 3/2002 |
| WO | 95/30744 | 11/1995 | WO | 02/30207 | 4/2002 |
| WO | 96/09772 | 4/1996 | WO | WO 02/39828 | 5/2002 |
| WO | 96/13578 | 5/1996 | WO | 02/055679 | 7/2002 |
| WO | 96/13579 | 5/1996 | WO | 02/062973 | 8/2002 |
| WO | 96/13580 | 5/1996 | WO | 02/065854 | 8/2002 |
| WO | 96/27002 | 9/1996 | WO | 02/066622 | 8/2002 |
| WO | 96/28542 | 9/1996 | WO | 02/094123 | 11/2002 |
| WO | 96/30502 | 10/1996 | WO | WO 0306644 | 1/2003 |
| WO | 96/32472 | 10/1996 | WO | 03/020923 | 3/2003 |
| WO | 96/39851 | 12/1996 | WO | WO 03/020923 | 3/2003 |
| WO | 97/04079 | 2/1997 | WO | WO 03/020941 | 3/2003 |
| WO | 97/05219 | 2/1997 | WO | WO 2006/031699 | 3/2003 |
| WO | 97/07202 | 2/1997 | WO | 03/040091 | 5/2003 |
| WO | 97/07205 | 2/1997 | WO | 03/060112 | 7/2003 |
| WO | 97/11083 | 3/1997 | WO | 03/070013 | 8/2003 |
| WO | 97/14713 | 4/1997 | WO | 03/089260 | 10/2003 |
| WO | 97/27237 | 7/1997 | WO | WO 03/089620 | 10/2003 |
| WO | 97/27276 | 7/1997 | WO | 03/097825 | 11/2003 |
| WO | 97/41212 | 11/1997 | WO | WO 03/097835 | 11/2003 |
| WO | 97/41735 | 11/1997 | WO | 03/099016 | 12/2003 |

| | | |
|---|---|---|
| WO | 03/100044 | 12/2003 |
| WO | 03/102118 | 12/2003 |
| WO | WO 03/100044 | 12/2003 |
| WO | 2004/004467 | 1/2004 |
| WO | 2004/018660 | 3/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | WO 2004/064537 | 8/2004 |
| WO | WO 2004/084638 | 10/2004 |
| WO | 2004/097012 | 11/2004 |
| WO | 2004/111216 | 12/2004 |
| WO | 2005/003339 | 1/2005 |
| WO | 2005/005977 | 1/2005 |
| WO | 2005/056782 | 6/2005 |
| WO | 2005/066347 | 7/2005 |
| WO | 2005/066351 | 7/2005 |
| WO | WO 2005069762 | 8/2005 |
| WO | 2005/080540 | 9/2005 |
| WO | 2005/087918 | 9/2005 |
| WO | WO 2005/111203 | 11/2005 |
| WO | 2006/008508 | 1/2006 |
| WO | 2006/008653 | 1/2006 |
| WO | WO 200618205 | 2/2006 |
| WO | 2006/032279 | 3/2006 |
| WO | WO 2006/045354 | 5/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

Agarwal et al., "Lipase Activity of Some Fungi Isolated from Groundnut", Current Science, Dec. 5, 1984, vol. 53, No. 23.
Aires-Barros et al (1994) Isolation and purification of lipases, Cambridge Unversity Press.
Aisaka, Kazuo et al., "Production of Lipoprotein Lipase and Lipase by Rhizopus japonicu", Agri. Biol. Chem., vol. 43, No. 10, pp. 2125-2129, 1979.
Akoh, Casimir C., et al., "GDSL family of serine esterases/lipases" Progress in Lipid Research, vol. 43, 2004, pp. 534-552.
Allan Svendsen et al., "Biochemical properties of cloned lipases from the Pseudomonas family", Biochimica et Biophysica Acta, vol. 1259, 1995, pp. 9-17.
Al-Obaidy, K A, Dissertation Abstracts International B (1987) vol. 47(9) 3597, order No. DA8624641, pp. 266.
Amano Enzyme Inc. (2004). Http://www.amano-enzyme.co.jp/english/productuse/oil_fat.html. Dato 21.06.04.
Amano Enzymes "Enzymes for Gastrointestinal Digestion" Oct. 1997.
Amano Enzymes, Amano Enzyme Europe Ltd, Sep. 1994.
Amin, Neelam S., et al., "Direct transformation of site-saturation libraries in *Bacillus subtilis*", BioTechniques, Dec. 2003, 35:1134-1140.
Amino acid composition of lipases.
Andersson, L., et al., "Hydrolysis of galactolipids by human pancreatic lipolytic enzymes and duidenal contents", Journal of Lipid Research, 1995, vol. 36, pp. 1392-1400.
Andreas Sander, Eberhand Eilers, Andrea Heilemann, Edith von Kreis.Fett/lipid 99 (1997) Nr. 4, 115-120.
Angelino, S.A.G.F., et al., "The first European Symposium on Enzymes and Grain Processing".
An-I Yeh et al., "Effects of Oxido-reductants on rheological properties of wheat flour dough and comparison with some characteristics of extruded noodles", Cereal Chemistry, 1999, vol. 76, No. 5, pp. 614-620.
Application of F. oxysporum phospholipase (FoL) in baking.

Arbige, Michael A et al, Novel lipase for cheddar cheese flavor development.
Archer, David B., et al., "Proteolytic degradation of heterologous proteins expressed in Aspergillus Niger", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 57(5).
Arpigny Jean Louis et al, "Bacterial lipolytic enzymes: Classification and properties", Biochemical Journal, vol. 343, No. 1, Oct. 1, 1999, pp. 177-183, XP002375631.
Assignment Document for Enzymatisk detergent additiv, detergent og vaskemetode.
Atomi, et al.; "Microbial Lipases—from Screening to Design"; pp. 49-51.
August C.A.P.A. et al. "The use of genetic engineering to obtain efficient production of porcine pancreatic phospholipase A2", Biochimica et Biophysica Acta, vol. 1089, 1991, pp. 345-351.
Aunstrup, Knud et al., "Production of Microbiol Enzymes", Microbiol Technology, vol. 1.
Ausubel, Frederick M., et al., "Short Protocols in Molecular Biology—A Compendium of Methods from Current Protocols in Molecular Biology", 1995, John Wiley & Sons, Inc.
Bachmatova, I., et al., "Lipase of Pseudomonas mendocina 3121-1 and its Substrate Specificty", Biologija, 1995.
Bailey's Industrial Oils and Fat Products, vol. 2, 4th Edition, John Wiley and Sons, New York pp. 97-173.
Bakezyme PH 800.
Balashev, Konstantin, Surface studies of enzymes using Atomic force microscopy (AFM).
Balcao V.M., Pavia A.L. Malcata F.X., Enzyme Microb Technhol, May 1, 1996; 18(6):392-416.
Balcao, Victor M and Malcata F. Xavier (1998), Biotechnology Advances, vol. 16, No. 2, pp. 309-341.
Ballance, D.J., et al., "Transformation of Aspergillus Nidulans by the orotidine-5'-phosphate decarboxylase gene of neurospora crassa", Biochemical and biophysical Research Communications, vol. 112, No. 1, 1983, pp. 284-289.
Ballance, Molecular Industrial Mycology, Systems and Applications for Filamentous Fungi, Leong and Berka (eds.), Marcel Dekker Inc, New York 1991, pp. 1-29.
Barbesgaard, Peder et al Applied Microbiology and Biotechnology (1992) 36: 569-572.
Barnes, P.J., "Lipids in Cereal Technology", Food and Science Technology, Academic Press, 1983.
Basrl, M., et al., "Amidination of Lipase with Hyrdophobic Imidoesters", JAOCS, vol. 69, No. 6, Jun. 1992.
Bateman A and Haft DH (2002) Brief Bioinform 3, 236-245.
Bateman A et al, (2002) Nucleic Acids Res. 30, 276-280.
Becker T. "Separation and Purification Processes for Recovery of Industrial Enzymes" in R.K. Singh, S.S.H. Rizvi (eds): Bioseparation processes in Foods, Marcel Dekker, New York, pp. 427-445.
Bedre Brod med nyt enzym.
Bekkers et al, The use of genetic engineering to obtain efficient production of porcine pancreatic phospholipase A2 by Saccharomyces cerevisiae, (1991) Biochim Biophys Acta 1089(3), 345-51.
Bengtsson Olivecrona Gunilla et al. Phospholipase activity of milk lipoprotein lipase, Methods in Enzymology, vol. 197, 1991.
Bentley S D et al, Complete genome sequence of the model actinomycete Streptomyces coelicolor A3(2), Nature vol. 417, 2002, pp. 141-147.
Berger K.G. (1990) Recent developments in palm oil. In Oleagineux 45:437-443.
Berks, Ben C., "A common export pathway for proteins binding complex redox cofactors?" Molecular Microbiology, 1996, vol. 22, pp. 393-404.
Beucage S.L. et al, (1981) Tetrahedron Letters 22, p. 1859-1869.
Bieleski R.L., Chapter 5, Sugar Alcohols.
Bilyk, Alexander, et al., "Lipase-catalyzed triglyceride Hydrolysis in Organic Solvent", pp. 320-323, JAOCS, vol. 68, No. 5, May 1991.
Biocatalysts, Limited, Product Sheet for Lipomod(TM) 627P-L627P.
Biotekkomet falder hardt til jorden.

Birch et al., "Evidence of Multiple Extracellular Phospholipase Activities of Aspergillus fumigatus", Infection and Immunity, Mar. 1996, vol. 64, No. 3, 1996.

Birgitte Hugh-Jensen et al., "Rhizomucor miehei Triglyceride Lipase is Processed and Secreted from Transformed Aspergillus oryzae", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.

Bjorkling, F., et al., "Lipase Catalyzed Organic Synthesis", S. Servie (ed.), Microbial Reagents in Organic Synthesis, pp. 249-260, 1992.

Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.

Bjorkling, Frederik, et al., "Lipase -mediated Formation of Peroxycarboxylic acids used in Catalytic Epoxidation of Alkenes", J. Chem. Soc., Chemical Communications, Issue 19, 1990.

Bjurlin et al. Identification of carboxylesterase activities of commercial triacylglycerol hydrolase (lipase) preparations, Eur. J. Lipid Sci. Technol. 104 (2002) 143-155.

Blain JA et al, The Nature of Mycelial Lipolytic enzymes in filamentous fungi, Fems Microbiol. Lett., 1978, vol. 3, 85-87.

Blecker et al, Improved emulsifying and foaming of whey proteins after enzymic fat hydrolysis, (1997) J Food Science, vol. 62, No. 1.

Blumenthal, Cynthia Z., "Production of toxic metabolites in Aspergillus niger, Aspergillus oryzae, and Trichoderma reesei: justification of mycotoxin testing in food grade enzyme preparations derived from the three fungi", Regulatory Toxicology and Pharmacology, vol. 39, 2004, p. 214-228.

Boel, Esper, et al.; "Rhizomucor miehei Triglyceride Lipase is Synthesized as a Precursor"; Novo Research Institute; vol. 23; No. 7; Jul. 1988.

Bornscheuer U T et al, Trends in Biotechnology, Elsevier Publications, Cambridge GB, vol. 20, No. 10, Oct. 1, 2002, pp. 433-437.

Bornscheuer, Uwe T., Lipase-catalyzed syntheses of monoacylglycerols, Enzyme and Microbiol Technology, vol. 17, pp. 578-586, 1995.

Brady, Leo, et al., "A serine protease triad forms the catalytic centre of a triacylglycerol lipase", Nature, vol. 343, 1990.

Brockerhoff, Hans, et al., "Lipolytic Enzymes", Academic Press, 1974.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor comples", Nature, vol. 351, 1991.

Buckley J. Thomas et al, Journal of Biological Chemistry, vol. 257, No. 6, pp. 3320-3325, 1982.

Buckley, Biochemistry 1983, 22, 5490-5493.

Bulkacz J et al, Biochim. Biophys. Acta (1981) vol. 664, pp. 148-155.

Bulletin of the IDF 294: 1994.

Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.

Butcher, Bronwyn G., et al., Microbiology, 2002, vol. 148, pp. 3983-3992.

Buxton et al, Gene, 1985, 37:207-214.

Cao, Shu-Gui, et al., "Enzymatic Preparation of Monoglycerides via Glycerolysis of Fats and Oils Catalyzed by Lipase from Pseudomonas Species" National Laboratory of Enzyme Engineering.

Carriere et al, "Pancreatic Lipase Structure- Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) Nuc Acids Res Symp Ser 215-23.

Casimir C A et al Progress in Lipid Research, 2004, pp. 534-552.

Castello, P., et al., "Technological and Biochemical effects of exogenous lipases in breadmaking", 2nd European Symposium on enzymes in Grain Processing.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.

Chakravarti DN et al, Biol. Abstracts, 1981, vol. 72, abstract No. 012592.

Cheng Cheng et al., "Transformation of Trichoderma viride using the Neurospora crassa pyr4 gene and its use in the expression of a Taka-amylase a gene from Aspergillus oryzae", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from Arabidopsis", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science and Technology, vol. 103, 2001, pp. 333-340.

Clausen, Kim, "New enzyme for degumming", Oils and Fats International, vol. 17, No. 4, Jun. 2001, pp. 24-25.

Cloning of rad51 and rad52 homologues from Aspergillus oryzae and the effect of their overexpression on homologous recombination.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988 (89/107/EEC).

Council Regulation (EC) No. 2991/94 5/12/94 Official Journal of the European Communities, Sep. 12, 1994, No. L316/2-7.

Courtin, Christophe M., et al., "Recent Advances in Enzymes in Grain Processing".

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.
Daboussi et al, Heterologous expression of the Aspergillus nidulans regulatory gene nirA in Fusarium oxysporum, (1991) Gene 109(1), 155-60.
Daboussi et al., "Transformation of seven species of filamentous fungi using the nitrate reductase gene of Aspergillus nidulans", Curr. Genet., 15:453-456, 1989.
Daftary, R.D., et al., "Functional Bread-Making Properties of Wheat Flour Lipids", Food Technology, vol. 22, No. 237, Mar. 1968-1979.
Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.
Dalrymple, Brian D., et al., "Three Neocallimastic patriciarum esterases associated with the degradation of complex polysaccharides are members of a new family of hydrolases", Microbiology, vol. 142, pp. 2605-2614, 1997.
Danisco, "Unique Chance for Better Bread" *Direct, A Newsletter from Danisco Ingredients* (1996).
Danisco, Hexose oxidase—nyt enzym med mange mulingheder (advert).
Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.
Database accession No. P10480 -& Database UniProt 'Online!, Jul. 1, 1989.
Database accession No. Q44268 -& Database UniProt 'Online! Nov. 1, 1996.
Database accession No. Q9F7Y6 Database UniProt 'Online!, Mar. 1, 2001.
Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.
Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.
Database FSTA International Food Information Service (IFIS), Frankfurt/Main, DE Qi Si J: "New enzymes for the baking industry" XP002077284 see abstract & Food Tech Europe vol. 3, No. 1, 1996, pp. 60-64, Novo Nordisk Ferment Ltd.
Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.
Database UNIPROTKB Jun. 1, 2003, S. Omura et al: "putative secreted hydrolase from streptomyces avermitilis" XP002376340 retrieved from EBI, Hinxton, UK Database accession No. Q828T4 abstract.
Database UNIPROTKB May 1, 2000, S.D. Bentley et al: "Putative Secreted Hydrolase from Streptomyces coelicolor" XP002376339 retrieved from EBI, Hinxton, UK Database accession No. Q9S2A5 abstract.
Davies, Progress in Industrial Microbiology, Martinelli and Kinghorn (eds.), Elsevier, Amsterdam 1994, 29:525-560.
De Haas GH et al, "Purification and Properties of Phospholipase A from Porcine Pancreas" Biochim. Biophys. ACTA, 1968, vol. 139, pp. 103-117.
Declaration by Clive Graham Phipps Walter (Dec C).
Declaration by Dr Jorn Borch Soe (Dec F).
Declaration by Dr M Turner.
Declaration by Dr Mark Turner (Dec G).
Declaration by Henrik Pedersen (Dec A).
Declaration by Henrik Pedersen, Masoud Rajabi Zargahi and Clive Graham Phipps Walter (Dec 2).
Declaration by Janne Brunstedt (Dec D).
Declaration by Kazuko Kato, Henrik Pedersen, Masoud Rajabi Zaghari, Clive Phipps Walter, and Janne Brunstedt (Dec I).
Declaration by Kim Borch.
Declaration by Luise Erlandsen.
Declaration by Masoud Rajabi Zargahi (Dec B).
Declaration by Masoud Rajabi Zargahi (Dec E).
Declaration by Tina Spendler.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.
Derewenda et al, "The crystal and molecular structure of the Rhizomuxor miehei Triacylglyceride Lipase at 1.9 Å Resolution", J. Mol. Biol. 1992, 227:818-839.
Derewenda, Urszula, et al., "Catalysis at the Interface: The Anatomy of a Conformational Change in a Triglyceride Lipase", Biochemistry, vol. 31, pp. 1532-1541, 1992.
Dictionary of Biochemistry and Molecular Biology, Second Edition, p. 16.
Dinkci. N, Mucor miehei den elde edilen lipaz.
Direct, A Newsletter from Danisco Ingredients, Sep. 1996.
Directive 2000/36/EC. Http://europa.eu.int/scadplus/leg/en/Ivb/121122b.htm. Dato: Jun. 16, 2004.
Drost-Lustenberger, C and Spendler T Lipopan F BG—Application and Mechanism of a new lipase for baking, Novozymes.
Drost-Lustenberger, Cornelia, et al., "Lipopan F BG-application and mechanism of a new lipase for bread baking", Cereal Food, 2003.
Drost-Lustenberger, Cornelia, et al., "Lipopan F BG-unlocking the natural strengthening potential in dough", Cereal Food, 2004.
Duan, Rui Dong, Fat Digestion and Absorption (2000), p. 25-46, publisher AOCS Press, Champaign III Coden 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Ducancel, Frederic, et al., "Complete amino acid sequence of a PLA2 from the tiger snake Notechis sculatus scutatus as deduced from a complementary DNA", Nucleic Acids Research, vol. 16, No. 18, 1988.
Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.
Dugruix (Edited by) Crystallization of Nucleic Acids and Proteins A Practical Approach.
Dutilh & Groger, "Improvement of Product Attributes of Mayonnaise by Enzymic Hydrolysis of Egg Yolk with Phospholipase A2", 1981 J. Sci. Food Agric. 32, 451-458.
Dybdal, L., et al., "Enzymes in Cereals Processing".
Eddine et al, "Cloning and expression analysis of NhL1, a gene encoding an extracellular lipase from the fungal pea pathogen Nextria haematococca MP VI (Fusarium solani f. sp. pisi) that is expressed in planta", Mol. Genet. Genomics (2001) 265: 215-224.
EFEMA Index of Food Emulsifiers Jan. 2004, 4th Edition.
Efthymiou CC et al. Development of domestic feta cheese.
Eliasson et al., "Cereals in Breadmaking—A molecular colloidal approach".
Ellaiah et al., "Production of lipase by immobilized cells of Aspergillus niger", Process Biochemistry, vol. 39, 2004, pp. 525-528.
Elyk, Alexander, et al., "Lipase-Catalyzed . . . ", JAOCS, vol. 08, No. 5, May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques(1991); vol. 11(5); pp. 594-596.
Enzymes in food processing (3rd Ed.), Academic press 1993.
EPO, Mobay Chemical Corporation—Decision of the Technical Board of Appeal 3.3.1 dated Jul. 1, 1982, *Official Journal EPO*, Oct. 1982, pp. 394-402.

Ettinger, William F. et al., "Structure of Cutinase Gene, cDNA, and the Derived Amino Acid Sequence from Phytopathogenic Fungi", Biochemistry, vol. 26, pp. 7883-7892, 1987.
Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate Streptomyces sp. (MSU-2110) endophytic on Monstera sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.
Fennema, Owen F., "Food Chemistry Second Edition, Revised and Expanded".
Fernandez-Garcia et al., "The use of lipolytic and proteolytic enzymees in the manufacture of manchego type cheese from ovine and bovine milk", 1994 J. Dairy Sci. 77: 2139-2149.
Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.
Ferrer et al, 2000, J. Chem. Technol. Biotechnol. 75, 569-576.
Finizym Technical Information, Novo Enzymes, 1981.
Fødevarenubusteriet (2003). Bekendtgørelse om indhold af transfedtsyrer I olier og fedtstoffer. Bekendtgørelse nr. 160 af Nov. 3, 2003.
Food Enzymes: Stalingase L, Gist-brocades Food Ingredients.
Food R&D. Dairy fields ingredient technology section.
Forman, Todd, "Enzymes Used in Bread Baking: An Application Update", Technical Bulletin, vol. XXVI, Issue 10, Oct. 2004.
Fox, et al.; "Isolation and some Properties of Extracellular Heat-Stable Lipases: from *Pseudomonas fluorescens* Strain AFT 36"; Journal of Dairy Research (1988); vol. 50; pp. 77-89.
Frenken N. et al (1992) Appl. Envir. Microbiol. 58 3787-3791.
Freshzyme, Product Sheet.
Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.
Frost & Sullivan, U.S. Market for Enzymes for food Applications.
Fugman, Douglas A et al Biochemica et Biophysica acia 795 (1984) 191-195.
Functional Bread-Making Properties of Lipids.
Galliard T and Dennis S (1974) Phytochemistry vol. 13, pp. 1731-1735.
Galliard, "The Enzymic Breakdown of Lipids in Potato Tuber by Phospholipid- and Galactolipid- Acyl Hydrolase Activities and by Lipoxygenase", Phytochemistry, 1970, vol. 9, pp. 1725-1734.
Gan, Z. et al., "Rapid Communication—Antisera agains: Wheat Diacylgalactosylglycerol (MGDG) and Diacyldigalactosylglycerol (DGDG)", Journal of Cereal Science, vol. 18, pp. 207-210, 1993.
Ganghro AB & Dahot MU, Sci Int. (Lahore), 1992, vol. 4, pp. 169-172.
Gemel, Joanna et al., "Comparison of galactolipase activity and free fatty acid levels in chloroplasts of chill-sensitive and chill resistant plants", European Journal of Biochemistry, vol. 166, 1987.
Geus et al (1987) Nucleic Acids Research 15(9) p. 3743-3759.
Gilbert, E. Jane, et al., "Purification and properties of extracellular lipase from *Pseudomonal aeruginosa* EF2", Journal of General Microbiology, 1991, vol. 137, pp. 2223-2229.
Gillian, B., Turgeon et al., "Cochliobolus heterostrophus using the Aspergillus nidulans amdS gene", Mol Gen Genet, 201: 450-453, 1985.
Gist-brocades, Amylase P Information Sheet.
Godfrey, Tony, et al., "Industrial Enzymology Second Edition".
Goodey et al, Yeast Biotechnology, Berry et al (eds.), Allen and Unwin, London 1987, pp. 401-429.
Graille J, Lipid Technology, vol. 5, No. 1, 1993, pp. 11-16.
GRAS Notification dated Apr. 11, 2001 by Novozymes for Lecitase$^R$ and Lipopan™ F.
Greenough et al (1996) Food Chem Toxicology 34:161-166 and PubMed abstract in respect thereof.
Greenough R J et al, Food and Chemical Toxicology, vol. 34(2), 1996, pp. 161-166.
Grindsted Products, Grindsted Bakery News.
Grindsted, "Emulsifiers for the baking industry".
Grindsted, "Grindamyl Fungal Alpha-Amylase".
Haas and Berka, 1991, Gene, 109:107-113.
Haas, et al., "Enzymatic Phosphatidylcholine Hydrolysis in Organic Solvents: An Examination of Selected Commercially Available Lipases", JAOCS, vol. 71, No. 5, May 1994, pp. 483-490.
Haas, et al.; "Lipases of the Genera *Rhizopus and Rhizomucor*. Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Hamer, Rob J., et al., "Interaction: The Keys to Cereal Quality", American Association of Cereal.
Hanlin, Richard T., "Illustrated Genera of Ascomycetes"; The American Phytopathological Society.
Hansen, Chr., Danisco and Novozymes, Apr. 3, 2002, Food Ingredients day, R&D—the main ingredients for growth.
Hara, et al.; "Comparative Study of Comercially Available Lipases in Hydrolysis Reaction of Phosphatidylcholine"; JAOCS (1997); vol. 74; No. 9, pp. 1129-1132.
Hawker, Kim L., et al., "Heterologous expression and regulation of the Neurospora crassa nit-4 pathway-specific regularatory gene for nitrate assimilation in Aspergillus nidulans", Gene., vol. 100, pp. 237-240, 1991.
Hedin, Eva M.K., et al., "Selective reduction and chemical modification of oxidized lipase cysteine mutants".
Helmsing, "Purification and Properties of Galactolipase", Biochim., Biophys., Acta, vol. 178, pp. 519-533, 1969.
Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.
Hilton S et al, Biochemistry vol. 29, No. 38, 1990, pp. 9072-9078.
Hilton S, Buckley JT, J Biol Chem. Jan. 15, 1991; 266(2): 997-1000.
Hirayama O et al, Biochim Biophys Acta. 1975, vol. 384(1), p. 127-37.
Hirose, Yoshihiko et al., "Characteristics of Immobilized Lipase PS On Chemically Modified Ceramics", Amano Pharmaceutical.
Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.
Höfelmann et al, J. Food Sci., 1985, 50:1721-1731.
Holmquist et al., "Lipases from Rhizomucor miehei and Humicola lanuginosa: Modification of the Lid covering the active site alters enantioselectivity", Journal of Protein Chemistry, vol. 12, No. 6, 1993.
Holmquist et al., "Probing a Functional Role of Glu87 and Trp89 in the Lid of Humicola lanuginosa Lipase through Transesterification Reactions in Organic Solvent", Journal of Protein Chemistry, 1995, vol. 14, No. 4, pp. 217-224.
Holmquist et al., "Trp89 in the Lid of Humicola lanuginosa Lipase is Important for Efficient Hydrolysis of Tributyrin", Lipids, vol. 29, No. 9, 1994.

Horn T et al, (1980) Nuc Acids Res Symp Ser 225-232.
Hoshino, et al.; "Calcium Ion Regulates the Release of Lipase of *Fusarium oxysporum*"; J. Biochem (1991); vol. 110; pp. 457-461.
Hoshino, et al.; "Purification and Some Characteristics of Extracellular Lipase from *Fusarium oxysporum* f. sp. lini"; Biosci. Biotech. Biochem (1992); pp. 660-664.
Hoshino, Tamotsu, et al., "Purfication and Some Characteristics of Extracellular Lipase from Fusarium oxysporum", Biosci. Biotech. Biochem., vol. 56, No. 4, pp. 660-664, 1992.
Hossen, Monjur and Hernandez, Ernesto, Lipids, vol. 39, Aug. 2004, pp. 777-782.
Hou Ching T, Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "Rhizomucor miehei Triglyceride Lipase is Processed and Secreted from Transformed Aspergillus oryzae", Lipids, vol. 24, No. 9, pp. 1989.
Humum et al., "Enzyme Catalysed Synthesis in Ambient Temperature Ionic Liquids", Biocatalysis and Biotransformation, vol. 19, pp. 331-338.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.
Ikeda H et al, Nature Biotech, vol. 21, 2003, p. 526-531.
Industrial enzimology (2nd Ed.), The Macmillan press 1996.
Ishihara et al Biochimica et Biophysica Acta 388 (1975) 413-422.
Isobe and Nokihara, Febs. Lett., 1993, 320:101-106.
Isobe K et al, Journal of Molecular Catalysis B: Enzymatic 1 (1995), pp. 37-43.
Iwai and Tsujisaka (in Lipases, Borgström and Brockman (eds.), Elsevier, Amsterdam, 1984, pp. 443-468.
Iwai, Mieko, et al., "Hydrolytic and Esterifying Actions of Crystalline Lipase of Aspergillus Niger", Osaka Municipal Technical Research Institute, Osaka, Japan.
Izco et al. Adv Food Sci vol. 21 N 3/4, (10-116) 1999.
Jacob, Jules S., et al., "The Effects of Galactolipid Depletion on the Structure of a Photosynthetic Membrane", The Journal of Cell Biology, vol. 103, Oct. 1986, pp. 1337-1347.
Jacobsberg B. & Oh C.H. (1976) Studies in Palm Oil Crystallisation, in Journal of the American Oil Chemist Society 53:609-616.
jan-Willem F. A. Simons et al., "Cloning, purification and characterisation of the lipase from *Staphylococcus epidermidis*", Eur. J. Biochem., vol. 253, pp. 675-683, 1998.
Jeng-yen Lin, Matthew, "Wheat Polar Lipids—A Theseis Submitted to the Graduate Faculty of the North Dakota State University of Agriculture and Applied Science", May 1972.
Jensen B et al "Effect and Activity of Lipases in Dough and Bread" Translation.
Jensen, B., et al., "Effekt and Wirksamkeit von Lipasen in Teig and Brot".
JJ Owens. Lecithinase Positive Bacteria in milk.
Joerger et al., "Alteration of Chain Length Selectivity of a Rhizopus delemar Lipase through Site-Directed Mutagenesis", Lipids, vol. 29, No. 6, 1994, pp. 377-384.
Jong et al.; "American Type Culture Collection Catalogue of Filamentous FUNGI"; Eighteenth edition (1991).
Joshi, et al.; "Specificity of Fungal Lipase in Hydrolytic Cleavage of Oil"; Acta Microbiologica Hungarica (1987); vol. 34(2); pp. 111-114.
Joshi, Sunita, et al., "Specificity of Lipase isolated from Fusarium oxysporum", Department of Chemistry, Indian Institute of Technology, vol. 25, No. 1 & 2, pp. 76-78.
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.
Jurgens, Catharina, et al., "Directed evolution of a $(\beta\alpha)8$-barrel enzyme to catalyze related reactions in two different metabolic pathways", PNAS, Aug. 29, 2000, vol. 97, No. 18, pp. 9925-9930.

Kaniuga Z, Acta Biochim Pol. (1997), vol. 44(1), p. 21-35.
Kapur J & Sood ML, J. Parasit., 1986, vol. 72, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kasai, Naoya, et al., "Optically Active Chlorohydrins as Chiral C3 and C4 Building Units: Microbial Resolution and Synthetic Applications", Chirality, vol. 10, pp. 682-692.
Kawamura and Doi, J. of Bacteriology Oct. 1984, p. 442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al. Korean J Dairy Sci 15 (2): 103-117 1993.
Kim, Hyung Kwoun, et al., Expression and characterization of Ca2+-independent lipase from *Bacillus pumilus* B26, Biochimica et Biophysica Acta, vol. 1583, 2002, pp. 205-212.
Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, pp . 107-112.
Kindstedt et al, Rapid Quantative test for free oil (Oiling off) in melted Mozzarella cheese.
King et al, Molecular and Cell Biology of Yeasts, Walton and Yarronton (eds.), Blackie, Glasgow, 1989, pp. 107-133.
Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of Rhizopus delemar Lipase", JAOCS, vol. 74, No. 11, 1997.
Kocak et al, Effect of lipase enzyme (palatase A 750 L) on the ripening of tulum cheese.
Kocak et al, Milchwissenschaft 51(1), 1996.
Kochubei et al Role of lipids in the organization of the closest surroundings of the reaction centers(1976) Institute of Plant Physiology.
Kochubei S M et al, Biophysics (1981), vol. 26(2), p. 299-304.
Kochubei S M et al, Mol Biol (Mosk) (1975), vol. 9(2), (p. 190-3) p. 150-153.
Kochubei SM et al, Mol Biol (Mosk) (1978),(vol. 1, p. 47-54) p. 32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al.; "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase A from Candida antarctica", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity in Lyophilized Spinach Chloroplasts", Biochimica et Biophysica Acta, 408, pp. 26-34, 1975.
KSV-5000.
Kuipers, Oscar P., et al., "Enhanced Activity and Altered Specificity of Phospholipase A2 by Deletion of a Surface Loop", Science, vol. 244, 1989.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.

Roberts, et al.; "Extracellular Lipase Production by Fungi from Sunflower Seed"; Mycologia(1987); vol. 79(2); pp. 265-273.
Roberts, Ian N., et al., Heterologous gene expression in Aspergillus niger: a glucoamylase-porcine pancreatic prophospholipase A2 fusion protein is secreted and processed to yield mature enzyme.
Robertson et al, Journal of Biological Chemistry, 1994, 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via Rhizopus arrhizus Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in Vigna unguiculata leaves and influence of drought stress", Physiologia Plantarum, vol. 104, pp. 577-586, 1998.
Sahsah, Y., et al., "Purification and characterization of a soluble lipolytic acylhydrolase from Cowpea (vigna unguiculata L.) leaves", Biochimica et Biophysica Acta, vol. 1215, pp. 66-73, 1994.
Saiki R.K. et al Science (1988) 239, pp. 487-491.
Saito, Kunihiko, et al., "Phospholipase B from Penicillium notatum", Methods in Enzymology, vol. 197.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sales Range for Baking Improver and Premix Manufacturers from DSM Bakery Ingredients.
Sambrook et al, Chapters 1, 7, 9, 11, 12 and 13—Molecular Cloning a laboratory manual, Cold Spring Harbor Laboratory Press (1989).
Sambrook, J., et al. "A Laboratory Manual, Second Edition", Plasmid Vectors, 1989.
Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent', Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols- A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Schofield, J. David, "Wheat Structure, Biochemistry and Functionality", Department of Food Science and Technology.
Scopes, Robert K., "Section 8.4: Ultrafiltration" in *Protein Purification Principles and Practice, Third Edition* (1994) Springer-Verlag, New York, p. 267-9.
Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.
Shehata PhD Thesis.
Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shillcock, Julian C., et al., "Tension-induced fusion of bilayer membranes and vesicles", Advance Online Publication.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shimada et al, JAOCS vol. 71, No. 9, (Sep. 1994).
Shin, et al.; "Butyl-Toyopearl 650 as a New Hydrophobic Adsorbent for Water-Soluable Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.
Si, Joan Qi, "Enzymes, Baking, Bread-Making".
Si, Joan Qi, "Synergistic Effect of Enzymes for Breadbaking".
Si, Joan Qi, et al. "Enzymes for bread, noodles and non-durum pasta".
Si, Joan Qi, et al., "Novamyl—A true Anti-Staling Enzyme", Cereal Food, p. 1, No. 20.
Si, Joan Qi, et al., "Synergistic Effect of Enzymes for Bread baking".
Si, Joan Qi; "New Enzymes for the Baking Industry"; Food Tech Europe (1996) pp. 60-64.
Sias B et al, Biochemistry, (2004), vol. 43(31), p. 10138-48.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oi l triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Skovgaard, et al.;"Comparison of Intra- and extracellualr isozyme banding patterns of *Fusarium Oxysporum*"; Mycol. Res. (1998); vol. 102(9); pp. 1077-1084.
Slotboom et al Chem. Phys. Lipids 4 (1970) 15-29.
Smith, George P.; "The Progeny of sexual PCR"; Nature; vol. 370; No. 18; Aug. 4, 1994.
Smith, Timothy L., et al., "The promoter of the glucoamylase-encoding gene of Aspergillus niger functions in Ustilago maydis", Gene. 88, 259-262, 1990.
Soe, J.B., "Analyses of Monoglycerides and Other Emulsifiers by Gaschromatography".
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Sorensen, H.R., et al., "Effects of added enzymes on the physicochemical characteristics of fresh durum-pasta".
Sosland, Josh, "Alive and kicking", Milling & Baking News, Feb. 24, 2004.
Soumanou, Mohamed M., et al., "Two-Step Enzymatic Reaction for the Synthesis of Pure Structured Triacylglycerides", JAOCS, vol. 75, No. 6, 1998.
Spargeon, Brad, "In China, a twist: Forgers file patents".
Spendler, et al., "Functionality and mechanism of a new 2nd generation lipase for baking industry"—Abstract. 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.

Steinstraesser, et al., "Activity of Novispirin G10 against Pseudomonas aeruginosa in Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from Candida albicans", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the Pseudomonas family", Biochimica et Biophysica Acta, vol. 1259, 1995, pp. 9-17.
Sweigard, James A., et al., "Cloning and analysis of CUT1, a cutinase gene from Magnaporthe grisea", Mol. Gen. Genet., 232:174-182, 1992.
Swinkels et al (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from Xanthomonas vesicatoria (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.
The First European Symposium of Enzymes on Grain Processing—Proceedings.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from Fusarium oxysporum catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuchiya, Atsushi et al, Ferns Microbiology Letters, vol. 143, pgs. 63-67.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of Aspergillus oryzae", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.

Turner, Progress in Industrial Microbiology, Martinelli and Kinghorn (eds.), Elsevier, Amsterdam, 1994, 29:641-666.
Unknown, "Appendix: Classification and Index of Fungi mentioned in the Text" in *Unknown*, p. 599-616.
Unknown, "Section I: Structure and Growth—Chapter 1: An Introduction to the Fungi" in *Unknown* pp. 1-16.
Unknown, *Studies on Lipase* (1964) p. 21.
Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from Candida antarctica", Structure 1994, vol. 2, No. 4.
Upton C et al TIBS Trends in Biochemical Sciences, Elsevier Publication (1995), vol. 20, pp. 178-179.
USDA, "Production of an Industrially Useful Fungal Lipase by a Genetically Altered Strain of *E. coli*", *New Technology*.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Uwajima T et al, Methods in Enzymology, 89(41), pp. 243-248.
Vaidehi, et al.; "Lipase Activity of Some Fungi Isolated from Groundnut"; Current Science (1984); vol. 53(23); p. 1253.
van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
Van Den Berg. G, Regulatory status and use of lipase in various countries.
van Gemeren, I.A., et al., "Expression and Secretion of Defined Cutinase Variants by Aspergillus awamori" Applied and Environmental Microbiology, vol. 64, No. 8, pp. 2794-2799, Aug. 1998.
van Kampen, M.D., et al., "The phospholipase activity of Staphylococcus hyicus lipase strongly depends on a single Ser to Val mutation", Chemistry and Physics of Lipids, vol. 93, 1998, pp. 39-45.
van Nieuqenhuyzen, "Open Doors to baked goods".
van Oort, Maarten G et al, Biochemistry 1989 9278-9285.
van Solingen, Pieter, et al., "The cloning and characterization of the acyltransferase gene of penicillium chrysogenum", Agricultural University, Wageningen, The Netherlands.
Vaysse et al J. of Biotechnology 53 (1997) 41-46.
Villenueva, Inform, vol. 8, No. 6, Jun. 1997.
Vujaklija, Dušica, et al., "A novel streptomycete lipase: cloning, sequencing and high-level expression of the Streptomyces rimosus GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast Torulaspora delbrueckii", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Welter, et al; "Identification of Recombinant DNA"; pp. 424-431.
Wen-Chen Suen et al., "Improved activity and thermostability of Candida antarctica lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitaker, John R., et al., "Biocatalysis in Agricultural Biotechnology", ACS Symposium Series.

Whitehead, Michael, et al., "Transformation of a nitrate reductase deficient mutant of Penicillium chrysogenum with the corresponding Aspergillus niger and A. nidulans niaD genes", Mol Gen Genet, 216: 408-411, 1989.

Wilhelm et al., "A Novel Lipolytic Enzyme Located in the Outer Membrane of Pseudomonas aeruginosa", Journal of Bacteriology, vol. 181, No. 22, Nov. 1999, pp. 6977-6986.

Williams et al Protein Analysis by Integrated Sample Preparation, Chemistry, and Mass Spectrometry, Edited by Meyers.

Winnacker, Chapter 11, pp. 424-431 in From genes to clones: introduction to gene technology, VCH (1987).

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

wirkung von Phospholipiden, "Struktur-Wirkungsbezehungen von Phospholipiden in Backwaren".

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From *Saccharomyces cerevisiae*", Biochimica et Biophysica Acta, vol. 795, 1984, pp. 117-124.

Wood et al., Eds., "Biomass, Part B, Lignin, Pectin, and Chitin", Methods in Enzymology (1988) vol. 161, Academic Press, San Diego.

Woolley et al., "Lipases their structure, biochemistry and application", Cambridge University Press.

WPI Acc No. 93-298906(38) and JP05211852 Preparation of low fat content cream-by adding lipase to mixture of fat and water.

Xu, Jun, et al., "Intron requirement for AFP gene expression in Trichoderma viride", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamano Y, Surface activity of lysophosphatidyl choline from soybean.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Yount, Nannette Y., et al., "Multidimensional signatures in antimicrobial peptides".

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Kunze, Hans, et al. "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from Torulaspora delbrueckii", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, 1994.

Larchenkova LP et al. Effect of starter and souring temperature on reproduction of *E coli* and lactobacili in milk.

Larsen N G et al, Journal of Cereal Science (1990), vol. 12(2), p. 155-164.

Lecointe et al Biotechnology Letters, vol. 18, No 8 (August) pp. 869-874.

Lee, Keun Hyeung, et al., "Identification and characterization of the antimicrobial peptide corresponding to C-terminal B-sheet domain of tenecin 1, an antibacterial protein of larvae of Tenebrio molitor", Biochem. J., 1996, vol. 334, pp. 99-105.

Lee, Kyung S., et al., The *Saccharomyces cerevisiae* PLB1 Gene Encodes a Protein Required for Lysophospholipase and Phospholipase B Activity, The Journal of Biological Chemistry, vol. 269 No. 31, Issue of Aug. 5, pp. 19725-19730.

Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of Candida albicans", The Journal of Biological Chemistry, vol. 273, No. 40, oo. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Y et al, Cereal Chemistry (1974), vol. 51(1), p. 34-45.

Lin S et al, Enzyme and Microbial Technology 18 (1996), pp. 383-387.

Lipase A "Amano" 6 Assay Note and Product Specification from Armano Pharmaceutical Co Ltd Nagoya Japan, Dec. 16, 1985.

Lipase A "Amano" 6 Assay Note and Product Specification from Armano Pharmaceutical Co Ltd Nagoya Japan, Aug. 27, 1985.

Lipase A "Amano" 6 product sheet, Apr. 1, 1999.

Lipase SP677 as a Baking Enzyme, from Novo Nordisk, Denmark, Mar. 17, 1994.

Lipomod L338P.

Lipopan F: Keep the quality—cut your costs 2000 Novozymes A/S. www.enzymes.novo.dk/cgl-bin/bvisapi.dll/biotimes/one_article.jsp?id=16947&lang=en&t=b1.

Litthauer, Derek, et al., "Pseudomonas luteola lipase: A new member of the 320- residue Pseudomonas lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Lo Y-C et al. Crystal structure of *Escherichia coli* Thioesterase I/Proteasel/Lysophospholipase L1: Consensus sequence blocks constitute the catalytic center of SGNH-hydrolases through a conserved hydrogen bond network. Journal of Molecular Biology, London, GB, vol. 330, No. 3, 539-551.

Longhi, Sonia, et al., "Atomic Resolution (1.0 Å) Crystal Structure of Fusarium solani Cutinase: Stereochemical Analysis" J. Mol. Biol. vol. 268, pp. 779-799, 1997.

Lozano et al., "Over-stabilization of Candida antarctica lipase B by ionic liquids in ester synthesis", Biotechnology Letters, vol. 23, pp. 1529-1533, 2001.

Lustenberger Abstract.

Luzi, Paola et al, Genomics (1995), vol. 26(2), p. 407-9.

Madsen J.S. & Qvist K.B. (1997) J Food Sci. 62, 579-582.

Mao, Cungui, et al., "Cloning and Characterization of a *Saccharomyces cerevisiae* Alkaline Ceramidase with Specificity for Dihydroceramide", The Journal of Biological Chemisty, vol. 275, No. 40, 2000, pp. 31369-31378.

Maria Teres Neves Petersen, PhD, "Total Internal Reflection Fluorescence Flow System with Electrochemical Control", TIRF-EC Flow System, Sep. 2002.

Marion D et al—Chapter 6, pp. 131-p. 167 of "Interactions the Keys to Cereal Quality" 1998 ISBN 0 913250-99-6 (ed. Hamer & Hoseney).

Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of Humicola lanuginosa lipase", Protein Engineering, vol. 9, No. 6, 1996, pp. 519-524.

Martinez, Chrislaine, et al., "Engineering cysteine mutants to obtain crystallographic phases with a cutinase from Fusarium solani pisi", Protein Engineering, vol. 6, No. 2, pp. 157-165, 1993.

Martinez, Diego, et al., "Genome sequence of the lignocellulose degrading fungus Phanerochaete chrysosporium strain RP78", Nature Biolgy, May 2, 2004.

Mase et al., "Purification and Characterization of a new Lipase from Fusarium sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of Penicillium notatum phospholipase B deduced from the Cdna", Eur. J. Biochem., vol. 202, pp. 783-787, 1991.

Matos AR, Lipid Catabolism: Lipid Degradation, 2000, p. 779-781.

Matos, A. R., et al., "A patatin-like protein with galactolipase activity is induced by drought stress in Vigna unguiculata leaves", Biochemical Society Transactions, vol. 28, part 6, 2000.

Matos, AR et al, Febs Letters, 491 (2001) P188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus saitoi*"; Biotiechonology and Applied Biochemistry (1987); vol. 9, pp. 401-409.

Matthes et al, (1984) EMBO J. 3, p. 801-805.

Max-Planck-Institut fur Kohlenforschung et al., "Controlling the enantioselectivity of enzymes by directed evolution: Practical and theoretical ramifications".

McAuley, Katherine E., et al., "Structure of a feruloyl esterase from Aspergillus niger", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "Further Improvements in the Yield of Monoglycerides During Enzymatic Glycerolysis of Fats and Oils".

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, No. 11, Nov. 1992.

McNeill, Gerald P., et al., "Solid Phase Enzymatic Glycerolysis of Beef Tallow Resulting in a High Yield of Monoglyceride".

Mechanism studies of the new lipase, Article, p. 1, No. 14.

Memo: From Charlotte Johanson?, "Short introduction/ status on Ferulic Acid Esterases and Acetyl Xylan Esterases", Jan. 9, 2004.

Meyer, V., et al., "Transcriptional regulation of the Antifungal Protein in Aspergillus giganteus", Mol Genet Genomics, 2002, vol. 266, pp. 747-757.

Meyers, Robert A., "Molecular Biology and Biotechnology—A Comprehensive Desk Reference".

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from Phanerochaete chrysosporium and Bjerkandera sp. BOS55", Enzyme and Microbial Technology, vol. 32, 2003, pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of Thermomyces lanuginosus Lipase by Detergents", Biochemistry, vol. 44, pp. 1719-1730, 2005.

Mohsen et al., "Specificity of Lipase Produced by Rhyopus Delemar and Its Utilization in Bread Making", Egypt. J Food. Sci. vol. 14, No. 1, pp. 175-182.

Molecular Biological Methods for Bacillus—Chapter 3 (Ed. C.R. Harwood and S.M. Cutting) 1990, John Wiley and Sons Ltd, Chichester, UK.

Mølgaard, Anne, et al., "Rhamnogalacturonan acetylesterase elucidates the structure and function of a new family of hydrolases", Structure, vol. 9, No. 4, 2000.

Molochnaya Promyshlennost 1980 No. 11 21-25, 47—abstract from Food Sci & Tech Abs.

Monick John A., Alcohols, Their Chemistry, Properties and Manufacture.

Monographs for Emulsifiers for Foods, EFEMA Nov. 1985 2nd Edition.

Moore, Charles M., et al., "Metal ion homeostasis in Bacillus subtilis", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the Fusicoccum Anamorph of Botryosphaneria Ribs"; vol. Xxx, pp. 117-125; Oct.-Dec. 1987.

Morinaga et al Biotechnology (1984) 2, p. 636-639.

Morten, T. & A., Letter, Rodovre, Jul. 2004.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Mototake, et al., "Transesterification of Oil by Fatty Acid-Modified Lipase", Technical Research Institute.

Murakami, Nobutoshi, et al., "Enzymatic Transformation of Glyceroglycolipids into sn-1 and sn-2 Lysoglyceroglycolipids by use of Rhizopus arrhizus Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.

N. V. Nederlandsch Octrooibureau Terms and Conditions.

Nagano, et al.; "Cloning and Nucleotide Sequence of cDNA Encoding a Lipase from *Fusarium keteroporum*"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao et al, JAOCS vol. 78, No. 2, 2001.

Nagao, Toshihiro et al., "Cloning and Nucleotide Sequence of CDNA Encoding a Lipase from Fusarium heterosporum", J. Biochem., vol. 116, pp. 535-540, 1994.
Nagao, Toshihiro et al., "Expression of Lipase cDNA from Fusarium heterosporum by Saccharomyces cereviisiae: High-Level Production and Purification", Journal of Fermentation and Bioengineering, 1996, vol. 81, No. 6, pp. 488-492.
Nagodawlthana et al., "Enzymes in Food Processing", Third Edition, 1993, Academic Press, Inc.
National Research Council (U.S.) Committee on Specifications of the Food Chemicals Codex, "Lipase Activity" in *Food Chemicals Codex* (1981) National Academy Press, Washington, D.C. pp. 492-493.
Needleman & Wunsch (1970), J. of Molecular Biology 48, 443-453.
Nelson and Long, Analytical Biochemistry (1989), 180, p. 147-151.
Nerland A H, Journal of Fish Diseases, vol. 19, No. 2, 1996, pp. 145-150.
Néron, et al., "Effects of lipase and the phosphlipase on the lipids hydrolysis during mixing in correlation with the oxygen consumption by wheat flour dough during kneading" available at http://www.cnam.fr/biochimie.
Ness, Jon. E., et al., "DNA shuffling of subgenomic sequences of subtilisin" Nature Biotechnology, vol. 17, Sep. 1999.
Nestle Research Center, Brochure for "Food Colloids 2006" in Montreux, Switzerland, Apr. 23-26, 2006.
Neugnot Virginie et al, European Journal of Biochemistry, 2002, vol. 269, pp. 1734-1745.
Newport, G., et al., "KEX2 Influences Candida albicans Proteinase Secretion and Hyphal Formation", The Journal of Biological Chemistry, 1997, vol. 272, No. 46, pp. 28954-28961.
Nicolas, Anne, et al., "Contribution of Cutinase Serine 42 Side Chain to the Stabilization of the Oxyanion Transition State", Biochemistry, vol. 35, pp. 398-410, 1996.
Nielsen et al., "Lipases A and B from the yeast Candida antarctica". Nierle Wet al, Fette Seifen Anstrichmittel (1981), vol. 83(10), p. 391-395.
Nierle, Von W. et al. "Weizenlipide: Funktion and Einflub bei der Verarbeitung des Mehles".
Nierle, W., et al., "Versuche zur Verlangerung der Haltbarkeit von Dartoffelprodukten", Chem. Mikrobiol. Technol. Lebensm., 1975, vol. 3, pp. 172-175.
Nobutoshi M et al, Tetrahedron Letters (1991), vol. 31(1), p. 1331-4.
Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".
Novozymes Memo—Test of lipases for EP1193314B1, Jul. 6, 2005.
Novozymes Report 2002 Annual Report.
Novozymes, "Biowhitening—a new concept for steamed bread", *Bio Times*, Jan. 2005.
Novozymes, "Breakthrough: Less Fattening Fried Food" *Bio Times*, Jun. 2001, No. 2.
Novozymes, "Enzymes for dough strengthening", 2001.
Novozymes, "Lipopan F BG- application and mechanism of a new lipase for bread baking" (Draft) *Cereal Food* (2003) (Author: Drost-Lustenberger, C. et al.).
Novozymes, "Lipopan F BG", *Cereal Foods*.
Novozymes, "Mechanism studies of the new lipase".
Novozymes, "Product Sheet for Lipopan F BG", *Cereal Food*, (2001).
Novozymes, "Product Sheet for Lipopan FS BG", *Cereal Food* (2002).
Novozymes, "Product Sheet for Lipopan S BG", *Cereal Food* (2002).
Novozymes, "Product Sheet for Noopazyme".
Novozymes, "Product Sheet for Novozym 27016" (draft);
Novozymes, "Product Sheet for Novozym 27041" (draft).
Novozymes, "Product Sheet for Novozym 27019" (draft).
Novozymes, "Product Sheet for Novozym 27080".
Novozymes, "Product Sheet for Novozym 27106".
Novozymes, "Product Sheet: Enzyme Business, Noopazyme" (draft).
Novozymes, "Product Sheet: Enzyme Business, Novozym 27019" (draft).

Novozymes, "Product Sheet: Enzyme Business, Novozym 677 BG".
Novozymes, "Revolutionizing baking", *BioTimes* (2002) pp. 6-7.
Novozymes, "Strong sales for lipase that makes dough stronger" *BioTimes*, Dec. 2003.
Novozymes, "The Novozyme Touch: Make your mark on the future".
Novozymes, "The perfect roll every time for steers", *Bio Times*, Sep. 2003.
Novozymes, "The value of innovation", *Bio Times*, Mar. 2004.
Novozymes, "The vital role of technical service in baking", *BioTimes*, Jun. 2004.
Novozymes, Lipopan 50 BG, Product Sheet.
Novozymes, Lipopan 50 BG, Product Specification.
Novozymes, Lipopan F BG, Product Data Sheet.
Novozymes, Lipopan FS BG, Product Sheet.
Novozymes. Enzymes at work.
NY metode til aktivitetsbestemme fedtnedbrydende vaskemiddelenzy.
Nylander et al., "Interaction between lipids and lipases A collection of papers presented at the European Meeting on lipid and lipase interaction at Lund University".
Ognjenovic Radomir et al, Acceleration of ripening of semi-hard cheese by proteolytic and lipolytic enzymes.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30,-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) Partial glycerides and palm oil Crystallisation, in Journal of Science and Food Agriculture 28:955.
Okiy D.A. (1978) Interaction of triglycerides and diglycerides of palm oil, in Oleagineux 33:625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
O'Mahony et al. Hydrolysis of the lipoprotein fractions of milk by Phospholipase C.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.
Osman, Mohamed, et al., "Lipolytic activity of Alternaria alternate and Fusarium oxysporum and certain properties of their lipids", Microbios Letters, vol. 39, pp. 131-135, 1988.
Ostrovskaya L K et al, Dokl Akad Nauk SSSR, (vol. 186(4), p. 961-3) p. 59-61.
O'Sullivan et al, J Plant Physiol, vol. 313, (1987) p. 393-404.
Outtrup, Günther H., et al., "Properties and Application of a Thermostable Maltogenic Amylase Produced by a Strain of Bacillus Modified by Recombinant-DNA Techniques", Starch/Starke, vol. 36, No. 12, pp. 405-411.
Palomo, Jose M., et al., "Enzymatic production of (3S, 4R)-(-)-4-(4'-fluorophenyl)-6-oxo-piperidin-3-carboxylic acid using a commerical preparation of lipase A from Candida antarctica: the role of a contaminant esterase" Tetrahedron: Asymmetry, vol. 13, 2002, pp. 2653-2659.

Palomo, Jose M., et al., "Enzymatic resolution of (±)-glycidyl butyrate in aqueous media. Strong modulation of the properties of the lipase from Rhizopus oryzae via immobilization techniques", Tetrahedron: Asymmetry, vol. 15, 2004, pp. 1157-1161.
Palomo, Jose M., et al., "Modulation of the enantioselectivity of Candida antarctica B lipase via conformational engineering: kinetic resolution of (±)-α-hydroxy-phenylacetic acid derivatives", Tetrahedron: Asymmetry, vol. 13, 2002, pp. 1337-1345.
Pariza, Michael, et al., "Evaluating the safety of Microbiol Enzyme Preparations Used in Food Processing: Update for a New Century", Regulatory Toxicology and Pharmacology, vol. 33, pp. 173-186.
Patent Abstracts of Japan vol. 016, No. 528 (C-1001), Oct. 29, 1992 & JP 04 200339 A see abstract.
Patent Abstracts of Japan vol. 095, No. 001, Feb. 28, 1995 & JP 06 296467 A see abstract.
Peelman F, et al, Protein Science Mar. 1998; 7(3): 587-99.
Penninga et al, Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the Humicola lanuginosa Lipase", Biochemistry, 1998, vol. 37, pp. 12375-12383.
Peters, G.H., et al.; "Dynamics of Rhizomucor miehei lipase in a lipid or aqueous environment: Functional role of glycines"; Dept. of Biochemistry and Molecular Biology, University of Leeds.
Peters, G.H., et al.; "Essential motions in lipases and their relationship to the biological function".
Peters, Günther H., et al., "Theoretical Investigation of the Dynamics of the Active Site Lid in Rhizomucor miehei Lipase", Biophysical Journal, vol. 71, 1996, pp. 119-129.
Philippine Patent Application Serial No. 31068.
*Phytochemical Dictionary* "Chapter 4, Sugar Alcohols and Cyclitols".
Picon et al. Biotechnology letters vol. 17 nr 10 pp. 1051-1056.
Plijter J and JHGM Mutsaers, The surface rheological properties of dough and the influence of lipase on it, Gist-brocades, Bakery Ingredients Division, Oct. 1994.
Plou et al, J. Biotechnology 92 (2002) 55-66.
Ponte J G, Cereal Chemistry (1969), vol. 46(3), p. 325-29.
Poulsen, C.H., et al., "Effect and Functionality of Lipases in Dough and Bread", The British Library.
Poulsen, Charlotte, et al. "Purification and Characterization of a Hexose Oxidase with Excellent Strenghening Effects in Bread".
Product Data Sheet, Bakezyme P 500 BG, DSM Food Specialties.
Product Description PD 40084-7a Grindamyl Exel 16 Bakery Enzyme.
Product Sheet B1324a-GB—Lecitase$^R$ Novo, Novo Nordisk.
Product Sheet, Lipozyme® 10.000 L, Novo Nordisk.
Punt and van den Hondel, Meth. Enzym., 1992, 216:447-457.
Pyler, E.J., "Baking Science and Technology Third Edition", vol. 1, 1988.
Pyler, E.J., "Baking Science and Technology Third Edition", vol. II, 1988.
Queener et al. (1994) Ann N Y Acad Sci. 721, 178-93.
Rambosek and Leach, CRC Crit. Rev. Biotechnol., 1987, 6:357-393.
Rapp, Peter, et al., "Formation of extracellular lipases by filamentous fungi, yeasts, and bacteria", Enzyme Microb. Technol., 1992, vol. 14, November.
Rapp, Peter; "Production, regulation, and some properties of lipase activity from *Fusarium Oxysporum* f. sp. *vasinfectum*"; Enzyme and Microbial Technology(1995); vol. 17; pp. 832-838.
Reetz M.T., Jaeger K.E. Chem Phys Lipids. Jun. 1998; 93(1-2): 3-14.
Reetz Manfred T, Current Opinion in Chemical Biology, Apr. 2002, vol. 6, No. 2, pp. 145-150.
Reiser J et al. (1990) Adv Biochem Eng Biotechnol. 43, 75-102.
Richardson & Hyslop, pp. 371-476 in Food Chemistry, 1985, second edition, Owen R. Fennema (ed), Manel Dekker, Inc, New York and Basel.
Richardson and Hyslop, "Enzymes: XI—Enzymes Added To Foods During Processing" in *Food Chemistry*, Marcel Dekker, Inc., New York, NY 1985.

Arskog and Joergensen, "Baking performance of prior art lipases from *Candida cylindracea*and *Aspergillus foeditus* and their actiivty on galactolipids in dough", Novozymes Report 2005.
Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.
Delphine Briand et al., "Substrate Specificity of the Lipase from *Candida parapsilosis*", Lipids, 1995, vol. 30, No. 8.
"Definition of Recombined Milk", International Dairy Federation, 1979, doc. 116, p. 5.
Stryer, L., Biochemistry, 1981, $2^{nd}$ Edition, W H Freeman and Co., San Francisco.
Patent Abstracts of Japan; Publication No. 04-370055; Publication Date Dec. 12, 1992.
Jennifer L. Seffernick et al., "Melamine Deaminase and Atrazine Chlorohydrolase: 98 Percent Identical but Functionally Different", Journal of Bacteriology, Apr. 2001, vol. 183, No. 8, pp. 2405-2410.
Andrzej Witkowski et al., "Conversion of a β-Ketoacyl Synthase to a Malonyl Decarboxylase by Replacement of the Active-Site Cysteine with Glutamine", Biochemistry, 1999, vol. 38, No. 6, pp. 11643-11650.
"AOCS Introduction to the Processing of Fats and Oils", American Oil Chemists Society, 2003, pp. III 16-III 19.
Hajime Seino et al., "Enzymatic Synthesis of Carbohydrate Esters of Fatty Acid (10 Esterification of Sucrose, Glucose, Fructose and Sorbitol", JAOCS, Nov. 1984, vol. 61, No. 11.
Roberto A. Chica et al., "Semi-rational approaches to engineering enzyme activity: combining the benefits of directed evolution and rational design", Biotechnology, 2005, vol. 16, pp. 378-384.
Garcia et al., "1, 2-Diacyl-*sn*-glycerol: Sterol Acyl Transferase from Spinach Leaves (*Spiniacia olerecea* L.)", Methods in Enzymology, vol. 71, pp. 768-772.
Sequence of enzyme GCAT (glycerophospholipidcholesterolacyltranspherase), found at http://www.ncbi.nim.nih.gov/entrez/viewer.fcgi.
Anna Maria V. Garzillo et al., "Production, purification and characterization of glucose oxidase from Penicillium variabile P16$^1$", Biotechnol. Appln. Biochem., 1995, vol. 22, pp. 169-178.
Patent Abstracts of Japan; Publication No. 48016612; Publication Date May 23, 1973.
S. Sen et al., "Developments in Directed Evolution for Improving Enzyme Functions", Appl. Biotechnol., 2007, vol. 143, No. 3, pp. 212-223.
"Purifine Enzyme", Verenium Corporation leaftlet, Jan. 2008.
Sequence alignment of database accession No. Q44268 with Seq. ID No. 16.
Sequence alignment of database accession No. Q44268 with Seq. ID No. 70.
Nerland A.H., "The Nucleotide Sequence of the Gene Encoding GCAT from Aeromonas salmonicida SSP. Salmonicida", Journal of Fish Diseases, 1996, vol. 19, No. 2, pp. 145-150, XP008049669.
Nerland A.H., "Glycerophospholipid-cholesterol acyltransferase precursor", SwissProt, Feb. 11, 2005, XP002318368.
Buckley J. Thomas, "Substrate specificity of bacterial glycerophospholipid" Cholesterol Acyltransferase, Biochemistry, 1982, vol. 21, pp. 6699-6703.
Verenium Corporation leaflet Purifine Enzyme, "Convert Gums to Oils Significantly Increase oil Yields no increase in Free Fatty Acids", San Diego, Jan. 2008.
AOCS Introduction to the Processing of Fats and Oils, four modules on CD-ROM American Oil Chemists Society, 2003, pp. 111-16-111-19.
Anguita et al.,Appl. Environ. Microbiol., 1983, vol. 59, No. 8, pp. 2411-2417.
Sutrisno et al., Journal of Bioscience and Bioengineering, 2001vol. 91, No. 6, pp. 599-602.
Kalscheuer et al., Applied and Environmental Microbiology, 2004, vol. 70, No. 12, pp. 7119-7125.
Brunel et al., J. Biotechnology, Jul. 1, 2004, vol. 111, No. 1, pp. 41-50.
U.S. Appl. No. 60/083,277, Apr. 28, 1998, Spender, Tina, et al.

AACC Method 54-21 Farinograph Method for Flour, from Physical Dough Tests supplied by the British Library, Nov. 3, 1999.
Anderson D, "A Primer in Oils Processing Technology" in Bailey's Industrial Oil and Fat Products, Sixth edition, John Wiley, 2005, vol. 5, chapter 1, p. 1-56. ISBN 978047138401.
Anguita et al, "Purification, Gene Cloning, Amino Acid Sequence Analysis, and Expression of an Extracellular Lipase from an Aeromonas hydrophila Human Isolate", Appl. Environ. Microbiol., vol. 59, No. 8, p. 2411-2417, Aug. 1993.
"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.
AOCS Introduction to the Processing of Fats and Oils p. 111-16-111-19. Four modules on CD-ROM. American Oil Chemists Society, 2003.
AOCS Method 2c-25 "1997 Moisture and Volatile Matter Air Oven Method" Sampling and Analysis of Commercial Fats and Oils, obtained from the British Library, p. 1, 1997.
AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.
Archer D.B. & Peberdy, The Molecular Biology of Secreted Enzyme Production by Fungi, Critical Reviews in Biotechnology, 1997, vol. 17, No. 4, p. 273-306.
Arskog and Joergensen, "Baking performance of prior art lipases from *Candida cylindracea* and *Aspergillus foeditus* and their activity on galactolipids in dough", Novozymes Report Jul. 18, 2005, pp. 1-2.
Arskog and Joergensen, "Baking performance of prior art lipases from *Humicola lanuginosa, Aspergillus tubigensis, Rhizopus delemar* and *Rhizomucor miehei*, and their activity on galactolipids in dough", Novozymes Report Jul. 17, 2005, pp. 1-8.
Aust K., "Applications of lecithin in bakery foods," AIB Research Technical Bulletin, vol. XV, issue 12, Dec. 1993, p. 1-6.
Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, pp. 34626-34634.
Beggs J.D., Transformation of yeast by a replicating hybrid plasmid, Nature (London), 1978, vol. 275, p. 104.
Bessette, "Efficient folding or proteins with multiple disulphide bonds in the *Escherida coli cytoplasm*", Proc. Natl. Acad. Sci. USA, 1999, vol. 96, p. 13703-13708.
Bo Yang et al., "Optimization of Enzymatic Degumming Process for Rapseed Oil," JAOCS, 2006, vol. 83, No. 7, p. 653-658.
Briand et al, "Substrate Specificity of the Lipase from Candida parapsilosis", Lipids, Aug. 1995, vol. 30, No. 8, p. 747-754.
Bru R., López-Nicolás J.M., García-Carmona F., (1995) "Aggregation of polyunsaturated fatty acid in the presence of cyclodextrins", Colloids and Surfaces A: Physiochemical and Engineering Aspects. 97, p. 263-269.
Brunel et al, "High-Level expression of Candida parapsilosis lipase/acyltransferase in Pichia pastoris," J Biotechnology, Jul. 1, vol. 111, No. 1, p. 41-50, 2004.
Buchold H. et. al., "Enzymatische Phosphatidentfernung aus Pflanzenolen" Technologies, 1993, vol. 95, No. 8, p. 300-304, ISSN:0931-5985.
Buckley J. Thomas et al., Substrate specificity of bacterial glycerophospholipid: Cholesterol Acyltransferase, Biochemistry, 1982, vol. 21, p. 6699-6703.
Bylund G. (ed), 1995, Dairy Processing Handbook, Chapter 2, p. 17-42, Lund, Sweden.
Bylund G. (ed), 1995, Dairy Processing Handbook, Chapter 9, p. 227-246, Lund, Sweden.
Ceci L.N. et al, Oil recovery and lecithin production using water degumming sludge of crude soybean oils, Journal of the Science of Food and Agriculture, 2008, vol. 88, No. 14, p. 2460-2466.
Cereghino et al., Heterologous protein expression in the methylotrophic yeast *Pichia pastoris*, FEMS Microbiology Review, 2000, vol. 24, No. 1, p. 45-66.

Chica et al, "Semi-rational approaches to engineering enzyme activity: combining the benefits of directed evolution and rational design" Current Opinion in Biotechnology, 2005, vol. 16, p. 378-384.
Christou P., Genetic engineering of crop legumes and cereals: current status and recent advances, Agro-Food-Industry Hi-Tech, Mar./Apr. 1994, p. 17-27.
Davis R.H. and de Serres, Genetic and Microbiological Research Techniques for *Neurospora crassa*, Methods Enzymology, 1971, vol. 17A, p. 79-143.
EC 1.1.3.10 (downloaded—Jul. 12, 2010 from http://www.chem.qmul.ac.uk/iubmb/enzyme/EC1/1/3/10.html).
EC 1.1.3.4 (downloaded—Jul. 12, 2010 from http://www.chem.qmul.ac.uk/iubmb/enzyme/EC1/1/3/4.htmll).
EC 1.1.3.5 (downloaded—Nov. 16, 2009 from http://www.chem.qmul.ac.uk/iubmb/enzyme/EC1/1/3/5.html).
EC 2.3.1.43 (downloaded Apr. 21, 2009 from http://www.chem.qmul.ac.uk/iubmb/enzyme/EC2/3/1/43.html).
EC 2.4.1.19 (Downloaded Jul. 12, 2010 from http://www.chem.qmul.ac.uk/iubmb/enzyme/EC2/4/1/19.html).
EC 3.1.1.26 (downloaded—Dec. 18, 2008 from http://www.chem.qmul.ac.uk/iubmb/enzyme/EC3/1/1/26.html).
EC 3.1.1.3 (downloaded—Dec. 18, 2008 from http://www.chem.qmul.ac.uk/iubmb/enzyme/EC3/1/1/3.html).
EC 3.1.1.32 (downloaded—May 22, 2008 from http://www.chem.qmul.ac.uk/iubmb/enzyme/EC3/1/1/32.html).
EC 3.1.1.4 Phospholipase A2 enzyme Enzyme Entry 1983 (downloaded Apr. 21, 2009 from http://www.chem.qmul.ac.uk/iubmb/enzyme/EC3/1/1/4.html).
EC 3.1.1.5 (downloaded Dec. 18, 2008 from http://www.chem.qmul.ac.uk.iubmb/enzyme/EC3/1/1/5.html).
EC 3.2.1.3 (downloaded Jul. 12, 2010 from http://www.chem.qmul.ac.uk/iubmb/enzyme/EC3/2/1/3.html).
EC 3.2.1.32 (Downloaded Jul. 12, 2010 from http://www.chem.qmul.ac.uk/iubmb/enzyme/EC3/2/1/32.html).
EC 3.2.1.60 (downloaded Apr. 28, 2009from http://www.chem.qmul.ac.uk/iubmb/enzyme/EC3/2/1/60.html).
Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, p. 31-45.
Garzillo et al, "Production, Purification, and Characterization of Glucose Oxidase from Penicillium Variable P16," Biotechnol. Appl. Biochem., 1995, vol. 22, p. 169-178.
Genbank accession code NC_003888.1:8327480..8328367 (downloaded Apr. 21, 2009), p. 1.
Genbank accession No. AL646052 (downloaded Apr. 21, 2009), pp. 1-2.
Genbank accession No. AL939131.1:265480..266367 (downloaded Apr. 21, 2009), p. 1.
Genbank accession No. CAC42140 (downloaded Apr. 21, 2009), pp. 1-2.
Genbank accession No. NP_003888.1 (downloaded Apr. 21, 2009), pp. 1.
Genbank accession No. NP_631558.1 (downloaded Apr. 21, 2009), pp. 1-2.
Genbank accession No. P41734 (downloaded Apr. 21, 2009), pp. 1-4.
NCBI Accession No. Z75034 (downloaded Apr. 21, 2009) p. 1-2.
Hammond E.G. et al., "Soybean Oil" in Bailey's Industrial Oil and Fat Products, Sixth edition, John Wiley, 2005, vol. 3, chapter 13, p. 577-653. ISBN 978047138401.
Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.
Hinnen A. et al., Transformation of yeast, Proceedings of the National Academy of Sciences USA, Apr. 1978, vol. 75, No. 4, p. 1929-1933.
Hollenberg C.P. et al., Production of recombinant proteins by methylotrophic yeasts, Current Opinion in Biotechnology Oct. 1997, vol. 8, No. 5, pp. 554-560.
Horwell DC, "The 'peptoid' approach to the design of non-peptide, small molecular agonists and antogonists of neuropeptides", Trends Biotechnol., 1995, vol. 13, No. 4, pp. 132-134.

Hossen, Monjur, "Enzyme catalyzed synthesis of structured phospholipids with conjugated linoleic acid and plant sterols," A Dissertation by MD Monjur Hossen, May 2005, p. 1-152.

Hui, Bailey's Industrial Oil and Fat Products, 5th edition vol. 2 Edible Oil and Fat Products: Oils and Oilseeds, Wiley Interscience (1996), pp. 513-516. ISBN 0471594261.

International Dairy Federation Bulletin Document 116, 1979, p. 5, "Definition of recombined milk".

Ito H. et al., "Transformation of Intact Yeast Cells Treated with Alkali Cations," J. Bacteriology, 1983, vol. 153, p. 163-168.

Jost R. et. al., "Milk and Dairy Products," Nestle Product Technology Center, 2007, Wiley-VCH, pp. 1-62, Konolfingen, Switzerland.

Kalscheuer et al, "Synthesis of Novel Lipids in Saccharomyces cerevisiae by Heterologous Expression of an Unspecific Bacterial Acyltransferase," Applied and Environmental Microbiology, vol. 70, No. 12, p. 7119-7125, 2004.

Kane, "Effects of rare codon clusters on high-level expression of heterolgous proteins in *E. coli*" Current Opinion Biotechnology, 1995, vol. 6, p. 494-500.

Kimmel, A. et al. "Preparation of cDNA and the Generation of cDNA Libraries: Overview," Methods in Enzymology, 1987, vol. 152, p. 307-316.

LaVallie T.M., 2-Methoxyestradiol Inhibits Proliferation and Induces Apoptosis Independently of Estrogen Receptors α and β, Current Opinion in Biotechnology, 1995, vol. 6, No. 5, pp. 501-506.

Leon et al., "A new approach to study starchy changes occurring the double-baking process and during bread storage," Z. Lebensn. Unters Forsch A, 1997, vol. 204 pp. 316-320.

McIntyre et al., "Distribution of Glycerophospholipid-Cholesterol Acyltransferase in Selected Bacterial Species," Journal of Bacteriology, Jul. 1979, vol. 139, No. pp. 132-136.

NCBI protein accession code AAK84028.1 GI:15082088, (downloaded Dec. 18, 2009), pp. 1-2.

NCBI protein accession code CAB39707.1 GI:4529178, (downloaded Dec. 18, 2009), pp. 1-2.

NCBI protein accession code CAB62724.1 GI:6562793, (downloaded Dec. 18, 2009), pp. 1-2.

NCBI protein accession code CAB88833.1 GI:7635996, (downloaded Dec. 18, 2009), pp. 1-2.

NCBI protein accession code CAB89450.1; GI:7672261, (downloaded Dec. 18, 2009), pp. 1-2.

NCBI protein accession code CAC01477.1 GI:9716139, (downloaded Dec. 18, 2009), pp. 1-2.

NCBI's Genbank database accession No. 1IVN_A; GID:33357066, (downloaded Oct. 14, 2010), pp. 1-2.

Nerland A.H., "Glycerophospholipid-cholesterol acyltransferase precursor", SwissProt, Feb. 11, 2005 XP002318368 citing Nerland, A.H., "The nucleotide sequence of the gene encoding GCAT from Aeromonas salmonicida ssp. Salmonicida," Journal of Fish Diseases, vol. 19, p. 145-150, 1996.

Oil Mill Gazetteer, "Enzymatic Degumming Improves Oil Refining in China," Jul. 2005 vol. 111, p. 2-4.

Phospholipase C, E.C. 3.1.4.3, (downloaded Sep. 8, 2009 from http://www.chem.qmul.ac.uk/iubmb/enzyme/EC3/1/4/3.html), p. 1.

Poldermans B and Schoppink P, "Controlling the baking process and product quality with enzymes", Cereal Foods World, Mar. 1999, 44 (3), p. 132-135.

Potrykus I., Gene Transfer to Plants: assessment of published approaches and results, Annu. Rev. Plant Physiol. Plant Mol. Biol., 1991, vol. 42, p. 205-225.

PreSens Manual HydroPlate® HP96U and HydroPlate® HP96C, pp. 1-15, Aug. 17, 2004.

Seffernick et al, "Melamine Deaminase and Atrazine Chlorohydrolase: 98 Percent Identical but Functionally Different", Journal of Bacteriology, Apr. 2001, vol. 183, No. 8, p. 2405-2410.

Seino et al, "Enzymatic Synthesis of Carbohydrate Esters of Fatty Acid (10 Esterification of Sucrose, Glucose, Fructose and Sorbitol", J. Am. Oil Chem. Soc., Nov. 1984, vol. 61, No. 11, p. 1761-1765.

Sequence alignment of database accession No. Q44268 (database: UNIProtKB/TrEMBL) with SEQ. ID No. 16, (downloaded Jan. 27, 2009), pp. 1-2.

Sequence alignment of database accession No. Q44268 (database: UNIProtKB/TrEMBL) with SEQ. ID No. 70, (downloaded Jan. 27, 2009), pp. 1-2.

Simon RJ et al.,"Peptoids: a modular approach to drug discovery", Proc. Natl. Acad. Sci. USA, 1992, vol. 89, No. 20, pp. 9367-9371.

Stryer, "Conformation and Dynamics," Biochemistry, 2nd Edition, 1981, WH Freeman & Co., San Francisco, p. 16.

Sutrisno, A. et al, "Expression of a gene Encoding Chitinase (pCA 8 ORF) from Aeromonas sp. No. 10S-24 in *Esxherichia coli* and Enzyme Characterization," Journal of Bioscience and Bioengineering, vol. 91, No. 6, pp. 599-602, 2001.

Szuhaj B.F., "Lecithins" in Bailey's Industrial Oil and Fat Products, Sixth edition, John Wiley, 2005, vol. 2, chapter 13, p. 361-456. ISBN 978047138401.

Tanji M.et al., "Lipase hydrolysis of milk fat and its soft fractions", Research Bulletin of Obihiro University, 2001, vol. 22, No. 2, p. 89-94.

Tilden E.B. and Hudson C.S., Preparation and Properties of the Amylases Produced by Bacillus Macerans and Bacillus Polymyxa, J. Bacteriology, 1942, vol. 43, p. 527-544.

Torres C.F. et al., A two steps enzymatic procedure to obtain sterol esters, tocopherols and fatty acid ethyl esters from soybean oil deodorizer distillate, Process Biochemistry, 2007, vol. 42, No. 9, p. 1335-1341.

Trueman L.J., "Heterologous Expression in Yeast," Methods Molecular Biology, vol. 49, p. 341-354 (1995).

Turner G. Vectors for generic manipulation, in Martinelli S.D, Kinghorn J.R. (editors), *Aspergillus*: 50 years on. Progress in industrial microbiology, 1994, vol. 29, p. 641-666.

Verenium Corporation leaflet Purifine® Enzyme"Convert Gums to Oils Significantly Increase Oil Yields no increase in Free Fatty Acids", San Diego, Jan. 2008.

Witkowski et al, "Conversion of a B-Ketoacyl Synthase to a Malonyl Decarboxylase by Replacement of the Active-Site Cysteine with Glutamine," Biochemistry, Sep. 7, 1999 vol. 38, No. 36, p. 11643-11650.

Notification of Reasons for Refusal: JP Application No. 526105, Feb. 12, 2003 (Translation).

Notification of Reasons for Refusal: JP Application No. 526105, Jun. 4, 2002 (Translation).

Written Argument: JP Application No. 97181706.5, (Dec. 9, 1997) (Translation).

Internal Novo Nordisk Ref No. DK5559215, p. 3-10 (NZAS-0017041-0017048) submitted during litigation.

\* cited by examiner

FIGURE 10

SEQ ID No. 16

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 11

(SEQ ID No. 1)

```
  1  MKKWFVCLLG LVALTVQAAD SRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL FNLPDLGQNP SARSQKVVEA VSHVSAYHNQ
201  LLLNLARQLA PTGMVKLFEI DKQFAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATFIANQY EFLAH*
```

FIGURE 12

(SEQ ID No. 2)

```
  1  ivafGDSlTd geayygdsdg ggwgagladr Ltallrlrar prgvdvfnrg isGrtsdGrl
 61  ivDalvallF laqslglpnL pPYLsgdflr GANFAsagAt Ilptsgpfli QvqFkdfksq
121  vlelrqalgl lqellrllpv ldakspdlvt imiGtNDlit saffgpkste sdrnvsvpef
181  kdnlrqlikr Lrsnngarii vlitlvilnl gplGClPlkl alalassknv dasgclerln
241  eavadfneal relaiskled qlrkdglpdv kgadvpyvDl ysifqdldgi qnpsayvyGF
301  ettkaCCGyG gryNynrvCG naglcnvtak aCnpssylls flfwDgfHps ekGykavAea
361  l
```

FIGURE 13

(SEQ ID No. 3)

```
  1  mkkwfvcllg lvaltvqaad srpafsrivm fgdslsdtgk myskmrgylp ssppyyegrf
 61  sngpvwleql tnefpgltia neaeggptav aynkiswnpk yqvinnldye vtqflqkdsf
121  kpddlvilwv gandylaygw nteqdakrvr daisdaanrm vlngakeill fnlpdlgqnp
181  sarsqkvvea ashvsayhnq lllnlarqla ptgmvklfei dkqfaemlrd pqnfclsdqr
241  nacyggsyvw kpfasrsast dsqlsafnpq erlaiagnpl laqavaspma arsastlnce
301  gkmfwdqvhp ttvvhaalse paatfiesqy eflah
```

FIGURE 14

SEQ ID No. 4

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIGURE 15

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 16

SEQ ID No. 6

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 17

SEQ ID No. 7

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIGURE 18

(SEQ ID No. 8)

```
                10         20         30         40         50         60
                 |          |          |          |          |          |
         MNLRQWMGAA TAALALGLAA CGGGGTDQSG NPNVAKVQRM VVFGDSLSDI GTYTPVAQAV 70         80         90        100        110        120
                 |          |          |          |          |          |
         GGGKFTTNPG PIWAETVAAQ LGVTLTPAVM GYATSVQNCP KAGCFDYAQG GSRVTDPNGI 130        140        150        160        170        180
                 |          |          |          |          |          |
         GHNGGAGALT YPVQQQLANF YAASNNTFNG NNDVVFVLAG SNDIFFWTTA AATSGSGVTP 190        200        210        220        230        240
                 |          |          |          |          |          |
         AIATAQVQQA ATDLVGYVKD MIAKGATQVY VFNLPDSSLT PDGVASGTTG QALLHALVGT 250        260        270        280        290        300
                 |          |          |          |          |          |
         FNTTLQSGLA GTSARIIDFN AQLTAAIQNG ASFGFANTSA RACDATKINA LVPSAGGSSL 310        320        330        340
                 |          |          |          |
         FCSANTLVAS GADQSYLFAD GVHPTTAGHR LIASNVLARL LADNVAH
```

FIGURE 19 (SEQ ID No. 9)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIGURE 20

(SEQ ID No. 10)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIGURE 21

(SEQ ID No. 11)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqspit
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvinspela drdailtglr tlvdraharg
361 lrvvgatitp fggyggytea retmrqevne eirsgrvfdt vvdfdkalrd pydprrmrsd
421 ydsgdhlhpg dkgyarrngav idlaalkgaa pvka
```

FIGURE 22 (SEQ ID No. 12)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrirtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrvs eaepsspsgv
```

FIGURE 23 (SEQ ID No. 13)

```
  1 mgrgtdqrtr ygrrrarval aaltaavigv gvagcdsvgg dspapsgsps krtrtapawd
 61 tspasvaavg dsitrgfdac avlsdcpevs watgssakvd slavrllgka daaehswnya
121 vtgarrnadlt aqvtraaqre pelvavrnaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIGURE 24 (SEQ ID No. 14)

```
  1 mrlsrraata sallltpala lfgasaavsa prlqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

FIGURE 25 (SEQ ID No. 15)

```
  1  MKKWFVCLLG LIALTVQAAD TRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL FNLPDLGQNP SARSQKVVEA VSHVSAYHNK
201  LLLNLARQLA PTGMVKLFEI DKQFAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATFIETQY EFLAHG*
```

Figure 2B (SEQ ID NO. 17)

```
Met Arg Tyr Phe Ala Ile Ala Phe Leu Leu Ile Asn Thr Ile Ser Ala
 1               5                  10                  15
Phe Val Leu Ala Pro Lys Lys Pro Ser Gln Asp Asp Phe Tyr Thr Pro
                20                  25                  30
Pro Gln Gly Tyr Glu Ala Gln Pro Leu Gly Ser Ile Leu Lys Thr Arg
                35                  40                  45
Asn Val Pro Asn Pro Leu Thr Asn Val Phe Thr Pro Val Lys Val Gln
            50                  55                  60
Asn Ala Trp Gln Leu Leu Val Arg Ser Glu Asp Thr Phe Gly Asn Pro
 65                 70                  75                  80
Asn Ala Ile Val Thr Thr Ile Ile Gln Pro Phe Asn Ala Lys Lys Asp
                    85                  90                  95
Lys Leu Val Ser Tyr Gln Thr Phe Glu Asp Ser Gly Lys Leu Asp Cys
                100                 105                 110
Ala Pro Ser Tyr Ala Ile Gln Tyr Gly Ser Asp Ile Ser Thr Leu Thr
                115                 120                 125
Thr Gln Gly Glu Met Tyr Tyr Ile Ser Ala Leu Leu Asp Gln Gly Tyr
    130                 135                 140
Tyr Val Val Thr Pro Asp Tyr Glu Gly Pro Lys Ser Thr Phe Thr Val
145                 150                 155                 160
Gly Leu Gln Ser Gly Arg Ala Thr Leu Asn Ser Leu Arg Ala Thr Leu
                165                 170                 175
Lys Ser Gly Asn Leu Thr Gly Val Ser Ser Asp Ala Glu Thr Leu Leu
                180                 185                 190
Trp Gly Tyr Ser Gly Gly Ser Leu Ala Ser Gly Trp Ala Ala Ala Ile
        195                 200                 205
Gln Lys Glu Tyr Ala Pro Glu Leu Ser Lys Asn Leu Leu Gly Ala Ala
    210                 215                 220
Leu Gly Gly Phe Val Thr Asn Ile Thr Ala Thr Ala Glu Ala Val Asp
225                 230                 235                 240
Ser Gly Pro Phe Ala Gly Ile Ile Ser Asn Ala Leu Ala Gly Ile Gly
                245                 250                 255
Asn Glu Tyr Pro Asp Phe Lys Asn Tyr Leu Leu Lys Lys Val Ser Pro
                260                 265                 270
Leu Leu Ser Ile Thr Tyr Arg Leu Gly Asn Thr His Cys Leu Leu Asp
            275                 280                 285
Gly Gly Ile Ala Tyr Phe Gly Lys Ser Phe Phe Ser Arg Ile Ile Arg
    290                 295                 300
Tyr Phe Pro Asp Gly Trp Asp Leu Val Asn Gln Glu Pro Ile Lys Thr
305                 310                 315                 320
Ile Leu Gln Asp Asn Gly Leu Val Tyr Gln Pro Lys Asp Leu Thr Pro
                325                 330                 335
Gln Ile Pro Leu Phe Ile Tyr His Gly Thr Leu Asp Ala Ile Val Pro
                340                 345                 350
```

```
Ile Val Asn Ser Arg Lys Thr Phe Gln Gln Trp Cys Asp Trp Gly Leu
            355                 360                 365
Lys Ser Gly Glu Tyr Asn Glu Asp Leu Thr Asn Gly His Ile Thr Glu
    370                 375                 380
Ser Ile Val Gly Ala Pro Ala Ala Leu Thr Trp Ile Ile Asn Arg Phe
385                 390                 395                 400
Asn Gly Gln Pro Pro Val Asp Gly Cys Gln His Asn Val Arg Ala Ser
                405                 410                 415
Asn Leu Glu Tyr Pro Gly Thr Pro Gln Ser Ile Lys Asn Tyr Phe Glu
            420                 425                 430
Ala Ala Leu His Ala Ile Leu Gly Phe Asp Leu Gly Pro Asp Val Lys
            435                 440                 445
Arg Asp Lys Val Thr Leu Gly Gly Leu Leu Lys Leu Glu Arg Phe Ala
    450                 455                 460
Phe
465
```

FIGURE 29   (SEQ No. 18)

```
Met Arg Tyr Phe Ala Ile Ala Phe Leu Leu Ile Asn Thr Ile Ser Ala
 1               5                  10                  15
Phe Val Leu Ala Pro Lys Lys Pro Ser Gln Asp Asp Phe Tyr Thr Pro
             20                  25                  30
Pro Gln Gly Tyr Gln Ala Gln Pro Leu Gly Ser Ile Leu Lys Thr Arg
         35                  40                  45
Asn Val Pro Asn Pro Leu Thr Asn Val Phe Thr Pro Val Lys Val Gln
     50                  55                  60
Asn Ala Trp Gln Leu Leu Val Arg Ser Glu Asp Thr Phe Gly Asn Pro
 65                  70                  75                  80
Asn Ala Ile Val Thr Thr Ile Ile Gln Pro Phe Asn Ala Lys Lys Asp
                 85                  90                  95
Lys Leu Val Ser Tyr Gln Thr Phe Glu Asp Ser Gly Lys Leu Asp Cys
             100                 105                 110
Ala Pro Ser Tyr Ala Ile Gln Tyr Gly Ser Asp Ile Ser Thr Leu Thr
         115                 120                 125
Thr Gln Gly Glu Met Tyr Tyr Ile Ser Ala Leu Leu Asp Gln Gly Tyr
     130                 135                 140
Tyr Val Val Thr Pro Asp Tyr Glu Gly Pro Lys Ser Thr Phe Thr Val
145                 150                 155                 160
Gly Leu Gln Ser Gly Arg Ala Thr Leu Asn Ser Leu Arg Ala Thr Leu
             165                 170                 175
Lys Ser Gly Asn Leu Thr Gly Val Ser Ser Asp Ala Glu Thr Leu Leu
             180                 185                 190
Trp Gly Tyr Ser Gly Gly Ser Leu Ala Ser Gly Trp Ala Ala Ala Ile
         195                 200                 205
Gln Lys Glu Tyr Ala Pro Glu Leu Ser Lys Asn Leu Leu Gly Ala Ala
     210                 215                 220
Leu Gly Gly Phe Val Thr Asn Ile Thr Ala Thr Ala Glu Ala Val Asp
225                 230                 235                 240
Ser Gly Pro Phe Ala Gly Ile Ile Ser Asn Ala Leu Ala Gly Ile Gly
             245                 250                 255
Asn Glu Tyr Pro Asp Phe Lys Asn Tyr Leu Leu Lys Lys Val Ser Pro
             260                 265                 270
Leu Leu Ser Ile Thr Tyr Arg Leu Gly Asn Thr His Cys Leu Leu Asp
         275                 280                 285
Gly Gly Ile Ala Tyr Phe Gly Lys Ser Phe Phe Ser Arg Ile Ile Arg
     290                 295                 300
Tyr Phe Pro Asp Gly Trp Asp Leu Val Asn Gln Glu Pro Ile Lys Thr
305                 310                 315                 320
Ile Leu Gln Asp Asn Gly Leu Val Tyr Gln Pro Lys Asp Leu Thr Pro
                 325                 330                 335

Gln Ile Pro Leu Phe Ile Tyr His Gly Thr Leu Asp Ala Ile Val Pro
                 340                 345                 350
    Ile Val Asn Ser Arg Lys Thr Phe Gln Gln Trp Cys Asp Trp Gly Leu
                 355                 360                 365
    Lys Ser Gly Glu Tyr Asn Glu Asp Leu Thr Asn Gly His Ile Thr Glu
        370                 375                 380
    Ser Ile Val Gly Ala Pro Ala Ala Leu Thr Trp Ile Ile Asn Arg Phe
    385                 390                 395                 400
    Asn Gly Gln Pro Pro Val Asp Gly Cys Gln His Asn Val Arg Ala Ser
                        405                 410                 415
    Asn Leu Glu Tyr Pro Gly Thr Pro Gln Ser Ile Lys Asn Tyr Phe Glu
                420                 425                 430
    Ala Ala Leu His Ala Ile Leu Gly Phe Asp Leu Gly Pro Asp Val Lys
                435                 440                 445
    Arg Asp Lys Val Thr Leu Gly Gly Leu Leu Lys Leu Glu Arg Phe Ala
        450                 455                 460
    Phe His His His His His
    465                 470
```

FIGURE 30

FIGURE 31
  (SEQ ID No. 19)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldiwslrs vqdrrawdad rlhlspeght
181 rvalragqal glrvpadpdq pwpplpprgt ldvrrddvhw areylvpwig rrlrgessgd
241 hvtakgtlsp daiktriaav a
```

Figure 32

(SEQ ID No. 25)

```
  1  MFKFKKNFLV GLSAALMSIS LFSATASAAS ADSRPAFSRI VMFGDSLSDT
 51  GKMYSKMRGY LPSSPPYYEG RFSNGPVWLE QLTKQFPGLT IANEAEGGAT
101  AVAYNKISWN PKYQVINNLD YEVTQFLQKD SFKPDDLVIL WVGANDYLAY
151  GWNTEQDAKR VRDAISDAAN RMVLNGAKQI LLFNLPDLGQ NPSARSQKVV
201  EAVSHVSAYH NQLLLNLARQ LAPTGMVKLF EIDKQFAEML RDPQNFGLSD
251  VENPCYDGGY VWKPFATRSV STDRQLSAFS PQERLAIAGN PLLAQAVASP
301  MARRSASPLN CEGKMFWDQV HPTTVVHAAL SERAATFIAN QYEFLAH**
```

FIGURE 33

(SEQ ID NO. 26)

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

Figure 34

SEQ ID No. 27

ZP_00058717

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 35

(SEQ ID No. 28)

```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 36

(SEQ ID No. 29)

```
  1 mrttviaasa lllllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 37

(SEQ ID No. 30)

ZP_00094165

```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk //
```

FIGURE 38

SEQ ID No. 31

NP_625998.

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
//
```

FIGURE 39

SEQ ID No. 32

NP_827753.
```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
//
```

FIGURE 40

SEQ ID No. 33

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

Figure 43

```
1DEOm      T T V Y  L  A G D S T M A K n - - - - - - - - - - - - - - - G G G S G T N G W G E Y L
1IVNm      s1s1s1s1 s1 s1s1h?h?h?                                      h1h1h1h1h1
1IVNm      A D T L L  I  L G D B L S A G - - - - - - - - - - - - - - - Y R M B A S A A W P A L L
           s1s1s1s1 s1 s1s1h h h                                       h1h1h1h1h1
P10480m    I V     M F G D S L S D T g k m y s k m r g Y l p s P P Y Y e G R F S N G P V W L E Q L

1DEOm      A S Y L S  A  T V - - - - - - - - - - - V N D A V  A  G  R  S - - - A R S Y T R E G R F E N I A
           h1h1h1    s2 s2 s2                     s2s2s2s2s2  h3                h3h3h3h3h3h3h3h3h3h3h3
1IVNm      N D K W q  s  k - - - - - - - - - - t s V V N A S  I  S  G  D  T - - - - S Q Q G L A  R L P A L L
           h1h1h1    s2?s2?                    s2?s2s2s2s2s2                      h3h3h3h3h3  h3h3h3h3h3
P10480m    T N E F P  G  L T i a n e a e g g p t a v a Y N K K I  s  W  N  P  K    y q v I N N L D Y E V T Q F L Q

1DEOm      D  V V T   A  G D Y V I V E F G H N  D G  g s l s t d n  g  t - - - - a E V C Y S V Y D G V N E T I
           h3 h3          s4 s4s4s4s4s4         s? s? s? s? s?     s?  s?           s?s?s?s?s?s?s?s?s?s?s?s?s?s?s?
1IVNm      K Q H Q P      R W V L V E L G G N  D G - - - - - - - - - - - - - - - - L R G F Q P
           h3 h3 h3       s4 s4 s4 s4 s4                                           h4
P10480m    K D S F K   P  D D L V I L W V G A N  D Y - - - - - - - - - - - - - - L A Y G W N T E Q D A

1DEOm      L T F P A  Y  L E N A A K L F T A K   G A K V I L S S s5 Q  T  P  N  N P W E T G T F V N S P T R
           h4h4h4h4   h4 h4h4h4h4h4h4h4h4h4h4      s5s5s5s5s5 s5
1IVNm      Q Q T E Q  T  L R Q I L Q D V K a A   N A E P l l m q    L  R  L  P  A N Y G R - - - - R Y N E A
           h4h4h4h4   h4 h4h4h4h4h4h4h4h4h4h4      s5s5s5s5s5s5s?s?s?s?                                       h5h5h5h5h5
P10480mK   R V R D    A  I S D A A N R M V L N   G A K E I L L F N  L  P  d  l g g n P S A R S Q K V V E A A S H V S A

1DEOm      F V E Y  A  E L A A E V A - - - - - - - - G  V  E  Y  V  D H W S Y V D S I Y E T L  G N A T v n - -
           h5h5h5h5 h5 h5h5h5h5h5h5h5                s6 s6 s6 s6 s6?h6h6h6h6h6h6h6h6h6h6       h  h  h
1IVNm      F S A I  Y  P K L A k e - - - - - - - - - - - f D  V  P  L L  P F F M E E V Y        L K P Q W - - - -
           h5h5h5h5 h5 h5h5h5h5                         h5   s6s6s6s6s? h6 h6 h6h6
P10480mY   H N Q L  L  L N L A r g l a p t g m v k l f e i D  K  Q  F A E M L R D P Q N F G L S D Q R N a c Y g g

1DEOm      - - - - - - - - - - - - - - - - - - - - - - - - - - - - - - - - - - - - - - -
1IVNm      - - - - - - - - - - - - - - - - - - - - - - - - - - - - - - - - - - - - - - -
P10480m s y v w k  p f a s r s a s t d s g l s a f n p q e   r  l a l  a g n p i l a g a v a s p m a a r s a s t

1DEOm      - - - - - Y  F P I D H T S P A  G A E V V A E A  F  L  K A   V V C T G T S L K S V L T T T S F E G T C
1IVNm      - - - - - - - - - - - - - - - - - - - - - - - - - - - - - - - - - - - - - - -                h?h?h?
           s?s?s?h? h7 h7h7h7h7h7h7h7h7      h7 h7 h7 h7
P10480m    - M Q D D G I H P N R D  A Q P F I A D W  M  A  K  Q  L Q P L V N H D S L E
           s  s         h7h7h7h7h7h7h7 h7h7h7h7h7h7h7h7h7h7

(SEQ ID No. 34)

ADSRPAFSRIVMFGDSLSDTGKMYSKMRGYLPSSPPYYEGRFSNGPVWLEQLTNEFPG
LTIANEAEGGPTAVAYNKISWNPKYQVINNLDYEVTQFLQKDSFKPDDLVILWVGANDYL
AYGWNTEQDAKRVRDAISDAANRMVLNGAKEILLFNLPDLGQNPSARSQKVVEAASHV
SAYHNQLLLNLARQLAPTGMVKLFEIDKQFAEMLRDPQNFGLSDQRNACYGGSYVWKP
FASRSASTDSQLSAFNPQERLAIAGNPLLAQAVASPMAARSASTLNCE
GKMFWDQVHPTTVVHAALSEPAATFIESQYEFLAH

FIGURE 45

(SEQ ID No. 35)

```
  1  ADTRPAFSRI VMFGDSLSDT GKMYSKMRGY LPSSPPYYEG RFSNGPVWLE QLTKQFPGLT
 61  IANEAEGGAT AVAYNKISWN PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 46

(SEQ ID No. 36)

ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT

FIGURE 47

(SEQ ID NO. 37):

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 48

SEQ ID No. 38

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws ippkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 49

(SEQ ID No. 39)

```
   1 ggtggtgaac cagaacaccc ggtcgtcggc gtgggcgtcc aggtgcaggt gcaggttctt
  61 caactgctcc agcaggatgc cgccgtgcc gtgcacgatg gccttgggca ggcctgtggt
 121 ccccgacgag tacagcaccc atagcggatg gtcgaacggc agcggggtga actccagttc
 181 cgcgccttcg cccgcggctt cgaactccgc ccaggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcaccccga agtcggggga
 421 acaggacgac caggtcgcac cgatcgcggc gcaggcgagg aatgcggccg tcgcctcggc
 481 gatgttcggc aggtaggcca cgacccggtc gccggggccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg ggcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctcccctaa cgctccccgg tgacggagtg
1021 ttgtgcacca catctagcac gcgggacgcg gaaaccgtat ggagaaaaca cctacaaccc
1081 cggccggacg gtggtttcg gccacactta ggggtcgggt gcctgcttgc cgggcagggc
1141 agtcccgggg tgctgtggtg cgggcgggag ggctgtcgct tcgaggtgtg ccggcgggac
1201 actccgggcc tcagccgtac ccgcaacggg gacagttctc ctcccttccg ggctggatgg
1261 tcccttcccc cgaaatgcgg cgagatctcc cagtcagccc ggaaaacacc cgctgtgccc
1321 aggtactctt tgcttcgaac agacaggccg gacggtccac gggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agacgctgtg gcgcatgtgg
1501 tgtgaggcca cccaggactg gtgcctgggg gtgccggtcg actccgcgg acagcctgcg
1561 gaggacggcg agttctgct gctttctccg gtccaggcag cgacctgggg gaactattac
1621 gcgctcgggg attcgtactc ttcgggggac ggggcccgcg actactatcc cggcaccgcg
1681 gtgaagggcg gttgctggcg gtccgctaac gcctatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact cccctcacac gtcgctggtg
1861 acgatcggga tcggcggcaa cgatctgggg ttctccacgg ttttgaagac ctgcatggtg
1921 cgggtgccgc tgctggacag caaggcgtgc acggaccagg aggacgctat ccgcaagcgg
1981 atggcgaaat tcgagacgac gtttgaagag ctcatcagcg aagtgcgcac ccgcgcgccg
2041 gacgcccgga tccttgtcgt gggctacccc cggattttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacagagat cggctcggac
2281 gagccgtggg tgaacggggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gcccgggccg tccgctctat gccactttcg cggtggtggc gggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcgttg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacgggggcg agggcgcgga catggtccag gtaagggccc tgcggacga ggctcaccac
2821 ggcagtgccg accgcgcagg cgagggcgtt gccgccgaag gtgctgccgt gctggccggg
2881 gcggatcacg tcgaagactt ccgcgtcgcc taccgccgcc gccacgggca ggatgccgcc
2941 gcccagcgct ttgccgaaca ggtagatatc ggcgtcgact ccgctgtggt cgcaggcccg
```

FIGURE 50

(SEQ ID No. 40)

```
  1 vgsgpraatr rriflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 51

(SEQ ID No. 41)

```
  1 mrttviaasa lllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 52

(SEQ ID No. 42)

```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggc ggcgggctct gtggtgcccc gcgacccccg
 181 gccccggtga gcggtgaatg aaatccggct gtaatcagca tcccgtgccc accccgtcgg
 241 ggaggtcagc gcccggagtg tctacgcagt cggatcctct cggactcggc catgctgtcg
 301 gcagcatcgc gctcccgggt cttggcgtcc ctcggctgtt ctgcctgctg tccctggaag
 361 gcgaaatgat caccggggag tgatacaccg tggtctcat cccggatgcc cacttcggcg
 421 ccatccggca attcgggcag ctccgggtgg aagtaggtgg catccgatgc gtcggtgacg
 481 ccatagtggg cgaagatctc atcctgctcg agggtgctca ggccactctc cggatcgata
 541 tcgggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aatgggtgg tgggagccct ggtcgcggtt
 961 ccgtgggagg cgccgtgccc cgcaggatc tcggcatcgg cggatctggc cggtaccccg
1021 cggtgaataa aatcattctg taaccttcat cacggttggt tttaggtatc cgcccctttc
1081 gtcctgaccc cgtccccggc gcgcgggagc ccgcggttg cggtagacag gggagacgtg
1141 gacaccatga ggacaacggt catcgcagca agcgcattac tccttctcgc cggatgcgcg
1201 gatgggccc ggaggagac cgccggtgca ccgccgggtg agtcctccgg gggcatccgg
1261 gaggagggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg ccaggggggcg
1441 gtgaccgggg atctgctcga acccaggacg ctggggagc gcacgctgcc ggcgcaggtg
1501 gatgcgctga cggaggacac caccctggtc accctctcca tcggggggcaa tgacctcgga
1561 ttcggggagg tggcgggatg catccgggaa cggatcgccg gggagaacgc tgatgattgc
1621 gtggacctgc tggggaaac catcggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactggggg atgtctccga ggcggatcgt
1801 cgttgggcgg ttgagctgac cgggcagatc aacgagaccg tgcgcgaggc ggccgaacga
1861 cacgatgccc tctttgtcct gcccgacgat gccgatgagc acaccagttg tgcaccccca
1921 cagcagcgct gggcggatat ccagggccaa cagaccgatg cctatccgct gcacccgacc
1981 tccgccggcc atgaggcgat ggccgccgcc gtccgggacg cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaaggggttg ttccccgagg gtgcgcagag ccgagtccag
2221 acctgcggcc tgctccggat catgggccca accggcgatg acgatcaaca cccccaggat
2281 cccgaaggcg ataccacggg cgacataacc ggctgttccg gtgatgatga tcgcggtccc
2341 gacctgccct gaccccgcac ccgcctccag atcctcccgg aaatcccggg tggcccctt
2401 ccagaggttg tagacacccg ccccagtac caccagcccg gcgaccacaa ccagcaccac
2461 accccaggt tgggatagga cggtggcgt gacatcggtg gcggtctccc catcggaggt
2521 gctgccgccc cgggcgaagg tggaggtggt caccgccagg gagaagtaga ccatggccat
2581 gaccgccccc ttggcccttt ccttgaggtc ctcgcccgcc agcagctggc tcaattgcca
2641 gagtcccagg gccgccaggg cgatgacggc aaccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatgccca ggacaatgaa
2821 accacctctg gccagggtgg tcagcgcggg gtggtcctcg gccggtcgg cagccgttc
2881 gatcgtccgt ttcgcggatc tggtgtcgcc cttatccata gctcccattg aaccgccttg
2941 agggggtgggc ggccactgtc agggcggatt gtgatctgaa ctgtgatgtt ccatcaaccc
```

FIGURE 53

(SEQ ID No. 43)

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
```

Figure 54

(SEQ ID No. 44)

```
   1 cccggcggcc cgtgcaggag cagcagccgg cccgcgatgt cctcgggcgt cgtcttcatc
  61 aggccgtcca tcgcgtcggc gaccggcgcc gtgtagttgg cccggacctc gtcccaggtg
 121 cccgcggcga tctggcgggt ggtgcggtgc gggccgcgcc gaggggagac gtaccagaag
 181 cccatcgtca cgttctccgg ctgcggttcg ggctcgtccg ccgctccgtc cgtcgcctcg
 241 ccgagcacct tctcggcgag gtcggcgctg gtcgccgtca ccgtgacgtc ggcgccccgg
 301 ctccagcgcg agatcagcag cgtccagccg tcgccctccg ccagcgtcgc gctgcggtcg
 361 tcgtcgcggg cgatccgcag cacgcgcgcg ccggcggca gcagcgtggc gccggaccgt
 421 acgcggtcga tgttcgccgc gtgcgagtac ggctgctcac ccgtggcgaa acggccgagg
 481 aacagcgcgt cgacgacgtc ggacggggag tcgctgtcgt ccacgttgag ccggatcggc
 541 agggcttcgt gcgggttcac ggacatgtcg ccatgatcgg gcacccggcc gccgcgtgca
 601 cccgctttcc cgggcacgca cgacaggggc tttctcgccg tcttccgtcc gaacttgaac
 661 gagtgtcagc catttcttgg catggacact tccagtcaac gcgcgtagct gctaccacgg
 721 ttgtggcagc aatcctgcta agggaggttc catgagacgt ttccgacttg tcggcttcct
 781 gagttcgctc gtcctcgccg ccggcgccgc cctcaccggg gcagcgaccg cccaggcggc
 841 ccaacccgcc gccgccgacg gctatgtggc cctcggcgac tcctactcct ccggggtcgg
 901 agcgggcagc tacatcagct cgagcggcga ctgcaagcgc agcacgaagg cccatcccta
 961 cctgtgggcg gccgcccact cgccctccac gttcgacttc accgcctgtt ccggcgcccg
1021 tacgggtgat gttctctccg gacagctcgg cccgctcagc tccggcaccg gcctcgtctc
1081 gatcagcatc ggcggcaacg acgccggttt cgccgacacc atgacgacct gtgtgctcca
1141 gtccgagagc tcctgcctgt cgcggatcgc caccgccgag gcgtacgtcg actcgacgct
1201 gcccggcaag ctcgacggcg tctactcggc aatcagcgac aaggcgccga acgcccacgt
1261 cgtcgtcatc ggctacccgc gcttctacaa gtcggcacc acctgcatcg gcctgtccga
1321 gaccaagcgg acggcgatca acaaggcctc cgaccacctc aacaccgtcc tcgcccagcg
1381 cgccgccgcc cacggcttca ccttcggcga cgtacgcacc accttcaccg ccacgagct
1441 gtgctccggc agccctggc tgcacagcgt caactggctg aacatcggcg agtcgtacca
1501 ccccaccgcg gccggccagt ccggtggcta cctgccggtc ctcaacggcg ccgcctgacc
1561 tcaggcggaa ggagaagaag aaggagcgga gggagacgag gagtgggagg ccccgcccga
1621 cggggtcccc gtcccgtct ccgtctccgt cccggtcccg caagtcaccg agaacgccac
1681 cgcgtcggac gtgcccgca ccggactccg cacctccacg cgcacggcac tctcgaacgc
1741 gccggtgtcg tcgtgcgtcg tcaccaccac gccgtcctgg cgcgagcgct gccgcccga
1801 cgggaaggac agcgtccgcc accccggatc ggagaccgac ccgtccgcgg tcacccaccg
1861 gtagccgacc tccgcgggca gccgcccgac cgtgaacgtc gccgtgaacg cgggtgcccg
1921 gtcgtgcggc ggcggacagg ccccgagta gtgggtgcgc gagcccacca cggtcacctc
1981 caccgactgc gctgcggggc
```

FIGURE 55

(SEQ ID No. 45)

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

FIGURE 56

SEQ ID No. 46

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagccgg tgccttctt gagcgtgacg atgtagctgc
 181 ccttgatcgc ggtgggggag ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctgggtg gggcgcacgg ctgtgggggg tgcgcgcgtc atcacgcaca cggccctgga
 421 gcgtcgtgtt ccgccctggg ttgagtaaag cctcggccat ctacggggt ggctcaaggg
 481 agttgagacc ctgtcatgag tctgacatga gcacgcaatc aacggggccg tgagcacccc
 541 ggggcgaccc cggaaagtgc cgagaagtct tggcatggac acttcctgtc aacacgcgta
 601 gctggtacga cggttacggc agagatcctg ctaaagggag gttccatgag acgttcccga
 661 attacggcat acgtgacctc actcctcctc gccgtcggct gcgccctcac cggggcagcg
 721 acggcgcagg cgtccccagc cgccgcggcc acgggctatg tggccctcgg cgactcgtac
 781 tcgtccggtg tcggcgccgg cagctaccctc agctccagcg gcgactgcaa gcgcagttcg
 841 aaggcctatc cgtacctctg gcaggccgcg cattcaccct cgtcgttcag tttcatggct
 901 tgctcgggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgccggg ccaactcgac agcgtgtaca cggcgatcag cacgaaggcc
1141 ccgtcggccc atgtggccgt gctgggctac ccccgcttct acaaactggg cggctcctgc
1201 ctcgcgggcc tctcggagac caagcggtcc gccatcaacg acgcggccga ctatctgaac
1261 agcgccatcg ccaagcgcgc cgccgaccac ggcttcacct tcggcgacgt caagagcacc
1321 ttcaccggcc atgagatctg ctccagcagc acctggctgc acagtctcga cctgctgaac
1381 atcggccagt cctaccaccc gaccgcggcc ggccagtccg gcggctatct gccggtcatg
1441 aacagcgtgg cctgagctcc cacggcctga attttaaggg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga acacctgctt ctgctgggtc tttccgccgc
1681 tcgccgggaa ggacagcgtc ttccagcccg gatccgggac ctcgcccttc ttggtcaccc
1741 agcggtactc cacctcgacc ggcacccggc ccaccgtgaa ggtcgccgtg aacgtgggcg
1801 cctgggcggt gggcggcggg caggcaccgg agtagtcggt gtgcacgccg gtgaccgtca
1861 ccttcacgga ctgggccggc ggggtcgtcg taccgccgcc gccaccgccg cctccggag
1921 tggagcccga gctgtggtcg ccccgccgt cggcgttgtc gtcctcgggg gttttcgaac
```

FIGURE 57

SEQ ID No. 47

1 mgsgpraatr rrlfigipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg

FIGURE 58

SEQ ID No. 48

| 1 | ctgcagacac ccgccccgcc ttctcccgga tcgtcatgtt cggcgactcc ctcagcgaca |
| 61 | ccggcaagat gtactccaag atgcgcggct acctgccgtc ctccccgccg tactacgagg |
| 121 | gccgcttctc gaacggcccg gtctggctgg agcagctgac gaagcagttc cccggcctga |
| 181 | cgatcgccaa cgaggccgag ggggcgcga ccgcagtcgc ctacaacaag atctcctgga |
| 241 | acccgaagta ccaggtcatt aacaacctcg actacgaggt cacccagttc ttgcagaagg |
| 301 | actcgttcaa gcccgacgac ctggtcatcc tgtgggtggg cgccaacgac tacctggcct |
| 361 | acggttggaa cacggagcag gacgccaagc gggtgcgcga cgccatctcg gacgcggcaa |
| 421 | accgcatggt cctgaacggc gcgaagcaga tcctgctgtt caacctgccc gacctgggcc |
| 481 | agaaccccgtc cgcccgctcc cagaaggtcg tcgaggccgt ctcgcacgtg tccgcctacc |
| 541 | acaacaagct gctcctcaac ctcgcccggc agctcgcccc gacgggcatg gtcaagctgt |
| 601 | tcgagatcga caagcagttc gcggagatgc tgcgcgaccc ccagaacttc ggcctgagcg |
| 661 | acgtggagaa cccgtgctac gacggcggct acgtgtggaa gccgttcgcc acccggtccg |
| 721 | tctcgaccga ccggcagctg tcggccttct cgccccagga gcgcctggcg atcgctggca |
| 781 | accccgctcct ggcacaggcg gtagcttcgc cgatggcccg ccgctcggcc tcgcccctca |
| 841 | actgcgaggg caagatgttc tgggaccagg tccaccccac caccgtggtc cacgccgcc |
| 901 | tctcggagcg cgccgccacc ttcatcgaga cccagtacga gttcctcgcc cactagtcta |
| 961 | gaggatcc |

Figure 61
1. L131
2. S.avermitilis
3. T.fusca
4. Consensus

```
                    1                                                50
1    (1)   --------MRLTRSLSAASVIVFALLLALLGISPAQAAG-----------
2    (1)   --------MRRSRITAYVTSLLLAVGCALTGAATAQASPA----------
3    (1)   VGSGPRAATRRRLFLGIPALVLVTALTLVLAVPTGRETLWRMWCEATQDW
4    (1)           MRRSRFLA  ALILLTLA  AL GAA  ARAAP 51                                               100
1   (32)   ---------------------------P-AYVA LGDSYS SGNGAGSYID
2   (33)   -------------------------AAATGYVA LGDSYS SGVGAGSYLS
3   (51)   CLGVPVDSRGQPAEDGEFLLLSPVQAATWGNYYA LGDSYS SGDGARDYYP
4   (51)                            A  A  YVA LGDSYS SG GAGSY 101                                               150
1   (53)   SSGD---CHRSNNAYPARWAAANAP---SSFTFAACSGAVTTDVIN----
2   (57)   SSGD---CKRSSKAYPYLWQAAHSP---SSFSFMACSGARTGDVLA----
3   (101)  GTAVKGGCWRSANAYPELVAEAYDFA--GHLSFLACSGQRGYAMLDAIDE
4   (101)  SSGD   C RSTKAYPALWAAAHA    SSFSF ACSGARTYDVLA 151                                               200
1   (93)   --NQLGALNAST--GLVSI IGGNDAG FADAMTTCVTS------SDSTCL
2   (97)   --NQLGTLNSST--GLVSL IGGNDAG FSDVMTTCVLQ------SDSACL
3   (149)  VGSQLDWNSPHT--SLVTI IGGNDLG FSTVLKTCMVR------VPLLDS
4   (151)       QL  LNS T   LVSI IGGNDAG FAD MTTCVL      SDSACL 201                                               250
1   (133)  NRLATATNYINTTLLA-------RLDAVYSQIKARAPNARVVVLGYPRMY
2   (137)  SRINTAKAYVDSTLPG-------QLDSVYTAISTKAPSAHVAVLGYPRFY
3   (191)  KACTDQEDAIRKRMAKF----ETTFEELISEVRTRAPDARILVVGYPRIF
4   (201)       RIA AK YI  TLPA       RLDSVYSAI TRAP ARVVVLGYPRIY 251                                               300
1   (176)  LASNPWYCLGLSNTKRAAINTTADTLNSVISSRATAH-----------GF
2   (180)  KLGG-SCLAGLSETKRSAINDAADYLNSAIAKRAADH-----------GF
3   (237)  PEEPTGAYYTLTASNQRWLNETIQEFNQQLAEAVAVHDEEIAASGGVGSV
4   (251)       SG    LGLS TKRAAINDAAD LNSVIAKRAADH           GF 301                                               350
1   (215)  RFGDVRPTFNNHELFFGNDWLHSLTLP----------------VWES YH
2   (218)  TFGDVKSTFTGHEICSSSTWLHSLDLLN---------------IGQS YH
3   (287)  EFVDVYHALDGHEIGSDEPWVNGVQLRDLATG---------VTVDRST FH
4   (301)  TFGDV   TF GHELCSA PWLHSLTLP              V   S YH 351                                               395
1   (248)  PTSTGHQSGYLPVLNANSST---------------------
2   (252)  PTAAGQSGGYLPVMNSVA-----------------------
3   (328)  PNAAGHRAVGERVIEQIETGPGRPLYATFAVVAGATVDTLAGEVG
4   (351)  PTA  GHAAGYLPVLNSI T
```

ENZYMATIC OIL-DEGUMMING METHOD

REFERENCE TO RELATED APPLICATIONS

This application is a continuation-in-part of International Patent Application PCT/GB2005/002823 filed Jul. 18, 2005 which published as WO 2006/008508 on Jan. 26, 2006, and which claims priority to Great Britain Patent Application Nos. 0513859.9 filed Jul. 7, 2005 and 0416035.4 filed Jul. 16, 2004, and to U.S. Patent Application No. 60/591,185 filed Jul. 26, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

REFERENCE TO RELATED APPLICATIONS

Reference is made to the following related applications: U.S. application Ser. No. 09/750,990 filed on 20 Jul. 1999, U.S. application Ser. No. 10/409,391, WO2004/064537, WO2004/064987, PCT/IB2004/004378 and PCT/IB2004/004374. Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference.

FIELD OF INVENTION

The present invention relates to a method for enzymatically degumming edible oils using a lipid acyltransferase.

The present invention further relates to one or more lipid acyltransferases.

The present invention yet further relates to the use of a lipid acyltransferase to the degumming of edible oils.

TECHNICAL BACKGROUND

Traditionally two processes have been used for degumming of oil which are the physical degumming and the chemical degumming processes. Back in the 1990's the enzymatic degumming process was developed based on the use of pancreatic phospholipase. Because this enzyme was non-kosher the phospholipase was eventually substituted by a microbial phospholipase A1 (Lecitase Ultra™—Novozymes, Denmark). The enzymatic process has several advantages over the chemical or the physical degumming processes including cost savings, higher yield and a more environmentally friendly process.

SUMMARY ASPECTS OF THE PRESENT INVENTION

In one aspect, the present invention provides a method for the enzymatic degumming of vegetable oils or edible oils using a lipid acyltransferase as defined herein.

The present invention also provides a process of enzymatic degumming of vegetable or edible oils, comprising treating the edible or vegetable oil with a lipid acyl transferase according to the present invention so as to remove a major part of the phospholipid.

The present invention also provides a process of enzymatic degumming of vegetable or edible oils, comprising treating the edible or vegetable oil with a lipid acyl transferase according to the present invention so as to transfer an acyl group from a major part of the phospholipid to one or more acyl acceptors, for example to one or more sterols and/or stanols.

In another aspect, the present invention provides one or more lipid acyltransferases.

In one aspect, the present invention provides a lipid acyltransferase comprising the amino acid sequence shown as SEQ ID No. 16.

In another aspect, the present invention provides a lipid acyltransferase comprising the amino acid sequence shown as SEQ ID No. 16, or an amino acid sequence which has 75% or more, preferably 85% or more, more preferably 90% or more, even more preferably 95% or more, even more preferably 98% or more, or even more preferably 99% or more identity to SEQ ID No. 16.

In a yet further aspect, the present invention provides the use of a lipid acyltransferase in the degumming of edible oils (i) to remove phospholipids (such as phosphatidylcholine) and/or (ii) to increase the formation of sterol esters and/or stanol esters in the oil and/or (iii) to remove phospholipids (such as phosphatidylcholine) and/or to increase the formation of sterol esters and/or stanol esters in the oil without significantly increasing free fatty acids in the oil.

Preferable Aspects

The lipid acyltransferase for use in the present invention may be a natural lipid acyltransferase or may be a variant lipid acyltransferase.

For instance, the lipid acyltransferase for use in the method and uses of the present invention may be one as described in WO2004/064537 or WO2004/064987, or PCT/1132004/004378 or GB0513859.9, for example. The term "lipid acyltransferase" as used herein means an enzyme that has acyltransferase activity (generally classified as E.C. 2.3.1.x), whereby the enzyme is capable of transferring an acyl group from a lipid to one or more acceptor substrates, such as one or more of the following: a sterol; a stanol; a carbohydrate; a protein; a protein subunit; glycerol—preferably a sterol and/or a stanol.

Preferably, the lipid acyltransferase according to the present invention or for use in the methods and/or uses of the present invention is capable of transferring an acyl group from a lipid (as defined herein) to one or more of the following acyl acceptor substrates: a sterol or a stanol, preferably a sterol.

For some aspects the "acyl acceptor" according to the present invention may be any compound comprising a hydroxy group (—OH), such as for example, polyvalent alcohols, including glycerol; sterols; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water.

The acyl acceptor is preferably not a monoglyceride.

In one aspect, the lipid acyltransferase according to the present invention or for use in the methods and/or uses of the present invention may, as well as being able to transfer an acyl group from a lipid to a sterol and/or a stanol, additionally be able to transfer the acyl group from a lipid to one or more of the following: a carbohydrate, a protein, a protein subunit, glycerol.

Preferably, the lipid substrate upon which the lipid acyltransferase according to the present invention acts is one or more of the following lipids: a phospholipid, such as a lecithin, e.g. phosphatidylcholine.

This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the lipid substrate upon which the lipid acyltransferase according to the present invention or for use in the method and/or uses of the present invention acts as a phospholipid, such as lecithin, for example phosphatidylcholine.

For some aspects, preferably the lipid acyltransferase according to the present invention or for use in the method and/or uses of the present invention is incapable, or substantially incapable, of acting on a triglyceride and/or a 1-monoglyceride and/or 2-monoglyceride.

Suitably, the lipid acyltransferase according to the present invention or for use in the method and/or uses of the present invention may exhibit one or more of the following phospholipase activities: phospholipase A2 activity (E.C. 3.1.1.4) or phospholipase A1 activity (E.C. 3.1.1.32).

Suitably, for some aspects the lipid acyltransferase according to the present invention or for use in the method and/or uses of the present invention may be capable of transferring an acyl group from a phospholipid to a sterol and/or a stanol.

For some aspects, preferably the lipid acyltransferase according to the present invention or for use in methods and/or uses of the present invention is capable of transferring an acyl group from a phospholipid to a sterol and/or a stanol to form at least a sterol ester and/or a stanol ester.

For some aspects, preferably the lipid acyltransferase according to the present invention or for use in the method and/or uses of the present invention does not exhibit triacylglycerol lipase activity (E.C. 3.1.1.3) or does not exhibit significant triacylglycerol lipase activity (E.C. 3.1.1.3).

The lipid acyltransferase according to the present invention or for use in the method and/or uses of the present invention may be capable of transferring an acyl group from a lipid to a sterol and/or a stanol. Thus, in one embodiment the "acyl acceptor" according to the present invention may be either a sterol or a stanol or a combination of both a sterol and a stanol.

Preferably, the lipid acyltransferase enzyme according to the present invention or for use in methods and uses of the present invention may be characterised using the following criteria:

(i) the enzyme possesses acyl transferase activity which may be defined as ester transfer activity whereby the acyl part of an original ester bond of a lipid acyl donor is transferred to an acyl acceptor to form a new ester; and (ii) the enzyme comprises the amino acid sequence motif GDSX, wherein X is one or more of the following amino acid residues L, A, V, I, F, Y, H, Q, T, N, M or S.

Preferably, X of the GDSX motif is L or Y. More preferably, X of the GDSX motif is L. Thus, preferably the enzyme according to the present invention comprises the amino acid sequence motif GDSL.

The GDSX motif is comprised of four conserved amino acids. Preferably, the serine within the motif is a catalytic serine of the lipid acyltransferase enzyme. Suitably, the serine of the GDSX motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX motif according to the present invention, the sequence is preferably compared with the hidden markov model profiles (HMM profiles) of the pfam database in accordance with the procedures taught in WO2004/064537 or WO2004/064987.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft D H (2002) Brief Bioinform 3; 236-245.

http:/www.nbi.nlm.nih.gov/entrez/query.fcgi?cmd=
Retrieve&db=PubMed&list_uids=12230032&dopt=
Abstract http://www.ncbi.nlm.nih.gov/entrez/query.fcgi?cmd=
Retrieve&db=PubMed&list_uids=11752314&dopt=
Abstract For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located at the following websites.

http://www.sanger.ac.uk/Software/Pfam/index.shtml
http://pfam.wustl.edu/
http://pfam.jouy.inra.fr/
http://pfam.cgb.ki.se/

The database offers a search facility where one can enter a protein sequence. Using the default parameters of the database the protein sequence will then be analysed for the presence of Pfam domains. The GDSX domain is an established domain in the database and as such its presence in any query sequence will be recognised. The database will return the alignment of the Pfam00657 consensus sequence to the query sequence.

Preferably the lipid acyltransferase enzyme for use in methods and uses of the invention can be aligned using the Pfam00657 consensus sequence (for a full explanation see WO2004/064537 or WO2004/064987).

Preferably, a positive match with the hidden markov model profile (HMM profile) of the pfam00657 domain family indicates the presence of the GDSL or GDSX domain according to the present invention.

Preferably when aligned with the Pfam00657 consensus sequence the lipid acyltransferase for use in the methods or uses of the invention may have at least one, preferably more than one, preferably more than two, of the following, a GDSx block, a GANDY block, a HPT block. Suitably, the lipid acyltransferase may have a GDSx block and a GANDY block. Alternatively, the enzyme may have a GDSx block and a HPT block. Preferably the enzyme comprises at least a GDSx block.

Preferably, residues of the GANDY motif are selected from GANDY, GGNDA, GGNDL, most preferably GANDY.

Preferably, when aligned with the Pfam00657 consensus sequence the enzyme for use in the methods or uses of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 1: 28hid, 29hid, 30hid, 31hid, 32gly, 33Asp, 34Ser, 35hid, 130hid, 131Gly, 132Hid, 133Asn, 134Asp, 135hid, 309His.

The pfam00657 GDSX domain is a unique identifier which distinguishes proteins possessing this domain from other enzymes.

The pfam00657 consensus sequence is presented in FIG. 12 as SEQ ID No. 2. This is derived from the identification of the pfam family 00657, database version 6, which may also be referred to as pfam00657.6 herein.

The consensus sequence may be updated by using further releases of the pfam database (for example see WO2004/064537 or WO2004/064987).

The presence of the GDSx, GANDY and HPT blocks are found in the pfam family 00657 from both releases of the database. Future releases of the pfam database can be used to identify the pfam family 00657.

In one embodiment, the lipid acyltransferase enzyme for use in methods and uses of the present invention may be characterised using the following criteria:
 (i) the enzyme possesses acyl transferase activity which may be defined as ester transfer activity whereby the acyl part of an original ester bond of a lipid acyl donor is transferred to acyl acceptor to form a new ester;
 (ii) the enzyme comprises the amino acid sequence motif GDSX, wherein X is one or more of the following amino acid residues L, A, V, I, F, Y, H, Q, T, N, M or S.;
 (iii) the enzyme comprises His-309 or comprises a histidine residue at a position corresponding to His-309 in the *Aeromonoas hydrophila* lipid acyltransferase enzyme shown in FIGS. 11 and 13 (SEQ ID No. 1 or SEQ ID No. 3).

Preferably, the amino acid residue of the GDSX motif is L.

In SEQ ID No. 3 or SEQ ID No. 1 the first 18 amino acid residues form a signal sequence. His-309 of the full length sequence, that is the protein including the signal sequence, equates to His-291 of the mature part of the protein, i.e. the sequence without the signal sequence.

In one embodiment, the lipid acyltransferase enzyme for use in methods and uses of the present invention comprises the following catalytic triad: Ser-34, Asp-134 and His-309 or comprises a serine residue, an aspartic acid residue and a histidine residue, respectively, at positions corresponding to Ser-34, Asp-134 and His-309 in the *Aeromonas hydrophila* lipid acyltransferase enzyme shown in FIG. 13 (SEQ ID No. 3) or FIG. 11 (SEQ ID No. 1). As stated above, in the sequence shown in SEQ ID No. 3 or SEQ ID No. 1 the first 18 amino acid residues form a signal sequence. Ser-34, Asp-134 and His-309 of the full length sequence, that is the protein including the signal sequence, equate to Ser-16, Asp-116 and His-291 of the mature part of the protein, i.e. the sequence without the signal sequence. In the pfam00657 consensus sequence, as given in FIG. 12 (SEQ ID No. 2) the active site residues correspond to Ser-7, Asp-157 and His-348.

In one embodiment, the lipid acyltransferase enzyme for use in methods and uses of the present invention may be characterised using the following criteria:
 (i) the enzyme possesses acyl transferase activity which may be defined as ester transfer activity whereby the acyl part of an original ester bond of a first lipid acyl donor is transferred to an acyl acceptor to form a new ester; and
 (ii) the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-134 and His-309, respectively, in the *Aeromonas hydrophila* lipid acyltransferase enzyme shown in FIG. 13 (SEQ ID No. 3) or FIG. 11 (SEQ ID No. 1).

Suitably, the lipid acyltransferase enzyme for use in methods and uses of present invention comprises one or more of the following amino acid sequences:
 (i) the amino acid sequence shown as SEQ ID No. 3 (see FIG. 13)
 (ii) the amino acid sequence shown as SEQ ID No. 4 (see FIG. 14)
 (iii) the amino acid sequence shown as SEQ ID No. 5 (see FIG. 15)
 (iv) the amino acid sequence shown as SEQ ID No. 6 (see FIG. 16)
 (v) the amino acid sequence shown as SEQ ID No. 7 (see FIG. 17)
 (vi) the amino acid sequence shown as SEQ ID No. 8 (see FIG. 18)
 (vii) the amino acid sequence shown as SEQ ID No. 9 (FIG. 19)
 (viii) the amino acid sequence shown as SEQ ID No. 10 (FIG. 20)
 (ix) the amino acid sequence shown as SEQ ID No. 11 (FIG. 21)
 (x) the amino acid sequence shown as SEQ ID No. 12 (FIG. 22)
 (xi) the amino acid sequence shown as SEQ ID No. 13 (FIG. 23)
 (xii) the amino acid sequence shown as SEQ ID No. 14 (FIG. 24)

(xiii) the amino acid sequence shown as SEQ ID No. 1 (FIG. 11)
(xiv) the amino acid sequence shown as SEQ ID No. 15 (FIG. 25) or
an amino acid sequence which has 75% or more identity with any one of the sequences shown as SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, or SEQ ID No. 15.

Suitably, the lipid acyltransferase enzyme for use in methods and uses of the present invention comprises either the amino acid sequence shown as SEQ ID No. 3 or as SEQ ID No. 4 or SEQ ID No. 1 or SEQ ID No. 15 or comprises an amino acid sequence which has 75% or more, preferably 80% or more, preferably 85% or more, preferably 90% or more, preferably 95% or more, identity with the amino acid sequence shown as SEQ ID No. 3 or the amino acid sequence shown as SEQ ID No. 4 or the amino acid sequence shown as SEQ ID No. 1 or the amino acid sequence shown as SEQ ID No. 15.

Suitably the lipid acyltransferase enzyme for use in methods and uses of the present invention comprises an amino acid sequence which has 80% or more, preferably 85% or more, more preferably 90% or more and even more preferably 95% or more identity with any one of the sequences shown as SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, or SEQ ID No. 15.

Suitably, the lipid acyltransferase enzyme for use in methods and uses of the present invention comprises one or more of the following amino acid sequences:
(a) an amino acid sequence shown as amino acid residues 1-100 of SEQ ID No. 3 or SEQ ID No. 1;
(b) an amino acid sequence shown as amino acids residues 101-200 of SEQ ID No. 3 or SEQ ID No. 1;
(c) an amino acid sequence shown as amino acid residues 201-300 of SEQ ID No. 3 or SEQ ID No. 1; or
(d) an amino acid sequence which has 75% or more, preferably 85% or more, more preferably 90% or more, even more preferably 95% or more identity to any one of the amino acid sequences defined in (a)-(c) above.

Suitably, the lipid acyltransferase enzyme for use in methods and uses of the present invention comprises one or more of the following amino acid sequences:
(a) an amino acid sequence shown as amino acid residues 28-39 of SEQ ID No. 3 or SEQ ID No. 1;
(b) an amino acid sequence shown as amino acids residues 77-88 of SEQ ID No. 3 or SEQ ID No. 1;
(c) an amino acid sequence shown as amino acid residues 126-136 of SEQ ID No. 3 or SEQ ID No. 1;
(d) an amino acid sequence shown as amino acid residues 163-175 of SEQ ID No. 3 or SEQ ID No. 1;
(e) an amino acid sequence shown as amino acid residues 304-311 of SEQ ID No. 3 or SEQ ID No. 1; or
(f) an amino acid sequence which has 75% or more, preferably 85% or more, more preferably 90% or more, even more preferably 95% or more identity to any one of the amino acid sequences defined in (a)-(e) above.

In one aspect, the lipid acyltransferase for use in the method and uses of the present invention may be the lipid acyl transferase from *Candida parapsilosis* as taught in EP 1 275 711. Thus in one aspect the lipid acyltransferase for use in the method and uses of the present invention may be a lipid acyltransferase comprising one of the amino acid sequences taught in SEQ ID No. 17 (FIG. 28) or SEQ ID No. 18 (FIG. 29).

Much by preference, the lipid acyltransferase for use in the method and uses of the present invention may be a lipid acyltransferase comprising the amino acid sequence shown as SEQ ID No. 16 (FIG. 10), or an amino acid sequence which has 75% or more, preferably 85% or more, more preferably 90% or more, even more preferably 95% or more, even more preferably 98% or more, or even more preferably 99% or more identity to SEQ ID No. 16. This enzyme could be considered a variant enzyme.

In one aspect, the lipid acyltransferase for use in the methods and uses of the present invention may be a lecithin: cholesterol acyltransferase (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme for use in the methods and uses of the present invention may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of patent Procedure at the National Collection of Industrial, Marine and Food Bacteria (NCIMB) 23 St. Machar Street, Aberdeen Scotland, GB on 22 Dec. 2003 under accession numbers NICMB 41204 and NCIMB 41205, respectively.

Highly preferred lipid acyl transferases for use in the methods of the invention include those isolated from *Aeromonas* spp., preferably *Aeromonas hydrophila* or *A. salmonicida*, most preferable *A. salmonicida*. Most preferred lipid acyl transferases for use in the present invention are encoded by SEQ ID Nos. 1, 3, 4, 15, 16. It will be recognised by the skilled person that it is preferable that the signal peptides of the acyl transferase has been cleaved during expression of the transferase. The signal peptide of SEQ ID 1, 3, 4, 15 and 16 are amino acids 1-18. Therefore the most preferred regions are amino acids 19-335 for SEQ ID No. 1 and SEQ ID No. 3 (*A. hydrophilia*) and amino acids 19-336 for SEQ ID No. 4, SEQ ID No. 15 and SEQ ID No. 16. (*A. salmonicida*). When used to determine the homology of identity of the amino acid sequences, it is preferred that the alignments as herein described use the mature sequence.

Therefore the most preferred regions for determining homology (identity) are amino acids 19-335 for SEQ ID No. 1 and 3 (*A. hydrophilia*) and amino acids 19-336 for SEQ ID Nos. 4, 15 and 16. (*A. salmonicida*). SEQ ID 34 and 35 are mature protein sequences of the highly preferred lipid acyl transferases from *A. hzydrophilia* and *A. salmonicida* respectively.

A lipid acyl transferase for use in the invention may also be isolated from *Thermobifida*, preferably *T. fusca*, most preferably that encoded by SEQ ID No. 28.

A lipid acyl transferase for use in the invention may also be isolated from *Streptomyces*, preferable *S. avermitis*, most preferably that encoded by SEQ ID No. 32. Other possible enzymes for use in the present invention from *Streptomyces* include those encoded by SEQ ID No.s 5, 6, 9, 10, 11, 12, 13, 14, 31, 33. The examples show that the enzyme encoded by SEQ ID No. 33 is highly effective in enzymatic degumming.

An enzyme for use in the invention may also be isolated from *Corynebacterium*, preferably *C. efficiens*, most preferably that encoded by SEQ ID No. 29.

Suitably, the lipid acyltransferase for use in the methods and uses according to the present invention may be a lipid acyltransferase comprising any one of the amino acid sequences shown as SEQ ID No.s 37, 38, 40, 41, 43, 45, or 47 or an amino acid sequence which has at least 70%, 75%, 80%, 85%, 90%, 95%, 96%, 97% or 98% identity therewith, or encoded by any one of the nucleotide sequences shown as SEQ ID No.s 36, 39, 42, 44, 46, or 48 or a nucleotide sequence which has at least 70%, 75%, 80%, 85%, 90%, 95%, 96%, 97% or 98% identity therewith.

Preferably, the lipid acyltransferase for use in the methods and uses according to the present invention is a lipid acyltransferase capable of hydrolysing at least galactolipids and/or capable of transferring an acyl group from at least a galactolipid to one or more acyl acceptor substrates, wherein the enzyme is obtainable, preferably obtained, from *Streptomyces* species.

In one embodiment the lipid acyltransferase for use in the methods and uses according to the present invention is preferably a lipid acyltransferase capable of hydrolysing at least galactolipids and/or capable of transferring an acyl group from at least a galactolipid to one or more acyl acceptor substrates, wherein the enzyme is encoded by a nucleic acid selected from the group consisting of:
 a) a nucleic acid comprising a nucleotide sequence shown in SEQ ID No. 36;
 b) a nucleic acid which is related to the nucleotide sequence of SEQ ID No. 36 by the degeneration of the genetic code; and
 c) a nucleic acid comprising a nucleotide sequence which has at least 70% identity with the nucleotide sequence shown in SEQ ID No. 36.

In one embodiment, the lipid acyltransferase for use in the methods and uses according to the present invention is preferably a lipid acyltransferase comprising an amino acid sequence as shown in SEQ ID No. 37 or an amino acid sequence which has at least 60% identity thereto.

In another embodiment the lipid acyltransferase for use in the methods and uses according to the present invention is preferably a lipid acyltransferase capable of hydrolysing at least a galactolipid and/or capable of transferring an acyl group from at least a galactolipid to one or more acyl acceptor substrates, wherein the enzyme comprises an amino acid sequence as shown in SEQ ID No. 37 or an amino acid sequence which has at least 60% identity thereto.

Preferably, the lipid acyltransferase for use in the methods and uses according to the present invention is a lipid acyltransferase capable of hydrolysing at least galactolipids and/or capable of transferring an acyl group from at least a galactolipid to one or more acyl acceptor substrates, wherein the enzyme is obtainable, preferably obtained, from *Thermobifida* species, preferably *Thermobifida fusca*.

Preferably, the lipid acyltransferase for use in the methods and uses according to the present invention is a lipolytic enzyme capable of hydrolysing at least galactolipids and/or capable of transferring an acyl group from at least a galactolipid to one or more acyl acceptor substrates, wherein the enzyme is obtainable, preferably obtained, from *Corynebacterium* species, preferably *Corynebacterium efficiens*.

In a further embodiment the lipid acyltransferase for use in the methods and uses according to the present invention may be a lipid acyltransferase comprising any one of the amino acid sequences shown as SEQ ID No. 37, 38, 40, 41, 43, 45 or 47 or an amino acid sequence which has at least 70%, 75%, 80%, 85%, 90%, 95%, 96%, 97% or 98% identity therewith, or encoded by any one of the nucleotide sequences shown as SEQ ID No. 39, 42, 44, 46 or 48 or a nucleotide sequence which has at least 70%, 75%, 80%, 85%, 90%, 95%, 96%, 97% or 98% identity therewith.

In a further embodiment the lipid acyltransferase for use in the methods and uses according to the present invention may be a lipid acyltransferase comprising any one of amino sequences shown as SEQ ID No. 38, 40, 41, 45 or 47 or an amino acid sequence which has at least 70%, 75%, 80%, 85%, 90%, 95%, 96%, 97% or 98% identity therewith for the uses described herein.

In a further embodiment the lipid acyltransferase for use in the methods and uses according to the present invention may be a lipid acyltransferase comprising any one of amino sequences shown as SEQ ID No. 38, 40, or 47 or an amino acid sequence which has at least 70%, 75%, 80%, 85%, 90%, 95%, 96%, 97% or 98% identity therewith for the uses described herein.

More preferably in one embodiment the lipid acyltransferase for use in the methods and uses according to the present invention may be a lipid acyltransferase comprising the amino acid sequence shown as SEQ ID No. 47 or an amino acid sequence which has at least 70%, 75%, 80%, 85%, 90%, 95%, 96%, 97% or 98% identity therewith.

In another embodiment the lipid acyltransferase for use in the methods and uses according to the present invention may be a lipid acyltransferase comprising the amino acid sequence shown as SEQ ID No. 43 or 44 or an amino acid sequence which has at least 80%, 85%, 90%, 95%, 96%, 97% or 98% identity therewith.

In another embodiment the lipid acyltransferase for use in the methods and uses according to the present invention may be a lipid acyltransferase comprising the amino acid sequence shown as SEQ ID No. 41 or an amino acid sequence which has at least 70%, 75%, 80%, 85%, 90%, 95%, 96%, 97% or 98% identity therewith.

In one embodiment the lipid acyltransferase for use in the methods and uses according to the present invention may be a lipid acyltransferase capable of hydrolysing at least galactolipids and/or capable of transferring an acyl group from at least a galactolipid to one or more acyl acceptor substrates, wherein the enzyme is encoded by a nucleic acid selected from the group consisting of:
 a) a nucleic acid comprising a nucleotide sequence shown in SEQ ID No. 36;
 b) a nucleic acid which is related to the nucleotide sequence of SEQ ID No. 36 by the degeneration of the genetic code; and
 c) a nucleic acid comprising a nucleotide sequence which has at least 70% identity with the nucleotide sequence shown in SEQ ID No. 36.

In one embodiment the lipid acyltransferase according to the present invention may be a lipid acyltransferase obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable lipid acyltransferases for use in accordance with the present invention and/or in the methods of the present invention may comprise any one of the following amino acid sequences and/or be encoded by the following nucleotide sequences:
a polynucleotide encoding a lipid acyltransferase according to the present invention (SEQ ID No. 16);
an amino acid sequence of a lipid acyltransferase according to the present invention (SEQ ID No. 17).

A suitable lipid acyl-transferase enzyme for use in the methods of the invention may also be identified by alignment to the L131 (SEQ ID No. 37) sequence using Align X, the Clustal W pairwise alignment algorithm of Vector NTI using default settings.

An alignment of the L131 and homologues from *S. avermitilis* and *T. fusca* illustrates that the conservation of the GDSx motif (GDSY in L131 and *S. avermitilis* and *T. fusca*), the GANDY box, which is either GGNDA or GGNDL, and the HPT block (considered to be the conserved catalytic histadine). These three conserved blocks are highlighted in FIG. 61.

When aligned to either the pfam Pfam00657 consensus sequence (as described in WO04/064987) and/or the L131 sequence herein disclosed (SEQ ID No 37) it is possible to identify three conserved regions, the GDSx block, the GANDY block and the HTP block (see WO04/064987 for further details).

When aligned to either the pfam Pfam00657 consensus sequence (as described in WO04/064987) and/or the L131 sequence herein disclosed (SEQ ID No 37)

i) The lipid acyl-transferase enzyme of the invention, or for use in methods of the invention, has preferably a GDSx motif, more preferably a GDSx motif selected from GDSL or GDSY motif.
and/or
ii) The lipid acyl-transferase enzyme of the invention, or for use in methods of the invention, has preferably a GANDY block, more preferably a GANDY block comprising amino GGNDx, more preferably GGNDA or GGNDL.
and/or
iii) The enzyme of the invention, or for use in methods of the invention, has preferable an HTP block. and preferably
iv) The galactolipase/lipid acyl-transferase enzyme of the invention, or for use in methods of the invention, has preferably a GDSx or GDSY motif, and a GANDY block comprising amino GGNDx, preferably GGNDA or GGNDL, and a HTP block (conserved histadine).

Suitably, when the lipid acyltransferase for use in the methods or uses of the present invention, may be a variant lipid acyltransferase, in which case the enzyme may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7 (defined hereinbelow).

For instance the variant lipid acyltransferase enzyme for use in the methods or uses of the present invention may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues detailed in set 2 or set 4 or set 6 or set 7 (defined hereinbelow) identified by said parent sequence being structurally aligned with the structural model of P10480 defined herein, which is preferably obtained by structural alignment of P10480 crystal structure coordinates with 1IVN.PDB and/or 1DEO.PDB as taught herein.

In a further embodiment the variant lipid acyltransferase enzyme for use in the methods or uses of the present invention may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues taught in set 2 identified when said parent sequence is aligned to the pfam consensus sequence (SEQ ID No. 2—FIG. 12) and modified according to a structural model of P10480 to ensure best fit overlap (see FIG. 30) as taught herein.

Suitably the variant lipid acyltransferase enzyme may comprise an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 1, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues defined in set 2 or set 4 or set 6 or set 7 (hereinafter defined) identified by sequence alignment with SEQ ID No. 34.

Alternatively the variant lipid acyltransferase enzyme may be a variant enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues defined in set 2 or set 4 or set 6 or set 7 identified by said parent sequence being structurally aligned with the structural model of P10480 defined herein, which is preferably obtained by structural alignment of P10480 crystal structure coordinates with 1IVN.PDB and/or 1DEO.PDB as taught herein.

Alternatively, the variant lipid acyltransferase enzyme may be a variant enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues taught in set 2 identified when said parent sequence is aligned to the pfam consensus sequence (SEQ ID No. 2) and modified according to a structural model of P10480 to ensure best fit overlap (see FIG. 30) as taught hereinbelow.

The term "modifying" as used herein means adding, substituting and/or deleting. Preferably the term "modifying" means "substituting".

For the avoidance of doubt, when an amino acid is substituted in the parent enzyme it is preferably substituted with an amino acid which is different from that originally found at that position in the parent enzyme thus to produce a variant enzyme. In other words, the term "substitution" is not intended to cover the replacement of an amino acid with the same amino acid.

Preferably, the parent enzyme is an enzyme which comprises the amino acid sequence shown as SEQ ID No. 34 and/or SEQ ID No. 15 and/or SEQ ID No. 35.

Preferably, the variant enzyme is an enzyme which comprises an amino acid sequence, which amino acid sequence is shown as SEQ ID No. 34 or SEQ ID No. 35 except for one or more amino acid modifications at any one or more of the amino acid residues defined in set 2 or set 4 or set 6 or set 7.

In one embodiment, preferably the variant enzyme comprises one or more amino acid modifications compared with the parent sequence at least one of the amino acid residues defined in set 4.

Suitably, the variant enzyme comprises one or more of the following amino acid modifications compared with the parent enzyme:
S3E, A, G, K, M, Y, R, P, N, T or G
E309Q, R or A, preferably Q or R
–318Y, H, S or Y, preferably Y.

Preferably, X of the GDSX motif is L. Thus, preferably the parent enzyme comprises the amino acid motif GDSL.

Preferably the method of producing a variant lipid acyltransferase enzyme further comprises one or more of the following steps:
1) structural homology mapping or
2) sequence homology alignment.

Suitably, the structural homology mapping may comprise one or more of the following steps:
i) aligning a parent sequence with a structural model (1IVN.PDB) shown in FIG. 46;
ii) selecting one or more amino acid residue within a 10 Å sphere centred on the central carbon atom of the glycerol molecule in the active site (see FIG. 47) (such as one or more of the amino acid residues defined in set 1 or set 2); and
iii) modifying one or more amino acids selected in accordance with step (ii) in said parent sequence.

In one embodiment the amino acid residue selected may reside within a 9, preferably within a 8, 7, 6, 5, 4, or 3 Å sphere centred on the central carbon atom of the glycerol molecule in the active site (see FIG. 47).

Suitably, the structural homology mapping may comprise one or more of the following steps:
i) aligning a parent sequence with a structural model (1IVN.PDB) shown in FIG. 46;
ii) selecting one or more amino acids within a 10 Å sphere centred on the central carbon atom of the glycerol molecule in the active site (see FIG. 47) (such as one or more of the amino acid residues defined in set 1 or set 2);
iii) determining if one or more amino acid residues selected in accordance with step (ii) are highly conserved (particularly are active site residues and/or part of the GDSx motif and/or part of the GANDY motif); and
iv) modifying one or more amino acids selected in accordance with step (ii), excluding conserved regions identified in accordance with step (iii) in said parent sequence.

In one embodiment the amino acid residue selected may reside within a 9, preferably within a 8, 7, 6, 5, 4, or 3 Å sphere centred on the central carbon atom of the glycerol molecule in the active site (see FIG. 47).

Alternatively to, or in combination with, the structural homology mapping described above, the structural homology mapping can be performed by selecting specific loop regions (LRs) or intervening regions (IVRs) derived from the pfam alignment (Alignment 2, FIG. 48) overlaid with the P10480 model and 1IVN. The loop regions (LRs) or intervening regions (IVRs) are defined in the Table below:

|  | P10480 amino acid positions (SEQ ID No 34) |
| --- | --- |
| IVR1 | 1-19 |
| Loop1 (LR1) | 20-41 |
| IVR2 | 42-76 |
| Loop2 (LR2) | 77-89 |
| IVR3 | 90-117 |
| Loop3 (LR3) | 118-127 |
| IVR4 | 128-145 |
| Loop4 (LR4) | 146-176 |
| IVR5 | 177-207 |
| Loop5 (LR5) | 208-287 |
| IVR6 | 288-317 |

In some embodiments of the present invention the variant acyltransferase enzyme for use in the methods and uses of the present invention not only comprises an amino acid modifications at one or more of the amino acids defined in any one of sets 1-4 and 6-7, but also comprises at least one amino acid modification in one or more of the above defined intervening regions (IVR1-6) (preferably in one or more of the IVRs 3, 5 and 6, more preferably in IVR 5 or IVR 6) and/or in one or more of the above-defined loop regions (LR1-5) (preferably in one or more of LR1, LR2 or LR5, more preferably in LR5).

In one embodiment, the variant acyltransferase for use in the methods and uses of the present invention may comprise one or more amino acid modification which is not only defined by one or more of set 2, 4, 6 and 7, but also is within one or more of the IVRs 1-6 (preferably within IVR 3, 5 or 6, more preferably within in IVR 5 or IVR 6) or within one or more of the LRs 1-5 (preferably within LR1, LR2 or LR5, more preferably within LR5).

Suitably, the variant acyltransferase for use in the methods and uses of the present invention may comprise one or more amino acid modification which is not only in set 1 or 2, but also is within IVR 3.

Suitably, the variant acyltransferase for use in the methods and uses of the present invention may comprise one or more amino acid modification which is not only in set 1 or 2, but also is within IVR 5.

Suitably, the variant acyltransferase for use in the methods and uses of the present invention may comprise one or more amino acid modification which is not only in set 1 or 2, but also is within IVR 6.

Suitably, the variant acyltransferase for use in the methods and uses of the present invention may comprise one or more amino acid modification which is not only in set 1 or 2, but also is within LR 1.

Suitably, the variant acyltransferase for use in the methods and uses of the present invention may comprise one or more amino acid modification which is not only in set 1 or 2, but also is within LR 2.

Likewise, in some embodiments of the present invention the variant acyltransferase enzyme for use in the methods and uses of the present invention not only comprises an amino acid modification at one or more amino acid residues which reside within a 10, preferably within a 9, 8, 7, 6, 5, 4, or 3, Å sphere centred on the central carbon atom of the glycerol molecule in the active site (see FIG. 47), but also comprises at least one amino acid modification in one or more of the above defined intervening regions (IVR1-6) (preferably in one or more of IVRs 3, 5 and 6, more preferably in IVR 5 or IVR 6)

and/or in one or more of the above-defined loop regions (LR1-5) (preferably in one or more of LR1, LR2 or LR5, more preferably in LR5).

In one embodiment, preferably the amino acid modification is at one or more amino acid residues which reside within a 10 Å sphere and also within LR5.

Thus, the structural homology mapping may comprise one or more of the following steps:
i) aligning a parent sequence with a structural model (1IVN.PDB) shown in FIG. 46;
ii) selecting one or more amino acid residue within a 10 Å sphere centred on the central carbon atom of the glycerol molecule in the active site (see FIG. 47) (such as one or more of the amino acid residues defined in set 1 or set 2); and/or selecting one or more amino acid residues within IVR1-6 (preferably within IVR 3, 5 or 6, more preferably within in IVR 5 or IVR 6); and/or selecting one or more amino acid residues within LR1-5 (preferably within LR1, LR2 or LR5, more preferably within LR5); and
iii) modifying one or more amino acids selected in accordance with step (ii) in said parent sequence.

In one embodiment the amino acid residue selected may reside within a 9 Å sphere, preferably within an 8, 7, 6, 5, 4, or 3 Å sphere centred on the central carbon atom of the glycerol molecule in the active site (see FIG. 47).

Suitably, the structural homology mapping may comprise one or more of the following steps:
i) aligning a parent sequence with a structural model (1IVN.PDB) shown in FIG. 46;
ii) selecting one or more amino acids within a 10 Å sphere centred on the central carbon atom of the glycerol molecule in the active site (see FIG. 47) (such as one or more of the amino acid residues defined in set 1 or set 2); and/or selecting one or more amino acid residues within IVR1-6 (preferably within IVR 3, 5 or 6, more preferably within in IVR 5 or IVR 6); and/or selecting one or more amino acid residues within LR1-5 (preferably within LR1, LR2 or LR5, more preferably within LR5);
iii) determining if one or more amino acid residues selected in accordance with step (ii) are highly conserved (particularly are active site residues and/or part of the GDSx motif and/or part of the GANDY motif); and
modifying one or more amino acids selected in accordance with step (ii), excluding conserved regions identified in accordance with step (iii) in said parent sequence.

Suitably, the one or more amino acids selected in the methods detailed above are not only within a 10 Å sphere centred on the central carbon atom of the glycerol molecule in the active site (see FIG. 47) (such as one or more of the amino acid residues defined in set 1 or set 2), but are also within one or more of the IVRs 1-6 (preferably within IVR 3, 5 or 6, more preferably within in IVR 5 or IVR 6) or within one or more of the LRs 1-5 (preferably within LR1, LR2 or LR5, more preferably within LR5).

In one embodiment, preferably the one or more amino acid modifications is/are within LR5. When it is the case that the modification(s) is within LR5, the modification is not one which is defined in set 5. Suitably, the one or more amino acid modifications not only fall with the region defined by LR5, but also constitute an amino acid within one or more of set 2, set 4, set 6 or set 7.

Suitably, the sequence homology alignment may comprise one or more of the following steps:
i) selecting a first parent lipid acyltransferase;
ii) identifying a second related lipid acyltransferase having a desirable activity;
iii) aligning said first parent lipid acyltransferase and the second related lipid acyltransferase;
iv) identifying amino acid residues that differ between the two sequences; and
v) modifying one or more of the amino acid residues identified in accordance with step (iv) in said parent lipid acyltransferase.

Suitably, the sequence homology alignment may comprise one or more of the following steps:
i) selecting a first parent lipid acyltransferase;
ii) identifying a second related lipid acyltransferase having a desirable activity;
iii) aligning said first parent lipid acyltransferase and the second related lipid acyltransferase;
iv) identifying amino acid residues that differ between the two sequences;
v) determining if one or more amino acid residues selected in accordance with step (iv) are highly conserved (particularly are active site residues and/or part of the GDSx motif and/or part of the GANDY motif); and
vi) modifying one or more of the amino acid residues identified in accordance with step (iv) excluding conserved regions identified in accordance with step (v) in said parent sequence.

Suitably, said first parent lipid acyltransferase may comprise any one of the following amino acid sequences: SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32 or SEQ ID No. 33.

Suitably, said second related lipid acyltransferase may comprise any one of the following amino acid sequences: SEQ ID No. 3, SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32 or SEQ ID No. 33.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID No. 34 or SEQ ID No. 35.

In one aspect preferably the variant enzyme comprises one or more of the following amino acid substitutions:
S3A, C, D, E, F, G, H, I, K, L, M, N, P, Q, R, T, V, W, or Y; and/or
L17A, C, D, E, F, G, H, I, K, M, N, P, Q, R, S, T, V, W, or Y; and/or
S18A, C, D, E, F, H, I, K, L, M, N, P, Q, R, T, W, or Y; and/or
K22A, C, D, E, F, G, H, I, L, M, N, P, Q, R, S, T, V, W, or Y; and/or
M23A, C, D, E, F, G, H, I, K, L, N, P, Q, R, S, T, V, W, or Y; and/or
Y30A, C, D, E, G, H, I, K, L, M, N, P, Q, R, S, T, V, or W; and/or
G40A, C, D, E, F, H, I, K, L, M, N, P, Q, R, S, T, V, W, or Y; and/or N80 A, C, D, E, F, G, H, I, K, L, M, P, Q, R, S, T, V, W, or Y; and/or
P81 A, C, D, E, F, G, H, I, K, L, M, N, Q, R, S, T, V, W, or Y; and/or
K82 A, C, D, E, F, G, H, I, L, M, N, P, Q, R, S, T, V, W, or Y; and/or
N87 A, C, D, E, F, G, H, I, K, L, M, P, Q, R, S, T, V, W, or Y; and/or
N88 A, C, D, E, F, G, H, I, K, L, M, P, Q, R, S, T, V, W, or Y; and/or
W111 A, C, D, E, F, G, H, I, K, L, M, N, P, Q, R, S, T, V, W or Y; and/or
V112 A, C, D, E, F, G, H, I, K, L, M, N, P, Q, R, S, T, W, or Y; and/or
A114 C, D, E, F, G, H, I, K, L, M, N, P, Q, R, S, T, V, W, or Y; and/or
Y117 A, C, D, E, F, G, H, I, K, L, M, N, P, Q, R, S, T, V, or W; and/or
L118 A, C, D, E, F, G, H, I, K, M, N, P, Q, R, S, T, V, W, or Y; and/or
P156 A, C, D, E, F, G, H, I, K, L, M, N, Q, R, S, T, V, W, or Y; and/or
D157 A, C, E, F, G, H, I, K, L, M, P, Q, R, S, T, V, W, or Y; and/or
G159 A, C, D, E, F, H, I, K, L, M, N, P, Q, R, S, T, V, W, or Y; and/or
Q160 A, C, D, E, F, G, H, I, K, L, M, N, P, R, S, T, V, W, or Y; and/or
N161 A, C, D, E, F, G, H, I, K, L, M P, Q, R, S, T, V, W, or Y; and/or
P162 A, C, D, E, F, G, H, I, K, L, M, N, Q, R, S, T, V, W, or Y; and/or
S163 A, C, D, E, F, G, H, I, K, L, M, N, P, Q, R, T, V, W, or Y; and/or
A164 C, D, E, F, G, H, I, K, L, M, N, P, Q, R, S, T, V, W, or Y; and/or
R165 A, C, D, E, F, G, H, I, K, L, M, N, P, Q, S, T, V, W, or Y; and/or
S166 A, C, D, E, F, G, H, I, K, L, M, N, P, Q, R, T, V, W, or Y; and/or
Q167 A, C, D, E, F, G, H, I, K, L, M, N, P, R, S, T, V, W, or Y; and/or
K168 A, C, D, E, F, G, H, I, L, M, N, P, Q, R, S, T, V, W, or Y; and/or
V169 A, C, D, E, F, G, H, I, K, L, M, N, P, Q, R, S, T, W, or Y; and/or
V170 A, C, D, E, F, G, H, I, K, L, M, N, P, Q, R, S, T, W, or Y; and/or
E171 A, C, D, F, G, H, I, K, L, M, N, P, Q, R, S, T, V, W, or Y; and/or
A172 C, D, E, F, G, H, I, K, L, M, N, P, Q, R, S, T, V, W, or Y; and/or
Y179 A, C, D, E, F, G, H, I, K, L, M, N, P, Q, R, S, T, V, or W; and/or
H180 A, C, D, E, F, G, I, K, L, M, P, Q, R, S, T, V, W, or Y; and/or
N181 A, C, D, E, F, G, H, I, K, L, M, P, Q, R, S, T, V, W, or Y; and/or
Q182 A, C, D, E, F, G, H, I, K, L, M, N, P, R, S, T, V, W, or Y; preferably K; and/or
M209 A, C, D, E, F, G, H, I, K, L, N, P, Q, R, S, T, V, W, or Y; and/or
L210 A, C, D, E, F, G, H, K, M, N, P, Q, R, S, T, V, W, or Y; and/or
R211 A, C, D, E, F, G, H, I, K, L, M, N, P, Q, S, T, V, W, or Y; and/or
N215 A, C, D, E, F, G, H, I, K, L, M, N, P, Q, R, S, T, V, W, or Y; and/or
Y226 A, C, D, E, G, H, I, K, L, M, N, P, Q, R, S, T, V, or W; and/or
Y230 A, C, D, E, G, H, I, K, L, M, N, P, Q, R, S, T, V or W; and/or
K284 A, C, D, E, F, G, H, I, L, M, N, P, Q, R, S, T, V, W, or Y; and/or
M285 A, C, D, E, F, G, H, I, K, L, N, P, Q, R, S, T, V, W, or Y; and/or
Q289 A, C, D, E, F, G, H, I, K, L, M, N, P, R, S, T, V, W, or Y; and/or
V290 A, C, D, E, F, G, H, I, K, L, M, N, P, Q, R, S, T, W, or Y; and/or
E309 A, C, D, F, G, H, I, K, L, M, N, P, Q, R, S, T, V, W, or Y; and/or
S310 A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

When it is the case that the residues in the parent backbone differ from those in P10480 (SEQ ID No. 2), as determined by homology alignment and/or structural alignment to P10480 and/or 1IVN, it may be desirable to replace the residues which align to any one or more of the following amino acid residues in P 10480 (SEQ ID No. 2): Ser3, Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309 or Ser310, with the residue found in P10480 respectively.

Variant enzymes which have a decreased hydrolytic activity against a phospholipid, such as phosphatidylcholine (PC), may also have an increased transferase activity from a phospholipid.

Variants enzymes which have an increased transferase activity from a phospholipid, such as phosphatidylcholine (PC), may also have an increased hydrolytic activity against a phospholipid.

Suitably, one or more of the following sites may be involved in substrate binding:
Leu17; Ala114; Tyr179; His180; Asn181; Met209; Leu210; Arg211; Asn215; Lys284; Met285; Gln289; Val290.

1. Modification of One or More of the Following Residues May Result in a Variant Enzyme Having an Increased Absolute Transferase Activity Against Phospholipid:

S3, D157, S310, E309, Y179, N215, K22, Q289, M23, H180, M209, L210, R211, P81, V112, N80, L82, N88; N87

Specific modifications which may provide a variant enzyme having an improved transferase activity from a phospholipid may be selected from one or more of the following:
S3 A, C, D, E, F, G, H, I, K, L, M, N, P, Q, R, T, V, W or Y; preferably N, E, K, R, A, P or M, most preferably S3A
D157 A, C, E, F, G, H, I, K, L, M, N, P, Q, R, S, T, V, W or Y; preferably D157S, R, E, N, G, T, V, Q, K or C
S310 A, C, D, E, F, G, H, I, K, L, M, N, P, Q, R, T, V, W or Y; preferably S310T-318 E
E309 A, C, D, E, F, G, H, I, K, L, M, N, P, Q, R, T, V, W or Y; preferably E309 R, E, L, R or A Y179 A, C, D, E, F, G, H, I, K, L, M, N, P, Q, R, S, T, V or W; preferably Y179 D, T, E, R, N, V, K, Q or S, more preferably E, R, N, V, K or Q N215 A, C, D, E, F, G, H, I, K, L, M, P, Q, R, S, T, V, W or Y; preferably N215 S, L, R or Y K22 A, C, D, E, F, G, H, I, L, M, N, P, Q, R, S, T, V, W or Y; preferably K22 E, R, C or A Q289 A, C, D, E, F, G, H, I, K, L, M, N, P, R, S, T, V, W or Y; preferably Q289 R, E, G, P or N M23 A, C, D, E, F, G, H, I, K, L N, P, Q, R, S, T, V, W or Y; preferably M23 K, Q, L, G, T or S H180 A, C, D, E, F, G, I, K, L, M, P, Q, R, S, T, V, W or Y; preferably H180 Q, R or K M209 A, C, D, E, F, G, H, I, K, L, N, P, Q, R, S, T, V, W or Y; preferably M209 Q, S, R, A, N, Y, E, V or L L210 A, C, D, E, F, G, H, I, K, M, N, P, Q, R, S, T, V, W or Y; preferably L210 R, A, V, S, T, I, W or M R211 A, C, D, E, F, G, H, I, K, L, M, N, P, Q, S, T, V, W or Y; preferably R211 T P81 A, C, D, E, F, G, H, I, K, L, M, N, Q, R, S, T, V, W or Y; preferably P81 G V112 A, C, D, E, F, G, H, I, K, L, M, N, P, Q, R, S, T, W or Y; preferably V112 C N80 A, C, D, E, F, G, H, I, K, L, M, P, Q, R, S, T, V, W or Y; preferably N80 R, G, N, D, P, T, E, V, A or G L82 A, C, D, E, F, G, H, I, M, N, P, Q, R, S, T, V, W or Y; preferably L82 N, S or E N88 A, C, D, E, F, G, H, I, K, L, M, P, Q, R, S, T, V, W or Y; preferably N88 C N87 A, C, D, E, F, G, H, I, K, L, M, P, Q, R, S, T, V, W or Y; preferably N87 M or G Modification of one or more of the following residues results in a variant enzyme having an increased absolute transferase activity against phospholipid:

S3 N, R, A, G

M23 K, Q, L, G, T, S

H180 R

L82 G

Y179 E, R, N, V, K or Q

E309 R, S, L or A

One preferred modification is N80D. This is particularly the case when using the reference sequence SEQ ID No. 35. Therefore in a preferred embodiment of the present invention the lipid acyltransferase according to the present invention comprises SEQ ID No. 35.

As noted above, when referring to specific amino acid residues herein the numbering is that obtained from alignment of the variant sequence with the reference sequence shown as SEQ ID No. 34 or SEQ ID No. 35

Much by preference, the lipid acyltransferase for use in the method and uses of the present invention may be a lipid acyltransferase comprising the amino acid sequence shown as SEQ ID No. 16 (FIG. 10), or an amino acid sequence which has 75% or more, preferably 85% or more, more preferably 90% or more, even more preferably 95% or more, even more preferably 98% or more, or even more preferably 99% or more identity to SEQ ID No. 16. This enzyme may be considered a variant enzyme.

For the avoidance of doubt, when a particular amino acid is taught at a specific site, for instance L118 for instance, this refers to the specific amino acid at residue number 118 in SEQ ID No. 34 unless otherwise stated. However, the amino acid residue at site 118 in a different parent enzyme may be different from leucine.

Thus, when taught to substitute an amino acid at residue 118, although reference may be made to L118 it would be readily understood by the skilled person that when the parent enzyme is other than that shown in SEQ ID No. 34, the amino acid being substituted may not be leucine. It is, therefore, possible that when substituting an amino acid sequence in a parent enzyme which is not the enzyme having the amino acid sequence shown as SEQ ID No. 34, the new (substituting) amino acid may be the same as that taught in SEQ ID No. 34. This may be the case, for instance, where the amino acid at say residue 118 is not leucine and is, therefore different from the amino acid at residue 118 in SEQ ID No. 34. In other words, at residue 118 for example, if the parent enzyme has at that position an amino acid other than leucine, this amino acid may be substituted with leucine in accordance with the present invention.

For the purposes of the present invention, the degree of identity is based on the number of sequence elements which are the same. The degree of identity in accordance with the present invention may be suitably determined by means of computer programs known in the art, such as GAP provided in the GCG program package (Program Manual for the Wisconsin Package, Version 8, August 1994, Genetics Computer Group, 575 Science Drive, Madison, Wis., US 53711) (Needleman & Wunsch (1970), J. of Molecular Biology 48, 443-45) using the following settings for polypeptide sequence comparison: GAP creation penalty of 3.0 and GAP extension penalty of 0.1. Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the lipid acyltransferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

Suitably, the lipid acyltransferase enzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus* sp, *Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis Thermobifida fusca* and *Corynebacterium efficiens*.

In one aspect, preferably the lipid acyltransferase enzyme according to the present invention is obtainable, preferably obtained, from one or more of *Aeromonas hydrophila* or *Aeromonas salmonicida*.

In one embodiment suitably the sterol and/or stanol may comprise one or more of the following structural features:
i) a 3-beta hydroxy group or a 3-alpha hydroxy group; and/or
ii) A:B rings in the cis position or A:B rings in the trans position or C5-C6 is unsaturated.

Suitable sterol acyl acceptors include cholesterol and phytosterols, for example alpha-sitosterol, beta-sitosterol, stigmasterol, ergosterol, campesterol, 5,6-dihydrosterol, brassicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, tocopherol, tocotrienol and other natural or synthetic isomeric forms and derivatives.

Advantageously, in one embodiment, the sterol acyl acceptor is tocopherol. Suitably the tocopherol may be one or more of gamma, delta, beta or d-alpha tocopherol—including d-alpha tocopherol acid succinate for example. In one embodiment, preferably the sterol acyl acceptor is alpha-tocopherol.

In one embodiment, preferably the method according to the present invention includes the step of adding tocopherol, preferably alpha-tocopherol, to the oil.

In one aspect, preferably the sterol acyl acceptor is cholesterol.

In one aspect, preferably the sterol and/or stanol acyl acceptor is a sterol and/or a stanol other than cholesterol.

In one aspect of the present invention suitably more than one sterol and/or stanol may act as the acyl acceptor, suitably more than two sterols and/or stanols may act as the acyl acceptor. In other words, in one aspect of the present invention, suitably more than one sterol ester and/or stanol ester may be produced. Suitably, when cholesterol is the acyl acceptor one or more further sterols or one or more stanols may also act as the acyl acceptor. Thus, in one aspect, the present invention provides a method for the in situ production of both a tocopherol ester and at least one other sterol or stanol ester in combination. In other words, the lipid acyltransferase for some aspects of the present invention may transfer an acyl group from a lipid to both tocopherol and at least one further sterol and/or at least one stanol.

In some aspects, the oil prepared in accordance with the present invention may be used to reduce the risk of cardiovascular diseases.

In one aspect, the oil prepared in accordance with the present invention may be used to reduce blood serum cholesterol and/or to reduce low density lipoprotein. Blood serum cholesterol and low density lipoproteins have both been associated with certain diseases in humans, such as atherosclerosis and/or heart disease for example. Thus, it is envisaged that the oils prepared in accordance with the present invention may be used to reduce the risk of such diseases.

In another aspect the present invention provides the use of an edible oil according to the present invention for use in the treatment and/or prevention of cardiovascular diseases.

Thus, in one aspect the present invention provides the use of an edible oil according to the present invention for use in the treatment and/or prevention of atherosclerosis and/or heart disease.

In a further aspect, the present invention provides a medicament comprising an edible oil according to the present invention.

In a further aspect, the present invention provides a method of treating and/or preventing a disease in a human or animal patient which method comprising administering to the patient an effective amount of an edible oil according to the present invention.

Suitably the sterol acyl acceptor may be one which is naturally found in edible or vegetable oils.

Alternatively, or in addition, the sterol acyl acceptor may be one which added to the edible or vegetable oil.

When it is the case that a sterol and/or a stanol is added to the edible oil, the sterol and/or stanol may be added before, simultaneously with, and/or after the addition of the lipid acyltransferase according to the present invention. Suitably, the present invention may encompass the addition of exogenous sterols/stanols, particularly phytosterols/phytostanols, to an edible or vegetable oil prior to or simultaneously with the addition of the enzyme according to the present invention.

For some aspects, one or more sterols present in the edible oil may be converted to one or more stanols prior to or at the same time as the lipid acyltransferase is added according to the present invention. Any suitable method for converting sterols to stanols may be employed. For example, the conversion may be carried out by chemical hydrogenation for example. The conversion may be conducted prior to the addition of the lipid acyltransferase in accordance with the present invention or simultaneously with the addition of the lipid acyltransferase in accordance with the present invention. Suitably enzymes for the conversion of sterols to stanols are taught in WO00/061771.

Suitably the present invention may be employed to produce phytostanol esters in situ in an edible oil. Phytostanol esters have increased solubility through lipid membranes, bioavailability and enhanced health benefits (see for example WO92/99640).

An advantage of the present invention is that sterol and/or stanol esters are produced in the edible oil during the degumming thereof. A further advantage is that enzyme is degummed without an increase, or a substantial, increase, in the free fatty acid content of the edible oil. The production of free fatty acids can be detrimental in the edible oil. Preferably, the method according to the present invention results in the degumming of an edible oil wherein the accumulation of free fatty acids is reduced and/or eliminated. Without wishing to be bound by theory, in accordance with the present invention the fatty acid which is removed from the lipid is transferred by the lipid acyltransferase to an acyl acceptor, for example a sterol and/or a stanol. Thus, the overall level of free fatty acids in the foodstuff does not increase or increases only to an insignificant degree. This is in sharp contradistinction to the situation when phospholipases, such as Lecitase Ultra™ are used in enzymatic degumming of edible oils. In particular, the use of such phospholipases can result in an increased amount of free fatty acid in the edible oil, which can be detrimental. In accordance with the present invention, the accumulation of free fatty acids is reduced and/or eliminated when compared with the amount of free fatty acids which would have been accumulated had a phospholipase A enzyme, such as Lecitase Ultra™, been used in place of the lipid acyltransferase in accordance with the present invention.

A lipid acyl transferase according to the present invention may be suitable for use in the enzymatic degumming of vegetable or edible oils. In processing of vegetable or edible oil the edible or vegetable oil is treated with a lipid acyl transferase according to the present invention so as to hydrolyse a major part of the phospholipid. Preferably, the fatty acyl groups are transferred from the polar lipids to an acyl acceptor. The degumming process typically results in the reduction of the content of the polar lipids, particularly of phospholipids, in an edible oil due to hydrolysis of a major part (i.e. more than 50%) of the phospholipid. Typically, the aqueous phase containing the hydrolysed phospholipid is separated from the oil. Suitably, the edible or vegetable oil may initially (pre-treatment with the enzyme according to the present invention) have a phosphorus content of 50-250 ppm.

As the skilled person is aware, the term "degumming" as used herein means the refining of oil by converting phosphatides (such as lecithin, phospholipids and occluded oil) into hydratable phosphatides. Oil which has been degummed is more fluid and thus has better handling properties than oil which has not been degummed.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

Enzyme suitable for use in the methods of the invention preferably have phospholipase activity in a standard phospholipase activity assay taught hereinbelow.

Determination of Phospholipase Activity (Phospholipase Activity Assay (PLU-7)):

Substrate 0.6% L-α Phosphatidylcholine 95% Plant (Avanti #441601), 0.4% Triton-X 100 (Sigma X-100) and 5 mM $CaCl_2$ was dispersed in 0.05M HEPES buffer pH 7.

Assay Procedure:

400 μL substrate was added to a 1.5 mL Eppendorf tube and placed in an Eppendorf Thermomixer at 37° C. for 5 minutes. At time t=0 min, 50 μL enzyme solution was added. Also a blank with water instead of enzyme was analyzed. The sample was mixed at 10×100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromole fatty acid produced per minute under assay conditions.

More preferably the lipid acyl-transferase will also have transferase activity as defined by the protocol below:

Protocol for the Determination of % Acyltransferase Activity:

An edible oil to which a lipid acyltransferase according to the present invention has been added may be extracted following the enzymatic reaction with CHCl3:CH3OH 2:1 and the organic phase containing the lipid material is isolated and analysed by GLC and HPLC according to the procedure detailed hereinbelow. From the GLC and HPLC analyses the amount of free fatty acids and one or more of sterol/stanol esters; are determined. A control edible oil to which no enzyme according to the present invention has been added, is analysed in the same way.

Calculation:

From the results of the GLC and HPLC analyses the increase in free fatty acids and sterol/stanol esters can be calculated:

Δ% fatty acid=% Fatty acid(enzyme)−% fatty acid (control); $Mv$ fatty acid=average molecular weight of the fatty acids;

$A$=Δ% sterol ester/Mv sterol ester (where Δ% sterol ester=% sterol/stanol ester(enzyme)−% sterol/stanol ester(control) and $Mv$ sterol ester =average molecular weight of the sterol/stanol esters);

The transferase activity is calculated as a percentage of the total enzymatic activity:

$$\% \text{ transferase activity} = \frac{A \times 100}{A + \Delta \% \text{ fatty acid}/(Mv \text{ fatty acid})}$$

If the free fatty acids are increased in the edible oil they are preferably not increased substantially, i.e. to a significant degree. By this we mean, that the increase in free fatty acid does not adversely affect the quality of the edible oil.

The edible oil used for the acyltransferase activity assay is preferably the soya bean oil supplemented with plant sterol (1%) and phosphatidylcholine (2%) oil using the method in Example 3. For the assay the enzyme dosage used is preferably 0.2 PLU-7/g oil, more preferably 0.08 PLU-7/g oil. The level of phospholipid present in the oil and/or the % conversion of sterol is preferably determined after 4 hours, more preferably after 20 hours.

In some aspects of the present invention, the term "without substantially increasing free fatty acids" as used herein means that the amount of free fatty acid in a edible oil treated with an lipid acyltransferase according to the present invention is less than the amount of free fatty acid produced in the edible oil when an enzyme other than a lipid acyltransferase according to the present invention had been used, such as for example as compared with the amount of free fatty acid produced when a conventional phospholipase enzyme, e.g. Lecitase Ultra™ (Novozymes A/S, Denmark), had been used.

In addition to, or instead of, assessing the % transferase activity in an oil (above), to identify the lipid acyl transferase enzymes most preferable for use in the methods of the invention the following assay entitled "Protocol for identifying lipid acyltransferases for use in the present invention" can be employed.

Protocol for Identifying Lipid Acyltransferases

A lipid acyltransferase in accordance with the present invention is on which results in:

i) the removal of phospholipid present in a soya bean oil supplemented with plant sterol (1%) and phosphatidylcholine (2%) oil using the method taught in Example 3. and/or ii) the conversion (% conversion) of the added sterol to sterol-ester when using the method taught in Example 3. The GLC method for determining the level of sterol and sterol esters as taught in Example 5 may be used.

For the assay the enzyme dosage used may be 0.2 PLU-7/g oil, preferably 0.08 PLU-7/g oil. The level of phospholipid present in the oil and/or the conversion (% conversion) of sterol is preferably determined after 4 hours, more preferably after 20 hours.

In the protocol for identifying lipid acyl transferases, after enzymatic treatment, 5% water is preferably added and thoroughly mixed with the oil. The oil is then separated into an oil and water phase using centrifugation (see "Enzyme-catalyzed degumming of vegetable oils" by Buchold, H. and Laurgi A.-G., Fett Wissenschaft Technologie (1993), 95(8), 300-4, ISSN: 0931-5985), and the oil phase can then be analysed for phosphorus content using the following protocol ("Assay for Phosphorus Content"):

Assay for Phosphorus Content

The level of phospholipid present in an oil after degumming is determined by first preparing the oil sample according to the sample preparation taught in the AOAC Official Method 999.10 (>Lead, Cadmium, Zinc, Copper, and Iron in Foods Atomic Absorption Spectrophotometry after Microwave Digestion, First Action 1999 NMKL-AOAC Method). The amount of phospholipids in the oil is then measured by analysing the phosphorus content in the oil sample after degumming according to the AOAC Official Method 985.01 (>Metals and Other Elements in Plants and Pet Foods Inductively Coupled Plasma Spectroscopic Method First Action 1985 Final Action 1988).

The amount of phosphorus present in the oil after degumming is preferably less than 50 ppm, preferably less than 40 ppm, preferably less than 30 ppm, preferably less than 20 ppm, preferably less than 10 ppm, preferably less than 5 ppm. The oil after degumming, as illustrated in the examples may be substantially free of phospholipid, i.e. contain less than 1 ppm phospholipid.

The % conversion of the sterol present in the oil is at least 1%, preferably at least 5%, preferably at least 10%, preferably at least 20%, preferably at least 30%, preferably at least 40%, preferably at least 50%, preferably at least 60%, preferably at least 70%, preferably at least 80%, preferably at least 90%, preferably at least 95%.

In one embodiment the % conversion of the sterol present in the oil is at least 5%, preferably at least 20%.

Low Water Degumming

It has surprisingly been found that when a lipid acyl transferase is used in a process of enzymatic degumming of an edible oil, the enzymatic degumming can be performed in a very low water environment. Some water may still be required, for example when adding the enzyme to the oil the enzyme may be added in small amount of water, such as less than 1%, preferably 0.5%, more preferably less than 0.2%, more preferably less than 1%.

Preferably the water content of the edible oil in the processes and uses according to the present invention is less than 1%, preferably less than 0.5%, more preferably less than 0.2%, more preferably less than 0.1%.

Thus, one advantage of the present invention is that when only a small amount of water (i.e. <5%, preferably <1%, preferably <0.5%, preferably <0.2%) is used during the enzymatic degumming the gums (i.e. the phosphorus containing portion) separates from the oil, for example in the form of a solid precipitate. The solid precipitate can be readily removed from the degummed oil by methods such as simply decanting the oil or removing or the gum by filtration for example.

This contrasts sharply with conventional enzymatic degumming processes in which a significant amount of water is added to the oil. This is because in the conventional enzymatic degumming processes post-degumming because of the high water content, one obtains a water layer which comprises the phosphorus containing portion (for example that portion comprising lysophospholipids). This water lay must be removed and can be removed by centrifugation for example. However, the removal of the water layer is significantly more difficult that the removal of the solid precipitate obtained when using the process of the present invention.

Therefore the enzymatic degumming process according to the present invention could be considered as a "low water degumming process".

In one embodiment of the present invention, the gum may be removed by adjusting the oil to 5% water followed by centrifugation of the oil. (see "Enzyme-catalyzed degumming of vegetable oils" by Buchold, H. and Laurgi A.-G., Fett Wissenschaft Technologie (1993), 95(8), 300-4).

Therefore, the invention provides a process for the degumming of an edible oil, such as a crude edible oil (for example a crude soya oil), without the need for either a prewashing step prior to degumming and/or a step of removing the water added during degumming, which is required when using conventional phospholipases such as pancreatic phospholipase and Lecitase Ultra™.

Preferably, the edible oil has a less than a 4.5% water content, more preferably less than 4%, less than 3%, less than 2%, less than 1%, less than 0.5%.

Suitably, the edible oil may contain at least 0.1% water, such as at least 0.3%, 0.4% or 0.5%.

Preferred lipid acyltransferases for use in the present invention are identified as those which have a high activity such as high phospholipid hydrolytic activity or high phospholipid transferase activity on phospholipids in an oil environment, most preferably lipid acyl transferases for use in enzymatic degumming have a high phospholipid to sterol transferase activity.

As detailed above, other acyl-transferases suitable for use in the methods of the invention may be identified by identifying the presence of the GDSx, GANDY and HPT blocks either by alignment of the pFam00657 consensus sequence (SEQ ID No 1), and/or alignment to a GDSx acyltransferase, for example SEQ ID No 28. In order to assess their suitability for degumming, i.e. identify those enzymes which have a transferase activity of at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity, such acyltransferases are tested using the "Protocol for the determination of % acyltransferase activity" assay detailed hereinabove.

The present invention relates to the use of a lipid acyl transferase according to the present invention in degumming edible vegetable oils and/or edible oils and to methods for degumming edible or vegetable oils.

In one aspect, the present invention may provide a method comprising using a lipid acyl transferase to remove the non-hydratable phosphorus (NHP) content in oil comprising a relatively high amount of NHP.

The term "edible oil" as uses herein may encompass vegetable oils.

Preferably, the edible oil prior to treatment in accordance with the present invention comprises a non-hydratable phosphorus content of 50-250 ppm, preferably at least 60 ppm, more preferably at least 100 ppm, and even more preferably at least 200 ppm, even more preferably above 250 ppm.

More preferably, the edible oil prior to treatment in accordance with the present invention comprises a non-hydratable phosphorous content in the range of 60-500 ppm, more preferably in the range of 100-500 ppm, and even more preferably in the range of 200-500 ppm.

An edible oil as referred to herein may be any oil having a relatively high amount of a non-hydratable phosphorus, this may include water degummed oil, or more preferably this is a crude-oil or a semi-crude oil.

In one aspect, the crude edible oil has, prior to carrying out the method of the invention, a phosphorous content above 350 ppm, more preferably above 400 ppm, even more preferably above 500 ppm, and most preferably above 600 ppm.

Oils encompassed by the method according to the present invention may include, but are not limited to, one or more of soya bean oil, canola oil, corn oil, cottonseed oil, palm oil, coconut oil, peanut oil, olive oil, safflower oil, palm kernel oil, rape seed oil and sunflower oil.

Preferably, the oil is one or more of soya bean oil, sunflower oil and rape seed oil (sometimes referred to as canola oil).

More preferably, the oil is one or more of soya bean oil, sunflower oil or rape seed oil.

Most preferably, the oil is soya bean oil.

These oils may be in the form of a crude oil, a semicrude oil, or a water-degummed oil.

As used herein, "crude oil" (also referred to herein as a non-degummed oil) may be a pressed or extracted oil or a mixture thereof from e.g. rapeseed, soybean, or sunflower. The phosphatide content in a crude oil may vary from 0.5-3% w/w corresponding to a phosphorus content in the range of 200-1200 ppm, more preferably in the range of 250-1200 ppm. Apart from the phosphatides the crude oil also contains small concentrations of carbohydrates, sugar compounds and metal/phosphatide acid complexes of Ca, Mg and Fe.

As used herein, "semicrude oil" refers to any oil which is not a crude oil, but which has a phosphatide content above 250 ppm, more preferably above 500 ppm. Such an oil could e.g. be obtained by subjecting a crude oil to a process similar to the "water degumming" process described below.

As used herein, "water-degummed oil" may be typically be obtained by a "water degumming process" comprising mixing 1-3% w/w of hot water with warm (60-90° C.) crude oil. Usual treatment periods are 30-60 minutes. The water-degumming step removes the phosphatides and mucilaginous gums which become insoluble in the oil when hydrated. The hydrated phosphatides and gums can be separated from the oil by settling, filtration or centrifugation—centrifugation being the more prevalent practice. The essential object in said water-degumming process is to separate the hydrated phosphatides from the oil. The mixing of hot water into the oil, described above, should herein be understood broadly as mixing of an aqueous solution into the oil according to standard water-degumming procedures in the art.

Advantageously, the method and uses of the present invention enable degumming of edible oils in a low water (<5%, preferably less than 2%, more preferably less than 1%) environments. Therefore degumming can be performed with adding less water than when using conventional enzymes. A further advantage of the present invention is the production of sterol esters (in particular tocopherol esters) in the oil. A yet further advantage of the present invention is removal (preferably complete removal) of phospholipids. A further advantage of the present invention is the removal (preferably complete removal) of phospholipids without removal of phytosterol, and in particular tocopherol. It is preferred that, due to the esterification of the phytosterol, there is no significant removal of phytosterols such as tocopherol from the oil instead they are simply esterified. However, in one embodiment the amount of phytosterol such as tocopherol may be reduced. In such embodiments the absolute levels of phytosterol such as tocopherol may be reduced by preferably no more than 10%, alternatively no more than 25%, alternatively no more than 50%, alternatively no more than 75%. A yet further advantage of the present invention is the removal (preferably complete removal) of phospholipids without hydrolysis of triglycerides.

For the ease of reference, these and further aspects of the present invention are now discussed under appropriate section headings. However, the teachings under each section are not necessarily limited to each particular section.

Definition of Sets

Amino Acid Set 1:

Amino Acid Set 1

Gly8 Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158

The highly conserved motifs, such as GDSx and catalytic residues, were deselected from set 1 (residues underlined). For the avoidance of doubt, set 1 defines the amino acid residues within 10 Å of the central carbon atom of a glycerol in the active site of the 1IVN model.

Amino Acid Set 2:

Amino acid set 2 (note that the numbering of the amino acids refers to the amino acids in the P10480 mature sequence)

Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

| IVN model | | | P10480 |
|---|---|---|---|
| | A. hyd homologue | | Mature sequence Residue |
| IVN | PFAM | Structure | Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |
| Pro110 | | 180 to 190 | Pro162 |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |

-continued

| IVN model | | | P10480 |
|---|---|---|---|
| | A. hyd homologue | | Mature sequence Residue |
| IVN | PFAM | Structure | Number |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino Acid Set 3:

Amino acid set 3 is identical to set 2 but refers to the *Aeromonas salmonicida* (SEQ ID No. 28) coding sequence, i.e. the amino acid residue numbers are 18 higher in set 3 as this reflects the difference between the amino acid numbering in the mature protein (SEQ ID No. 2) compared with the protein including a signal sequence (SEQ ID No. 28).

The mature proteins of *Aeromonas salmonicida* GDSX (SEQ ID No. 28) and *Aeromonas hydrophila* GDSX (SEQ ID No. 26) differ in five amino acids. These are Thr3Ser, Gln182Lys, Glu309Ala, Ser310Asn, Gly318-, where the *salmonicida* residue is listed first and the *hydrophila* residue is listed last (FIG. 59). The *hydrophila* protein is only 317 amino acids long and lacks a residue in position 318. The *Aeromonas salmonicidae* GDSX has considerably high activity on polar lipids such as galactolipid substrates than the *Aeromonas hydrophila* protein. Site scanning was performed on all five amino acid positions.

Amino Acid Set 4:

Amino acid set 4 is S3, Q182, E309, S310, and –318.

Amino Acid Set 5:

F13S, D15N, S18G, S18V, Y30F, D116N, D116E, D157 N, Y226F, D228N Y230F.

Amino Acid Set 6:

Amino acid set 6 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, –318.

The numbering of the amino acids in set 6 refers to the amino acids residues in P10480 (SEQ ID No. 2)—corresponding amino acids in other sequence backbones can be determined by homology alignment and/or structural alignment to P10480 and/or 1IVN.

Amino Acid Set 7:

Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, –318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y).

The numbering of the amino acids in set 7 refers to the amino acids residues in P10480 (SEQ ID No. 2)—corresponding amino acids in other sequence backbones can be determined by homology alignment and/or structural alignment to P10480 and/o 1IVN).r Isolated In one aspect, preferably the polypeptide or protein for use in the present invention is in an isolated form. The term "isolated" means that the sequence is at least substantially free from at least one other component with which the sequence is naturally associated in nature and as found in nature.

Purified

In one aspect, preferably the polypeptide or protein for use in the present invention is in a purified form. The term "purified" means that the sequence is in a relatively pure state—e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods ell known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984)2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, in addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, and/or substrate.

As will be apparent to a person skilled in the art, using molecular evolution tools an enzyme may be altered to improve the functionality of the enzyme.

Suitably, the lipid acyltransferase used in the invention may be a variant, i.e. may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the lipid acyltransferase for use in the invention may be a variant with enhanced enzyme activity phospholipids when compared to the parent enzyme. Preferably, such variants also have low or no activity on lyso polar lipids. The enhanced activity on phospholipids may be the result of hydrolysis and/or transferase activity or a combination of both.

Variant lipid acyltransferases for use in the invention may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 January 15: 266 (2): 997-1000; Robertson et al J. Biol. Chem. 1994 Jan. 21; 269(3):2146-50; Brumlik et al J. Bacteriol 1996 April; 178 (7): 2060-4; Peelman et al Protein Sci. 1998 March; 7(3):587-99.

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

In a preferable aspect of the present invention the following software and settings for calculating percentage homology/identity are used. For amino acid sequences percentage of identities (homology) or "positives" are calculated by the AlignX Vector NTI (Vector NTI Advance 9.1 from Invitrogen Corporation, Carlsbad, Calif., USA.), for each possible pair of amino acid sequences Settings are default parameters (Gap opening penalty —10, Gap extension penalty 0.1).

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
|   |   | I L V |
|   | Polar - uncharged | C S T M |
|   |   | N Q |
|   | Polar - charged | D E |
|   |   | K R |
| AROMATIC |   | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This maybe useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a fisher embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

In one embodiment the host cell is a bacteria, preferably a gram-positive bacteria, preferably a host cell selected from *Actinobacteria*, such as *Biofidobacteria* and *Aeromonas*, particularly preferably *Aeromonas salmonicida*. Still more preferred are Actinomicetales such as *Corynebacteria*, in particular *Corynebacterium glutamicum* and *Nocardia*. Particularly preferred are *Streptomycetaceae*, such as *Streptomyces*, especially *S. lividans*.

A microbial host can be used for expression of the galactolipase gene, e.g. *Eubacteria, Archea* or *Fungi*, including yeast. Preferred are Eubacteria, for example, *Firmicutes* (low GC-Gram positive bacteria), such as *Bacillus subtilis* and other *bacillus* species, lactic acid bacteria such as species of genera *Lactobacillus* and *Lactococcus*.

Also preferred are Gram-negative *Proteobacteria*, in particular *Gammaproteobacteria*, such as host species belonging to the genera *Pseudomonas, Xanthomonas, Citrobacter* and *Escherichia*, especially *Escherichia coli*.

Preferably the host species is a Gram positive expression host such as *Aeromonas salmonicida, Streptomyces lividans* or *Corynebacterium glutamicum* as detailed in GB application number 0513859.9

In another embodiment the host cell is the same genus as the native host species, i.e. the recombinant gene is re-introduced and expressed in a species from the same genus as the species from which the recombinant gene was isolated.

In another embodiment the host cell is the native host species, i.e. the recombinant gene is re-introduced and expressed in the same species from which the recombinant gene was isolated.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known, The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol [*1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R.(Editors) *Aspergillus:* 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit. Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27), or in WO01/16308.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (Bacillus).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be described, by way of example only, with reference to the following figures and examples.

Figure 3:
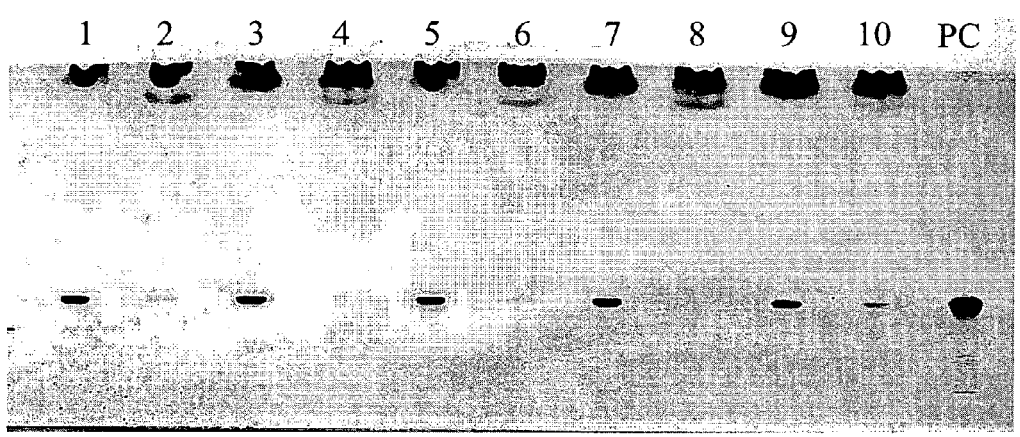
Figure 4:
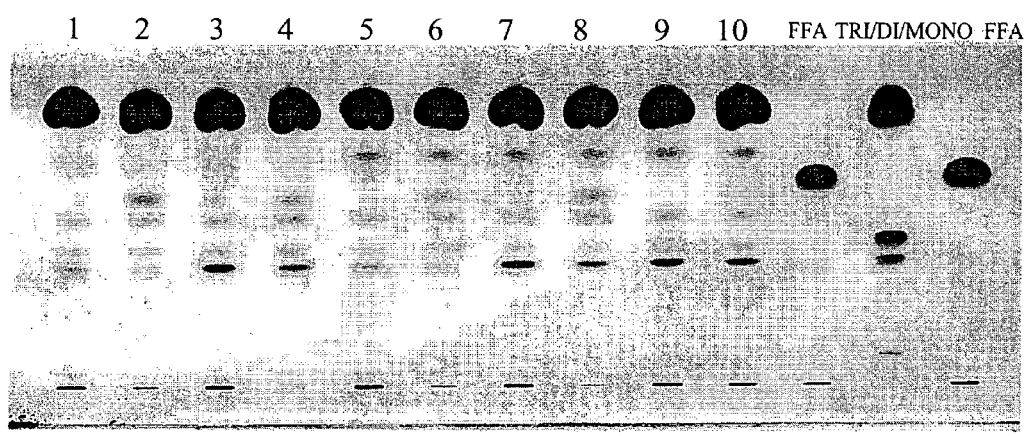
Figure 5:
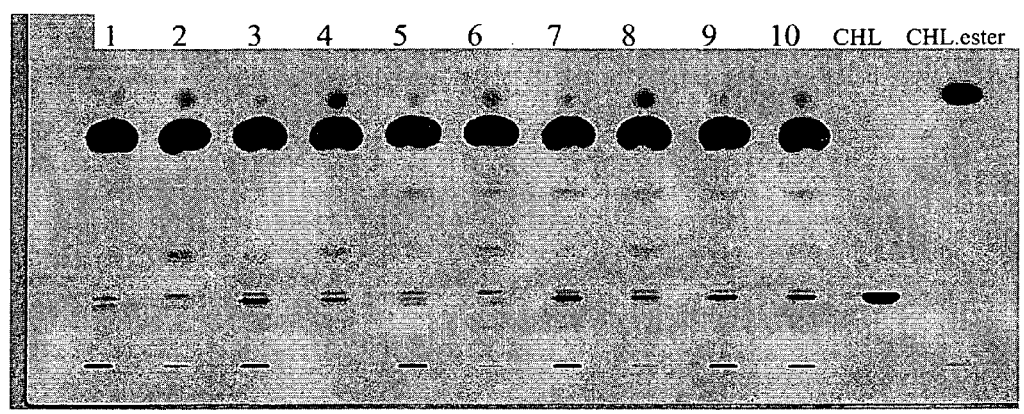
Figure 6:
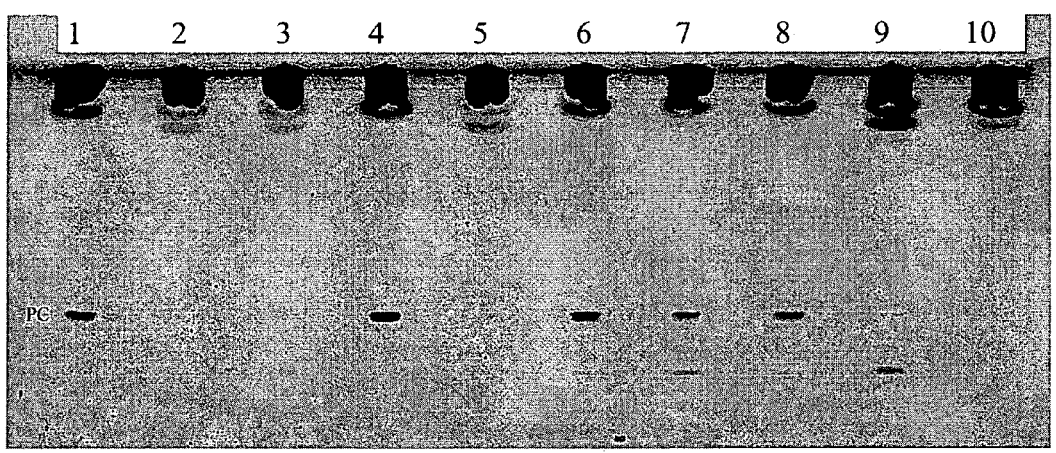
Figure 7:
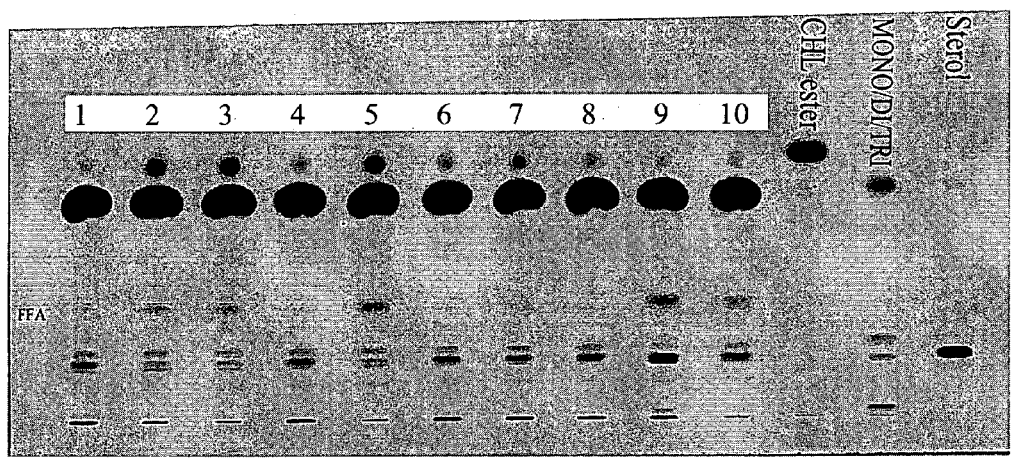
Figure 8:
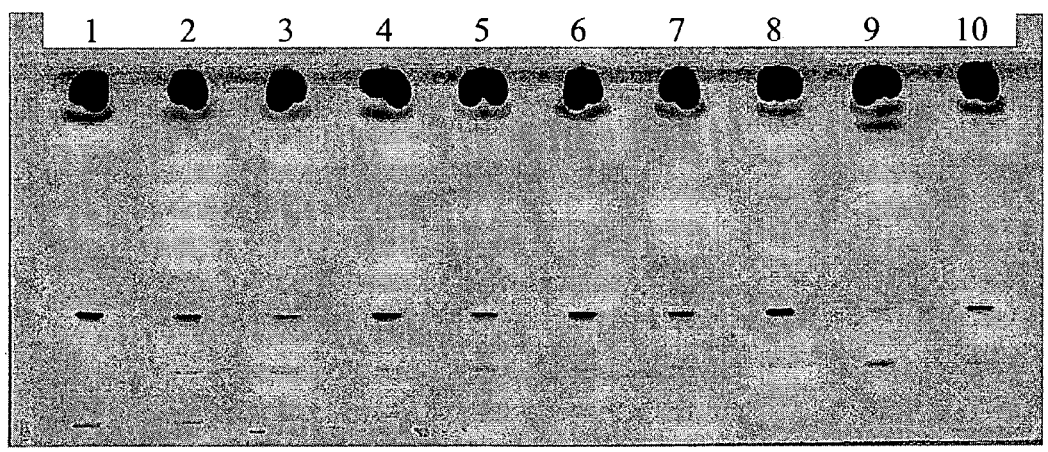
Figure 9:
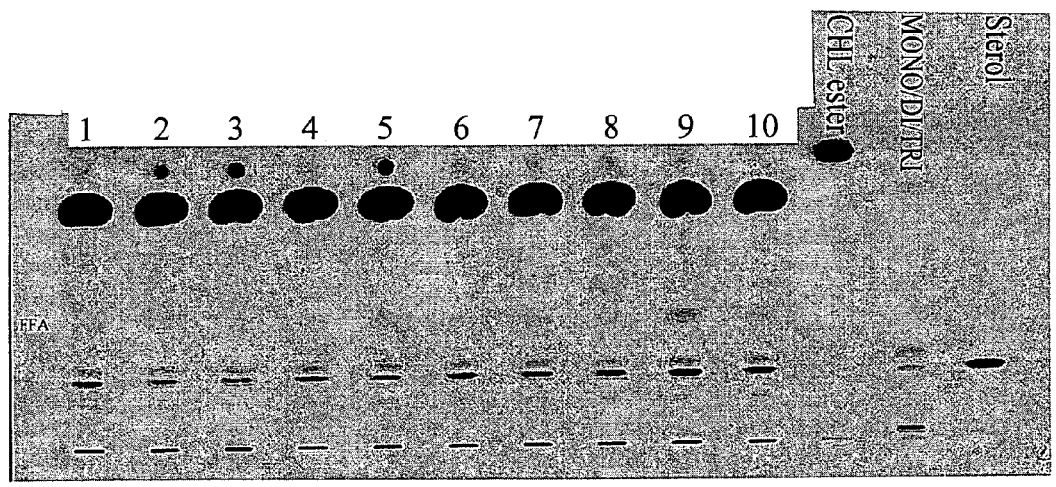
Figure 26:
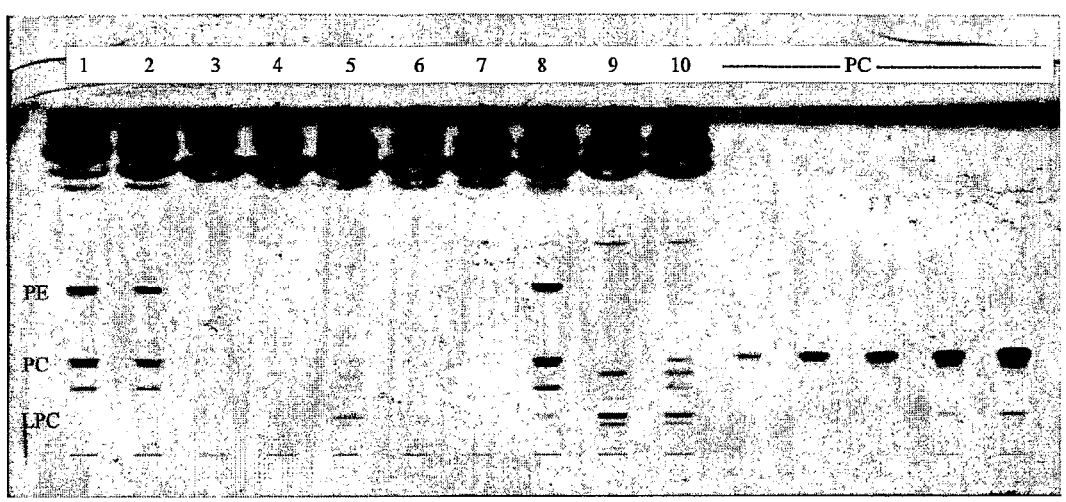

Lane 1. Lipid acyltransferase sample after desalting, 40 μl was applied to the gel Lane 2. Lipid acyltransferase sample after desalting, 10 μl was applied to the gel Lane 3. Purified Lipid acyltransferase lipase after IEC (pool 27-39), 40 μl was applied to the gel Lane 4. Purified Lipid acyltransferase lipase after IEC (pool 27-39, 10 μl was applied to the gel;

FIG. 3 shows a TLC (Solvent 4) of reaction products from the lipid acyltransferase treatment of soya bean oil samples according to Table 2. As a reference phosphatidylcholine (PC) was also analysed;

FIG. 4 shows a TLC (Solvent 1) of reaction products from the lipid acyltransferase treatment of soya bean oil samples according to Table 2. As reference free fatty acid (FFA) and Mono-di-triglyceride (TRI/DI/MONO) were also analysed;

FIG. 5 shows a TLC (Solvent 5) of reaction products from the lipid acyltransferase treatment of soya bean oil samples according to Table 2. As reference Cholesterol (CHL) and Cholesterolester (CHL-ester) were also analysed;

FIG. 6 shows a TLC (Solvent 4) of reaction products from the lipid acyltransferase or Lecitase Ultra™ treatment of soya bean oil samples according to Table 3 for 20 hours;

FIG. 7 shows a TLC (Solvent 5) of reaction products from the lipid acyltransferase or Lecitase Ultra™ treatment of soya bean oil samples according to Table 3 for 20 hours. Cholesterol ester (CHL ester); Mono-di-Triglyceride(MONO/DI/TRI) and plant sterol were also analysed as references. Identification of free fatty acid (FFA) is also indicated;

FIG. 8 shows a TLC (Solvent 4) of reaction products from the lipid acyltransferase or Lecitase Ultra™ treatment of soya bean oil samples according to Table 3 for 4 hours;

FIG. 9 shows a TLC (Solvent 5) of reaction products from the lipid acyltransferase or Lecitase Ultra™ treatment of soya bean oil samples according to Table 3 for 4 hours. Cholesterol ester (CHL ester); Mono-di-Triglyceride (MONO/DI/TRI) and plant sterol were also analysed as references. Identification of free fatty acid (FFA) is also indicated;

FIG. 10 shows the amino acid sequence of a mutant *Aeromonas salmonicida* mature lipid acyltransferase (GCAT) with a mutation of Asn80Asp (notably, amino acid 80 is in the mature sequence);

FIG. 11 shows an amino acid sequence (SEQ ID No. 1) a lipid acyl transferase from *Aeromonas hydrophila* (ATCC #7965);

FIG. 12 shows a pfam00657 consensus sequence from database version 6 (SEQ ID No. 2);

FIG. 13 shows an amino acid sequence (SEQ ID No. 3) obtained from the organism *Aeromonas hydrophila* (P10480; GI:121051);

FIG. 14 shows an amino acid sequence (SEQ ID No. 4) obtained from the organism *Aeromonas salmonicida* (AAG098404; GI:9964017);

FIG. 15 shows an amino acid sequence (SEQ ID No. 5) obtained from the organism *Streptomyces coelicolor* A3(2) (Genbank accession number NP_631558);

FIG. 16 shows an amino acid sequence (SEQ ID No. 6) obtained from the organism *Streptomyces coelicolor* A3(2) (Genbank accession number: CAC42140);

FIG. 17 shows an amino acid sequence (SEQ ID No. 7) obtained from the organism *Saccharomyces cerevisiae* (Genbank accession number P41734);

FIG. 18 shows an amino acid sequence (SEQ ID No. 8) obtained from the organism *Ralstonia* (Genbank accession number: AL646052);

FIG. 19 shows SEQ ID No. 9. Scoe1 NCBI protein accession code CAB39707.1 GI:4539178 conserved hypothetical protein [*Streptomyces coelicolor* A3(2)];

FIG. 20 shows an amino acid shown as SEQ ID No. 10. Scoe2 NCBI protein accession code CAC01477.1 GI:9716139 conserved hypothetical protein [*Streptomyces coelicolor* A3(2)];

FIG. 21 shows an amino acid sequence (SEQ ID No. 11) Scoe3 NCBI protein accession code CAB88833.1 GI:7635996 putative secreted protein. [*Streptomyces coelicolor* A3(2)];

FIG. 22 shows an amino acid sequence (SEQ ID No. 12) Scoe4 NCBI protein accession code CAB89450.1 GI:7672261 putative secreted protein. [*Streptomyces coelicolor* A3(2)];

FIG. 23 shows an amino acid sequence (SEQ ID No. 13) Scoe5 NCBI protein accession code CAB62724.1 GI:6562793 putative lipoprotein [*Streptomyces coelicolor* A3(2)];

FIG. 24 shows an amino acid sequence (SEQ ID No. 14) Srim1 NCBI protein accession code AAK84028.1 GI:15082088 GDSL-lipase [*Streptomyces rimosus*];

FIG. 25 shows an amino acid sequence (SEQ ID No. 15) of a lipid acyltransferase from *Aeromonas salmonicida* subsp. *Salmonicida* (ATCC#14174);

FIG. 26 shows a TLC (solvent 4) of sample 1 to 10 of crude soya oil treated 20 hours with enzymes according to Table 4. PC is phosphatidylcholine added in 5 different concentrations (reference material).

Figure 27:
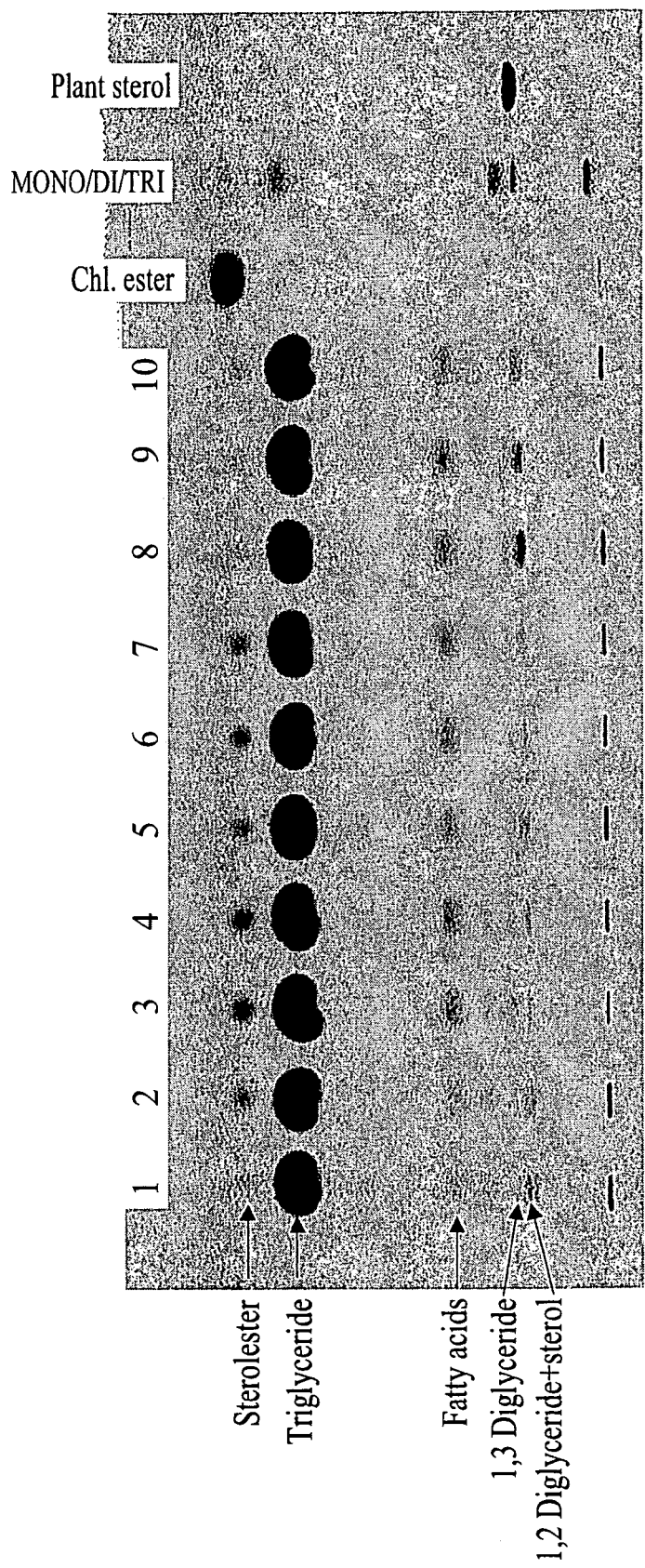

FIG. 27 shows a TLC (Solvent 5) of reaction products from lipid acyl transferase or Lecitase Ultra™ treatment of crude soya oil samples according to Table 4 (20 hours). Cholesterol ester (CHL-ester), Mono-di-Triglyceride (MONO/DI/TRI), and plant sterol were also analysed as references. Identification of free fatty acid is also indicated.

FIG. 28 shows SEQ ID No 17 which is the amino acid sequence of a lipid acyltransferase from *Candida parapsilosis*;

FIG. 29 shows SEQ ID No 18 which is the amino acid sequence of a lipid acyltransferase from *Candida parapsilosis*;

FIG. 30 shows alignment 1;

FIG. 31 shows SEQ ID No. 19. Scoe1 NCBI protein accession code CAB39707.1 GI:4539178 conserved hypothetical protein [*Streptomyces coelicolor* A3(2)];

FIG. 32 shows an amino acid sequence (SEQ ID No. 25) of the fusion construct used for mutagenesis of the *Aeromonas hydrophila* lipid acyltransferase gene. The underlined amino acids is a xylanase signal peptide;

FIG. 33 shows a polypeptide sequence of a lipid acyltransferase enzyme from *Streptomyces* (SEQ ID No. 26);

FIG. 34 shows a polypeptide sequence of a lipid acyltransferase enzyme from *Thermobifida*_(SEQ ID No. 27);

FIG. 35 shows a polypeptide sequence of a lipid acyltransferase enzyme from *Theimobifida*_(SEQ ID No. 28);

FIG. 36 shows a polypeptide of a lipid acyltransferase enzyme from *Corynebacterium efficiens* GDSx 300 amino acid_(SEQ ID No. 29);

FIG. 37 shows a polypeptide of a lipid acyltransferase enzyme from *Novosphingobium aromaticivorans* GDSx 284 amino acid_(SEQ ID No. 30);

FIG. 38 shows a polypeptide of a lipid acyltransferase enzyme from *Streptomyces coelicolor* GDSx 269 aa (SEQ ID No. 31)

Figure 41:
Figure 42:
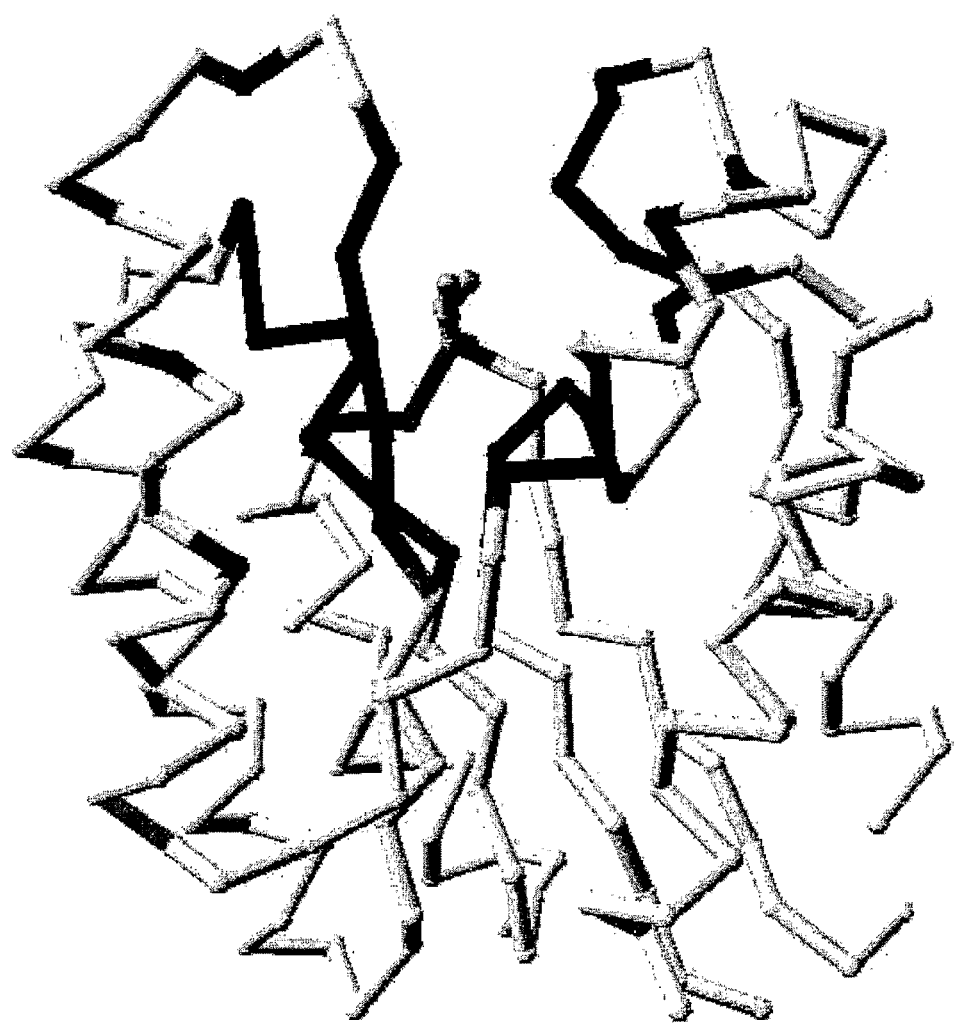

FIG. 39 shows a polypeptide of a lipid acyltransferase enzyme from *Streptomyces avermitilis*\GDSx 269 amino acid (SEQ ID No. 32);

FIG. 40 shows a polypeptide of a lipid acyltransferase enzyme from *Streptomyces* (SEQ ID No. 33);

FIG. 41 shows a ribbon representation of the 1IVN.PDB crystal structure which has glycerol in the active site. The Figure was made using the Deep View Swiss-PDB viewer;

FIG. 42 shows 1IVN.PDB Crystal Structure—Side View using Deep View Swiss-PDB viewer, with glycerol in active site—residues within 10 Å of active site glycerol are coloured black;

FIG. 43 shows alignment 2;

FIG. 44 shows an amino acid sequence (SEQ ID No. 34) obtained from the organism *Aeromonas hydrophila* (P10480; GI: 121051) (notably, this is the mature sequence).

FIG. 45 shows the amino acid sequence (SEQ ID No. 35) of a mutant *Aeromonas salmonicida* mature lipid acyltransferase (GCAT) (notably, this is the mature sequence)

FIG. 46 shows a nucleotide sequence (SEQ ID No. 36) from *Streptomyces thermosacchari*

FIG. 47 shows an amino acid sequence (SEQ ID No. 37) from *Streptomyces thermosacchari*

FIG. 48 shows an amino acid sequence (SEQ ID No. 38) from *Thermobifida fusca*/GDSx 548 amino acid FIG. 49 shows a nucleotide sequence (SEQ ID No. 39) from *Thermobifida fusca*

FIG. 50 shows an amino acid sequence (SEQ ID No. 40) from *Thermobifida fusca*/GDSx FIG. 51 shows an amino acid sequence (SEQ ID No. 41) from *Corynebacterium efficiens*/GDSx 300 amino acid FIG. 52 shows a nucleotide sequence (SEQ ID No. 42) from *Corynebacterium efficiens*

FIG. 53 shows an amino acid sequence (SEQ ID No. 43) from *S. coelicolor*/GDSx 268 amino acid FIG. 54 shows a nucleotide sequence (SEQ ID No. 44) from *S. coelicolor*

FIG. 55 shows an amino acid sequence (SEQ ID No. 45) from *S. avermitilis*

FIG. 56 shows a nucleotide sequence (SEQ ID No. 46) from *S. avermitilis*

Figure 59:
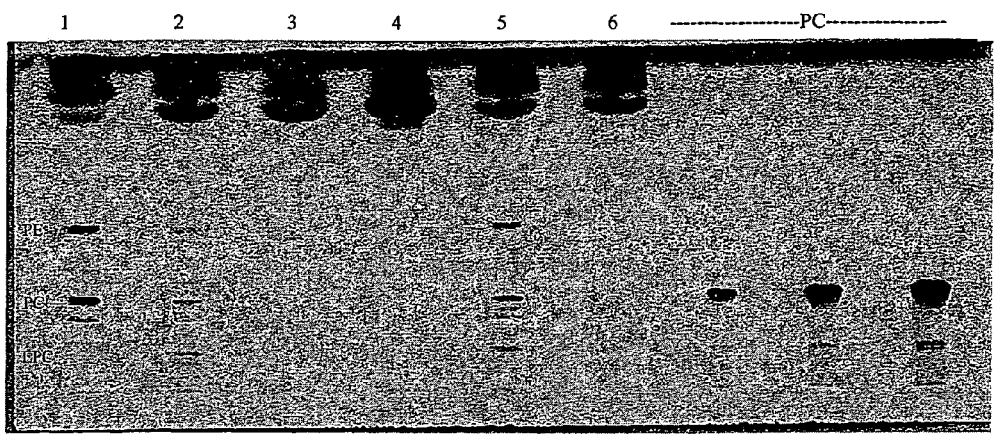

FIG. 57 shows an amino acid sequence (SEQ ID No. 47) from *Thermobifida fusca*/GDSx FIG. 58 shows a nucleotide sequence (SEQ ID No. 48) from *Thermobifida fusca*/GDSx FIG. 59 shows TLC (Solvent 4) of reaction products from enzyme treatment of crude soya oil samples according to table 6. As reference, phosphatidylcholine (PC) was also analysed. PE (phosphatydylethanolamine(PE) and lysophosphatidylcholine (LPC) are also indicated.

Figure 60:
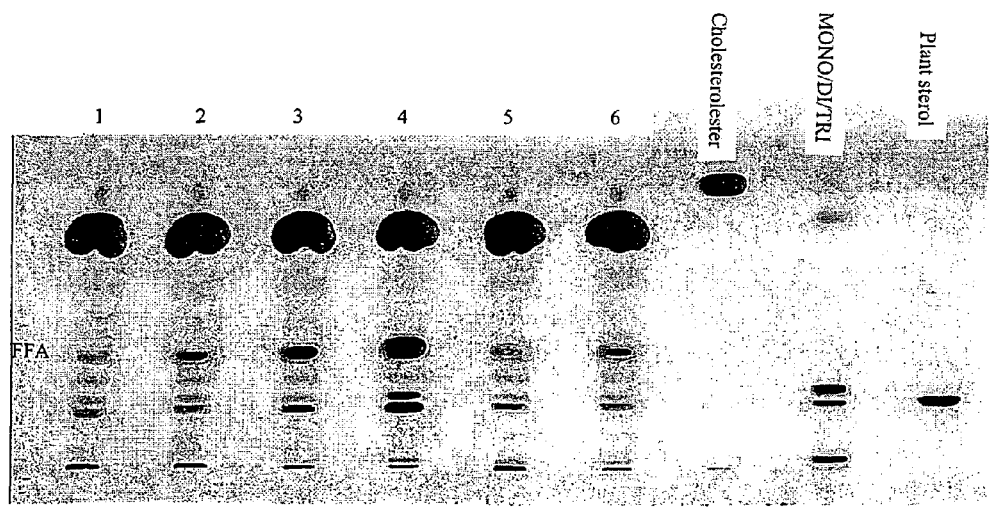

FIG. 60 shows TLC (Solvent 5) of reaction products from enzyme treatment of crude soya oil samples according to table 6. References Cholesterolester, mono-di-triglyceride and plant sterol. Free fatty acid (FFA) is also indicated FIG. 61 shows an alignment of the L131 and homologues from *S. avermitilis* and *T. fusca* illustrates that the conservation of the GDSx motif (GDSY in L131 and *S. avermitilis* and *T. fusca*), the GANDY box, which is either GGNDA or GGNDL, and the HPT block (considered to be the conserved catalytic histadine). These three conserved blocks are highlighted

EXAMPLES

The purpose of this study was to investigate the possible use of a lipid acyltransferase (sometimes referred to herein as a glycerophospholipid Cholesterol Acyl-Transferase (GCAT)) for degumming of vegetable oil like soya bean oil, sunflower oil and rape seed oil.

One purpose of this study was to investigate whether in particular a lipid acyltransferase mutant (N80D) is a more suitable enzyme for degumming. From earlier studies it is known that lipid acyltransferases (particularly GCATs) catalyse the acyl-transfer of fatty acid from phospholipid to sterols to form lysolecithin and sterol esters.

The present study was conducted in a model based on refined soya bean oil where phosphatidylcholine and plant sterols were added. This model was selected because it is easier to analyse reaction product in a model system instead of using crude soya oil.

Enzymatic degumming processes of plant oils including soya oil and rape seed oil is expanding in recent years because this process is a cheaper and better process to remove lecithins from oil. The enzyme used for oil degumming is a phospholipase A1 (Lecitase Ultra™ or pancreatic phospholipase A2—Novozymes A/S, Denmark).

One advantage of the enzyme of the present invention when used in degumming compared with prior art phospholipase A1 is that the enzyme according to the present invention facilitates the formation of sterol esters during the degumming process and contributes to the accumulation of sterol esters, which is not achieved with the currently used phospholipase A1 (Lecitase Ultra™).

Materials and Methods.
Enzymes
Lipid acyltransferase according to the present invention: *Aeromonas salmonicidae* enzyme with a mutation Asn80Asp (amino acid 80 of the mature enzyme) (SEQ ID No. 16 (see FIG. 10));
Lecitase Ultra (#3108) from Novozymes, Denmark
Soya bean oil: Soya olie IP (Item No. 005018/batch nr T-618-4)
Lecithin: L-α Phosphatidylcholine 95% Plant (Avanti #441601)
Plant Sterol Generol 122 N from Henkel, Germany.
Tocopherol: Alpha-tocopherol (Item no. 0.050908/lot.nr 4010140554)
Phospholipase Activity
Substrate
0.6% L-α Phosphatidylcholine 95% Plant (Avanti #441601), 0.4% Triton-X 100 (Sigma X-100) and 5 mM $CaCl_2$ was dissolved in 0.05M HEPES buffer pH 7.
Assay Procedure:
400 μl substrate was added to an 1.5 ml Eppendorf tube and placed in an Eppendorf Thermomixer at 37° C. for 5 minutes. At time T=0 min, 50 μl enzyme solution was added. Also a blank with water instead of enzyme was analyzed. The sample was mixed at 10*100 rpm in an Eppendorf Thermomixer at 37° C. for 10 minutes. At time T=10 min the Eppendorf tube was placed in another thermomixer at 99° C. for 10 minutes to stop the reaction.
Free fatty acid in the samples was analyzed by using the NEFA C kit from WAKO GmbH.
Enzyme activity PLU-NEFA pH 7 was calculated as micromole fatty acid produced per minute under assay conditions.
HPTLC
Applicator: Automatic TLC Sampler 4, CAMAG
HPTLC plate: 20×10 cm, Merck no, 1.05641. Activated 30 min. at 160° C. before use.
Application: 1 μl of a 8% solution of oil in buffer is applied to the HPTLC plate using Automatic TLC applicator.
Running buffer 1: P-ether:Methyl-tert-butyl-ether:Acetic acid 60:40:1
Running buffer 4: Chloroform:Methanol:Water 75:25:4
Running buffer 5: P-ether: Methyl-tert-butylether: Acetic acid 70:30:1
Application/Elution time: Running buffer 1:12 min
Running buffer 4:20 min
Running buffer 5:10 min
Developing
The plate is dried in an oven at 160° C. for 10 minutes, cooled, and dipped into 6% cupri acetate in 16% $H_3PO_4$. Dried additionally 10 minutes at 160° C. and evaluated directly.

Example 1

Enzyme Purification

Sample: The sample lipid acyltransferase (Asn80Asp) (SEQ ID No. 16) was filtered through 0.8/0.22 μm filter. 510 ml filtrate was collected.
Step 1. Desalting, Sephadex 25 G, 3.21 Gel (10 cm id)
The Sephadex column was prepared as described by the manufacturer (Amersham biosciences). The column was equilibrated with 20 mM Na-P-buffer, pH 8.0. The sample (510 ml) was applied to the column at a flow rate of 25 ml/min. 815 ml desalted sample was collected and kept at +4° C.

Step 2. Anion exchange chromatography, Q-Sepharose FF 300 ml gel (XK 50) Q-Sepharose PF column was prepared as described by the manufacturer (Amersham biosciences). The column was equilibrated with 20 mM Na-P-buffer, pH 8.0. The desalted sample was applied to the column at a flow rate of 15 ml/min. The column was then washed with buffer A. The lipase was eluted with a linear gradient of 0-0.4 M NaCl in 20 mM Na-P-buffer (pH 8.0, buffer B). Fractions of 15 ml were collected during the entire run. The lipase was eluted at approx. 0.2 M NaCl, and no lipase activity was detected in running through fractions.

Enzyme Assay Based on PNP-Caprylate

The assay was performed using PNP-Capylate as substrate as follows:

10 mg of substrate solved in 1 ml ethanol and was mixed with 9 ml of 50 mM Tris-HCL buffer (pH 7.3) containing 0.4% TX100.

240 μl of substrate was pre-incubated at 35 degree C. The reaction was initiated by the addition of 25 μl of sample/blank. The mixture was incubated at 35° C. for 5 min with shaking. Using a spectrophotometer, the formation of PNP was measured continually at 410 nm. The blank run contains all the components with buffer instead of sample. One unit of lipase activity was defined as the amount of enzyme releasing 1 μl of free caprylic acid per minute at 35° C.

Determination of molecule weight and purity.

SDS-PAGE was carried out on a 4-12% Nu-PAGE gel (+DTT) and Coomassie stained according to the manufacturers instructions (Novex, USA). The standard marker was See Blue Plus2 and was obtained from Novex, USA.

Results

Figure 1:
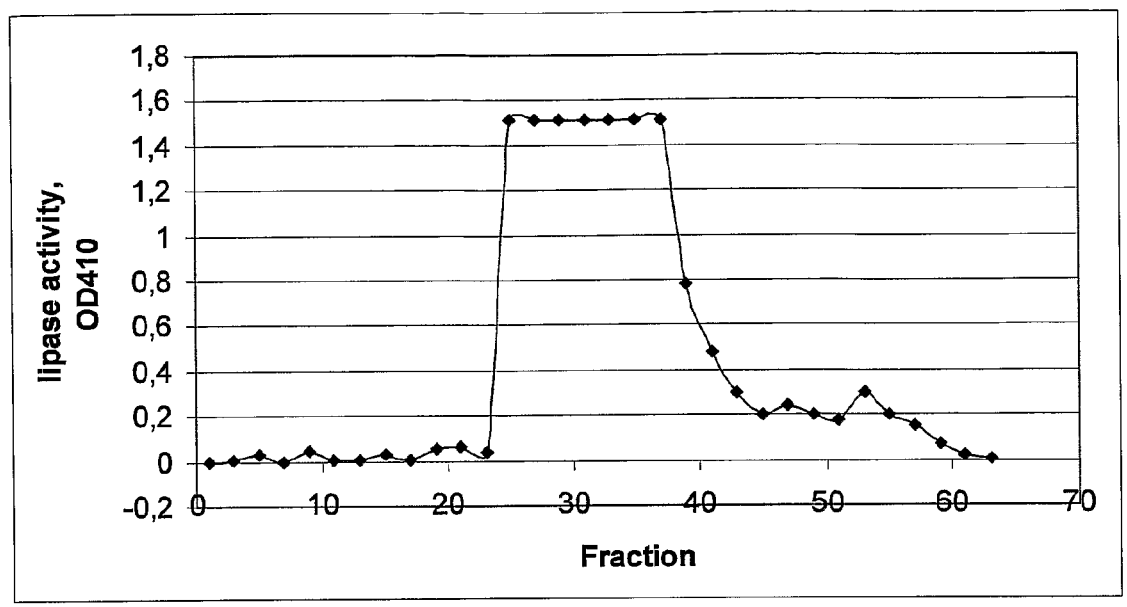
FIG. 1 shows the profile of the lipid acyltransferase activity (PNP-caprylate assay) obtained after anion exchange chromatography (IEC)

The chromatogram from Ion Exchange Chromatography (IEC) purification of the lipid acyltransferase mutant N80D is shown in FIG. 1. The fractions collected were analyzed for lipase activity (based on PNP-Caprylate assay). The activity of the fractions is illustrated in FIG. 1-*a*.

The fractions containing lipid acyltransferase activity (27-39, 195 ml) were pooled. The final recovery of the partly purified lipid acyltransferase was approx. 80% (based on pNP-Caprylate assay).

Fractions of the purified lipid acyltransferase were subjected to SDS-PAGE gel electrophoresis.

Figure 2:
FIG. 2 shows the results of SDS-PAGE analyses of purified the lipid acyltransferase fractions (4-12% Mes, +DTT, 40/10 μl sample was applied to the gel)

The SDS-PAGE gel revealed lipid acyltransferase protein with a molecular weight of approx. 28 KDa. The partly purified lipid acyltransferase contained a minor impurity at approx 10 KDa (see FIG. 2).

The lipid acyltransferase pool 27-39 after IEC was analysed for phospholipase activity with the result of 20.4 PLU-7/ml.

The overall purification scheme is presented in Table 1, in which the lipid acyltransferase was partly purified with a recovery of 80%.

TABLE 1

Purification of the lipid acyltransferase

| Sample | Vol. | $V_{Max}$ | Dilution | Tot. Units | % Recovery |
|---|---|---|---|---|---|
| Crude (Q3 + Q4) | 510 | 1.150 | 100 | 58650 | 100 |
| Desalted crude | 815 | 0.697 | 100 | 56806 | 97 |
| Pool 27-39, Q-Sep. | 195 | 1.203 | 200 | 46898 | 80 |

Example 2

Degumming Experiment

The lipid acyltransferase sample from Example 1 was used for degumming studies in the formulations shown in Table 2.

Plant sterol, alpha-tocopherol and phosphatidylcholine were dissolved in soya bean oil by heating the oil to 90° C. The oil was then cooled to approx 40° C. and the enzyme was added. The sample was placed at 40° C. for 17 hours during agitation and then a sample was taken out for HPTLC analysis by dissolving the sample in Chloroform:Methanol 2:1.

TABLE 2

Soya bean oil models with alpha-tocopherol and plant sterol, used for testing of the lipid acyltransferase.

| | | 1 | 2 | 3 | 4 | 5 | 6 | 7 | 8 | 9 | 10 |
|---|---|---|---|---|---|---|---|---|---|---|---|
| Soya bean oil | % | 98 | 97 | 97 | 96 | 97 | 96 | 96 | 95 | 96 | 92 |
| Alpha-tocopherol | % | | | | | 1 | 1 | 1 | 1 | 1 | 1 |
| Plant Sterol | % | | | 1 | 1 | | | 1 | 1 | 1 | 1 |
| Phosphatidylcholine | % | 2 | 2 | 2 | 2 | 2 | 2 | 2 | 2 | 2 | 2 |
| lipid acyltransferase pool 27-39 | % | | 1 | | 1 | | 1 | | 1 | | 4 |

The results from the HPTLC analysis are shown in FIG. 3 and FIG. 4.

The TLC results shown in FIG. 3 clearly show that phosphatidylcholine is almost 100% removed by adding the lipid acyltransferase to the oil. Only sample no. 10 contains small amount of phosphatidylcholine. Sample no. 10 has the highest amount of water, which indicates that for degumming the enzyme may work better in low water formulations, or it could be explained by the fact that because sample no. 10 contain 5% water a two-phase system is formed, which might cause less contact between the reactants and the enzyme.

From the results shown in FIG. 4 is was observed that small amount of fatty acids are formed, but when sterol or alpha-tocopherol is also available in the oil the amount of free fatty acids is lower, because the fatty acids from phosphatidylcholine it transferred to the sterol or tocopherol to form sterol-esters and tocopherol-esters.

The formation of sterol esters is clearly seen from the TLC results shown in FIG. 5. It should be noted that the reference material used, cholesterol ester, has the same retention time as plant-sterol-esters.

Example 3

Degumming Experiment (2)

In another experiment the lipid acyltransferase pool 27-39 from IEC chromatography, was tested at different enzyme dosages and water concentrations in soya bean oil with phosphatidylcholine and plant sterol. In this experiment a commercial phospholipase Lecitase Ultra™ was also tested in a concentration recommended by the supplier for degumming. The composition of the samples for this experiment are shown in Table 3.

TABLE 3

Soya bean oil model with plant sterol used for testing of the lipid acyltransferase, and Lecitase Ultra ™.

|  |  | 1 | 2 | 3 | 4 | 5 | 6 | 7 | 8 | 9 | 10 |
|---|---|---|---|---|---|---|---|---|---|---|---|
| Soya bean oil | % | 96.6 | 96.6 | 96 | 92 | 96 | 92 | 95 | 92 | 96 | 92 |
| Plant Sterol | % | 1 | 1 | 1 | 1 | 1 | 1 | 1 | 1 | 1 | 1 |
| Phosphatidylcholine | % | 2 | 2 | 2 | 2 | 2 | 2 | 2 | 2 | 2 | 2 |
| Lipid acyltransferase pool 27-39 | % |  | 0.4 | 0.4 | 0.4 | 1 | 1 | 2 | 2 |  |  |
| Lecitase Ultra ™, 1% solution | % |  |  |  |  |  |  |  |  | 0.3 | 0.3 |
| Water |  | 0.4 |  | 0.6 | 4.6 | 0 | 4 | 0 | 3 | 0.7 | 4.7 |
| Units/g oil (PLU-7/g) |  | 0 | 0.08 | 0.08 | 0.08 | 0.2 | 0.2 | 0.4 | 0.4 | 1.03 | 1.03 |

Plant sterol and phosphatidylcholine were dissolved in soya bean oil by heating to 95° C. during agitation. The oil was then cooled to 40° C. and the enzymes were added. The sample was maintained at 40° C. with magnetic stirring and samples were taken out after 4 and 20 hours and analysed by TLC. The results from the HPTLC analysis of samples taken out after 4 and 20 hours are shown in FIGS. 6 to 9.

The HPTLC results indicate that the lowest dosage of the lipid acyltransferase (0.4% corresponding to 0.08 PLU-7/g oil) is sufficient to remove phosphatidylcholine in soya bean oil after 20 h reaction time. It is also observed that the highest dosage of water (5%) seems to have a detrimental effect on the lipid acyltransferase for the hydrolysis of phosphatidylcholine in the oil. It is therefore expected that the lower degree of hydrolysis in the sample with highest dosage of the lipid acyltransferase conversion is explained by that fact that more water is also added to the sample. Contrary to this it is observed that Lecitase Ultra™ has a lower degree of hydrolysis of phosphatidylcholine in the lowest dosage of water (1%), whereas Lecitase Ultra™ almost completely removes phosphatidylcholine in the sample with 5% water.

The results from FIG. 7 also indicate that the main part of the plant sterol is converted to plant sterol ester in samples treated with the lipid acyltransferase whereas no sterol esters are formed in the samples treated with Lecitase Ultra™. FIG. 7 indicates that Lecitase Ultra™ produce more free fatty acids (FFA) than the lipid acyltransferase.

Conclusion

Degumming experiments with a model soya bean oil containing phosphatidylcholine, plant sterol and tocopherol has shown that a partially purified lipid acyltransferase enzyme is able to remove all phosphatidylcholine concomitant with the formation of plant sterol esters, and only to a small extent free fatty acids are formed.

One further advantage of the lipid acyltransferase is the formation of sterol esters, and in particular tocopherol ester, because sterols esters (including tocopherol ester) provide beneficial health properties. In conventional edible oil processing, following degumming the aqueous phase containing the hydrolysed polar lipid (e.g. phospholipid and/or glycolipid) is separated from the oil. Conventionally sterols are removed from the edible oil during the oil refining process (this is sometimes referred to as deodorising). However, the sterol esters (and tocopherol ester) resist deodorisation and thus remain in the oil. Accumulation of sterol esters in the oil is attractive because it has been shown that higher intake of plant sterol esters reduces the risk for cardiovascular diseases in humans.

The experiment also indicates that the lipid acyltransferase is able to make tocopherol esters, which will also accumulate in the oil.

This will contribute to improved oxidative stability of the oil and thus is a further benefit to using the lipid acyltransferase in accordance with the present invention for degumming.

Example 4

Degumming Experiment in Crude Oil

In another experiment, the lipid acyltransferase pool 27-39 from IEC chromatography was tested at different enzyme dosages and water concentrations in crude soya oil (before degumming) obtained from The Solae Company, Aarhus, Denmark. In this experiment, a commercial phospholipase Lecitase Ultra™ was also tested in a concentration recommended for degumming by the supplier. The composition of the samples for this experiment is shown in Table 4.

The samples were placed in a heating block at 40° C. during agitation with a magnetic stirrer. Samples were taken out after 20 hours for analysis.

TABLE 4

|  |  | 1 | 2 | 3 | 4 | 5 | 6 | 7 | 8 | 9 | 10 |
|---|---|---|---|---|---|---|---|---|---|---|---|
| Crude soya oil | % | 99.5 | 99.5 | 99 | 98 | 97 | 98 | 95 | 99.7 | 99 | 95 |
| Lipid Acyltransferase | % |  | 0.5 | 1 | 1 | 1 | 2 | 5 |  |  |  |
| Lecitase Ultra ™ #3108, 1% solution | % |  |  |  |  |  |  |  | 0.3 | 0.3 | 0.3 |
| Water | % | 0.5 | 0 | 0 | 1 | 2 | 0 | 0 | 0 | 0.7 | 4.7 |

The oil samples were analysed by HPTLC with the results shown in FIGS. 26 and 27.

The TLC analysis in FIG. 26 indicate that the lipid acyltransferase efficiently removes the phospholipids in crude soya oil without leaving any lysolecithin in the sample (sample 3, 4, 6 and 7). Lecitase Ultra™ also removes the phospholipid (PC), but some bands are remaining in the chromatogram, which is expected to be lysolecithin. It is also observed that lipid acyltransferase works in very low water environment, but Lecitase Ultra™ needs 1% to 5% water to work.

The results in FIG. 27 confirm that lipid acyl transferase converts the free sterol to sterolesters and Lecitase Ultra™ has no effect on sterols. FIG. 27 also indicates that some free fatty acids are formed both in samples with lipid acyl transferase and Lecitase Ultra™. The reason for the free fatty acid formation with lipid acyl transferase is explained by the fact that there is not enough acyl-donor (sterol) available, and therefore some hydrolysis also occurs.

Sample 1, 2, 3, 6, 8 and 10 from table 4 were analysed by GLC and the amount of sterol and sterol esters were quantified. The results are shown in Table 5.

TABLE 5

GLC analysis of sterol and sterol esters
In crude soya oil treated with enzyme (Table 4)

| Sample no | Enzyme | Sterol % | Sterol-ester % |
|---|---|---|---|
| 1 | Control | 0.25 | 0.07 |
| 2 | 0.5% Lipid acyltransferase pool 27-39 | 0.13 | 0.13 |
| 3 | 1% Lipid acyltransferase pool 27-39 | 0 | 0.26 |
| 6 | 2% Lipid acyltransferase pool 27-39 | 0 | 0.22 |
| 8 | 0.3% Lecitase Ultra ™ 1% solution | 0.25 | 0.03 |
| 10 | 0.3% Lecitase Ultra ™ 1% solution + 5% water | 0.27 | 0.05 |

The results in Table 5 confirm the ability of the lipid acyl transferase of the present invention to convert all sterol in crude soya oil to sterol ester, and a commercial phospholipase Lecitase Ultra™ showed no effect on sterol.

Conclusion

The effect of the lipid acyl transferase of the present invention on crude soya oil confirms that the lipid acyl transferase of the present invention effectively removes phospholipids in the crude soya oil concomitant with the formation of sterol esters.

Example 5

In another experiment, phospholipase from *Streptomyces thermosacchari* L131 was tested in crude soya oil.

The results confirm that phospholipase *Streptomyces thermosacchari* L131 effectively hydrolyses phospholipids in crude soya oil and is a suitable alternative enzyme for degumming of plant oils.

Enzymatic degumming processes of plant oils including soya oil and rape seed oil are currently expanding because this process is a less expensive and better process to remove lecithins from plant oils. The enzyme commercially used for oil degumming is a microbial phospholipase A1 or an animal derived phospholipase A2.

A (phospho)lipid acyl transferase *Streptomyces thermosacchari* L131 is another enzyme, which can be used for degumming.

Introduction

The purpose of this study was to investigate the possible use of a lipid acyltransferase from *Streptomyces thermosacchari* L131 for degumming of vegetable oil like soya oil, sunflower oil, and rape seed oil.

Traditionally, two processes have been used for degumming of oils, namely the physical degumming and the chemical degumming. Back in the 1990'es, the enzymatic degununing process was developed, based on the use of pancreatic phospholipase. Because this enzyme was non-kosher, the phospholipase was substituted by microbial phospholipase A1. The enzymatic process has several advantages over the chemical or the physical degumming processes including cost savings, higher yield, and a more environmentally desirable process.

The purpose of this study was to investigate whether lipid acyltransferase from *Streptomyces thermosacchari* L131 would be a suitable enzyme for degumming. From the studies described above *Streptomyces thermosacchari* L131 is known to have hydrolytic properties against galactolipids and phospholipids without showing any activity on triglycerides, and it is expected that this enzyme also facilitates transferase reactions in certain environments with low water content. This study was conducted in crude soya oil with the natural content of phospholipids.

Materials and Methods

Enzyme

K371(jour 2390-30): *Streptomyces thermosacchari* L131/*S. lividans* freeze dried on starch.

(Activity: 108 PLU-7/g).

Lecitase Ultra (#3108) from Novozymes, Denmark
Cholesterolester, Fluka 26950
Plant Sterol Generol 122 N from Henkel, Germany
Crude soya oil from The Solae Company, Aarhus Denmark
Lecithin: L-α Phosphatidylcholine 95% Plant (Avanti #441601)

Phospholipase Activity

Substrate:

0.6% L-α Phosphatidylcholine 95% Plant (Avanti #441601), 0.4% Triton-X 100 (Sigma X-100), and 5 mM $CaCl_2$ were dissolved in 0.05M HEPES buffer pH 7.

Assay Procedure:

400 μl substrate was added to a 1.5 ml Eppendorf tube and placed in an Eppendorf Thermomixer at 37° C. for 5 minutes. At time T=0 min, 50 μl enzyme solution was added. Also a blank with water instead of enzyme was analyzed. The sample was mixed at 10*100 rpm in an Eppendorf Thermomixer at 37° C. for 10 minutes. At time T=10 min the reaction was stopped by placing the Eppendorf tube in another thermomixer at 99° C. for 10 minutes.

The free fatty acid content of samples was analyzed by using the NEFA C kit from WAKO GmbH.

Enzyme activity PLU-NEFA pH 7 was calculated as micromole fatty acid produced per minute under assay conditions.

GLC (Gas Chromatography)

Perkin Elmer 8420 Capillary Gas Chromatography equipped with WCOT fused silica column 12.5 m×0.25 mm ID×0.1 μm 5%/phenyl-methyl-silicone (CP Sil 8 CB from Crompack).

| Carrier: Helium. Injection: 1.5 μL with split. Detector: FID. 385° C. | | | | |
|---|---|---|---|---|
| | Oven program: | | | |
| | 1 | 2 | 3 | 4 |
| Oven temperature [° C.] | 80 | 200 | 240 | 360 |
| Isothermal, time [min] | 2 | 0 | 0 | 10 |
| Temperature rate [° C./min] | 20 | 10 | 12 | |

Sample preparation: Lipid extracted from 0.2 gram sample was dissolved in 2 mL heptane:pyridine 2:1 containing an internal standard heptadecane, 2 mg/mL. 500 μL of the sample was transferred to a crimp vial. 100 μL MSTFA (N-Methyl-N-trimethylsilyl-trifluoracetamid) was added and the reaction incubated for 15 minutes at 90° C.
HPTLC
Applicator: Automatic TLC Sampler 4, CAMAG
HPTLC plate: 20×10 cm, Merck no. 1.05641. Activated 30 minutes at 160° C. before use.
Application: 1 μl of a 8% solution of oil in buffer was applied to the HPTLC plate using Automatic TLC applicator.
Running buffer 4: Chlorofonm:Methanol:Water 75:25:4
Running buffer 5: P-ether:Methyl-tert-butyl-ether: Acetic acid 70:30:1
  Application/Elution time:
  Running buffer 4:20 min
  Running buffer 5:10 min
Development
The plate was dried in an oven for 10 minutes at 160° C., cooled, and dipped into 6% cupri acetate in 16% $H_3PO_4$. Dried additionally 10 minutes at 160° C. and evaluated directly.
Results.
Degumming Experiment.
*Streptomyces thermosacchari* L131 was used for degumming studies in the formulations shown in table 6.
The samples were placed at 40° C. for 18 hours with agitation, after which time a sample was collected for HPTLC analysis by dissolving the sample in Chloroform:Methanol 2:1

TABLE 6

Degumming of crude soya oil with *Streptomyces thermosacchari* L131 And Lecitase Ultra

|  |  | 1 | 2 | 3 | 4 | 5 | 6 |
|---|---|---|---|---|---|---|---|
| Crude soya oil | % | 99 | 99 | 98 | 97 | 99.7 | 99 |
| K371, 10% in water | % |  | 1 | 2 | 3 |  |  |
| Lecitase Ultra ™ #3108, 1% in water | % |  |  |  |  | 0.3 | 0.3 |
| Water | % | 1 | 0 | 0 | 0 |  | 0.7 |

The results from the HPTLC analysis are shown in FIGS. 59 and 60.

FIG. 59 TLC (Solvent 4) of reaction products from enzyme treatment of crude soya oil samples according to table 6. As reference, phosphatidylcholine (PC) was also analysed. PE (phosphatydylethanolamine(PE) and lysophosphatidylcholine (LPC) are also indicated.

FIG. 60 TLC (Solvent 5) of reaction products from enzyme treatment of crude soya oil samples according to table 6. References Cholesterolester, monoglyceride, diglyceride, triglyceride and plant sterol. Free fatty acid (FFA) is also indicated The TLC results in FIG. 59 clearly show that phosphatidylcholine was completely removed by adding *Streptomyces thermosacchari* L131 to the oil. Only the lowest dosage (sample 2) did not completely hydrolyse the phospholipids. Lecitase Ultra™ also hydrolysed the phospholipids in the oil when 5% water was available (sample 6) but without adding extra water (sample 5) only part of the phospholipids were hydrolysed.

The results shown in FIG. 60 indicate that the hydrolysis of phospholipids is coincident with the formation of free fatty acid.

Conclusion.

The lipid acyltransferase from *Streptomyces thermosacchari* L131 effectively hydrolysis phospholipids in crude soya oil during formation of free fatty acids.

All publications mentioned in the above specification are herein incorporated by reference. Various modifications and variations of the described methods and system of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

---

SEQUENCE LISTING

```
<160> NUMBER OF SEQ ID NOS: 53

<210> SEQ ID NO 1
<211> LENGTH: 335
<212> TYPE: PRT
<213> ORGANISM: Aeromonas hydrophila

<400> SEQUENCE: 1

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Pro Tyr Tyr Glu Gly Arg Phe Ser Asn Gly Pro
        50                  55                  60

Val Trp Leu Glu Gln Leu Thr Lys Gln Phe Pro Gly Leu Thr Ile Ala
```

```
                65                  70                  75                  80
Asn Glu Ala Glu Gly Gly Ala Thr Ala Val Tyr Asn Lys Ile Ser
                    85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
        130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
                180                 185                 190

His Val Ser Ala Tyr His Asn Gln Leu Leu Leu Asn Leu Ala Arg Gln
            195                 200                 205

Leu Ala Pro Thr Gly Met Val Lys Leu Phe Glu Ile Asp Lys Gln Phe
        210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
        290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335

<210> SEQ ID NO 2
<211> LENGTH: 361
<212> TYPE: PRT
<213> ORGANISM: Artificial Sequence
<220> FEATURE:
<223> OTHER INFORMATION: Pfam00657 consensus sequence from database
      version 6.

<400> SEQUENCE: 2

Ile Val Ala Phe Gly Asp Ser Leu Thr Asp Gly Glu Ala Tyr Tyr Gly
1               5                   10                  15

Asp Ser Asp Gly Gly Gly Trp Gly Ala Gly Leu Ala Asp Arg Leu Thr
                20                  25                  30

Ala Leu Leu Arg Leu Arg Ala Arg Pro Arg Gly Val Asp Val Phe Asn
            35                  40                  45

Arg Gly Ile Ser Gly Arg Thr Ser Asp Gly Arg Leu Ile Val Asp Ala
        50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
                85                  90                  95

Ala Gly Ala Thr Ile Leu Pro Thr Ser Gly Pro Phe Leu Ile Gln Val
```

```
                    100                 105                 110
Gln Phe Lys Asp Phe Lys Ser Gln Val Leu Glu Leu Arg Gln Ala Leu
            115                 120                 125

Gly Leu Leu Gln Glu Leu Leu Arg Leu Leu Pro Val Leu Asp Ala Lys
        130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
            340                 345                 350

Gly Tyr Lys Ala Val Ala Glu Ala Leu
        355                 360

<210> SEQ ID NO 3
<211> LENGTH: 335
<212> TYPE: PRT
<213> ORGANISM: Aeromonas hydrophila

<400> SEQUENCE: 3

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
```

```
            115                 120                 125
Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
                180                 185                 190

His Val Ser Ala Tyr His Asn Gln Leu Leu Asn Leu Ala Arg Gln
            195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
                260                 265                 270

Leu Ala Ile Ala Gly Asn Pro Leu Leu Ala Gln Ala Val Ala Ser Pro
            275                 280                 285

Met Ala Arg Ser Ala Ser Thr Leu Asn Cys Glu Gly Lys Met Phe
290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 4
<211> LENGTH: 336
<212> TYPE: PRT
<213> ORGANISM: Aeromonas salmonicida

<400> SEQUENCE: 4

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
```

```
                    165                 170                 175
Gly Gln Asn Pro Ser Ala Arg Ser Gln Lys Val Val Glu Ala Val Ser
            180                 185                 190

His Val Ser Ala Tyr His Asn Lys Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
```

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
                260                 265                 270

Pro Val His Pro Asn Ala Leu Gly Glu Arg Arg Met Ala Glu His Thr
                275                 280                 285

Met Asp Val Leu Gly Leu Asp
290                 295

<210> SEQ ID NO 6
<211> LENGTH: 295
<212> TYPE: PRT
<213> ORGANISM: Streptomyces coelicolor

<400> SEQUENCE: 6

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
                20                  25                  30

Pro Ala Gln Ala Thr Pro Thr Leu Asp Tyr Val Ala Leu Gly Asp Ser
                35                  40                  45

Tyr Ser Ala Gly Ser Gly Val Leu Pro Val Asp Pro Ala Asn Leu Leu
50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
                100                 105                 110

Gly Thr Gly Thr Asp Leu Val Thr Leu Thr Ile Gly Gly Asn Asp Asn
                115                 120                 125

Ser Thr Phe Ile Asn Ala Ile Thr Ala Cys Gly Thr Ala Gly Val Leu
130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
                180                 185                 190

Tyr Pro Trp Ile Thr Pro Ala Thr Ala Asp Pro Ser Cys Phe Leu Lys
                195                 200                 205

Leu Pro Leu Ala Ala Gly Asp Val Pro Tyr Leu Arg Ala Ile Gln Ala
210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
                260                 265                 270

Pro Val His Pro Asn Ala Leu Gly Glu Arg Arg Met Ala Glu His Thr
                275                 280                 285

Met Asp Val Leu Gly Leu Asp

```
                                                                   290                 295

<210> SEQ ID NO 7
<211> LENGTH: 238
<212> TYPE: PRT
<213> ORGANISM: Saccharomyces cerevisiae

<400> SEQUENCE: 7

Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Gly Pro Gly Leu Val Asp Arg Glu Lys
        115                 120                 125

Trp Glu Lys Glu Lys Ser Glu Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235

<210> SEQ ID NO 8
<211> LENGTH: 347
<212> TYPE: PRT
<213> ORGANISM: Ralstonia sp.

<400> SEQUENCE: 8

Met Asn Leu Arg Gln Trp Met Gly Ala Ala Thr Ala Ala Leu Ala Leu
1               5                   10                  15

Gly Leu Ala Ala Cys Gly Gly Gly Thr Asp Gln Ser Gly Asn Pro
            20                  25                  30

Asn Val Ala Lys Val Gln Arg Met Val Val Phe Gly Asp Ser Leu Ser
        35                  40                  45

Asp Ile Gly Thr Tyr Thr Pro Val Ala Gln Ala Val Gly Gly Gly Lys
    50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95
```

```
Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Ala Gly Ala
    115                 120                 125

Leu Thr Tyr Pro Val Gln Gln Leu Ala Asn Phe Tyr Ala Ala Ser
130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Thr Ser Gly Ser
                165                 170                 175

Gly Val Thr Pro Ala Ile Ala Thr Ala Gln Val Gln Gln Ala Ala Thr
                180                 185                 190

Asp Leu Val Gly Tyr Val Lys Asp Met Ile Ala Lys Gly Ala Thr Gln
                195                 200                 205

Val Tyr Val Phe Asn Leu Pro Asp Ser Ser Leu Thr Pro Asp Gly Val
210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
                260                 265                 270

Phe Gly Phe Ala Asn Thr Ser Ala Arg Ala Cys Asp Ala Thr Lys Ile
                275                 280                 285

Asn Ala Leu Val Pro Ser Ala Gly Gly Ser Ser Leu Phe Cys Ser Ala
                290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
                340                 345

<210> SEQ ID NO 9
<211> LENGTH: 261
<212> TYPE: PRT
<213> ORGANISM: Streptomyces coelicolor

<400> SEQUENCE: 9

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
                20                  25                  30

Ala Val Leu Leu Ala Asp Arg Arg Pro Glu Gly Asp Phe Thr Tyr Thr
            35                  40                  45

Asn Leu Ala Val Arg Gly Arg Leu Leu Asp Gln Ile Val Ala Glu Gln
        50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125
```

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
                260

<210> SEQ ID NO 10
<211> LENGTH: 260
<212> TYPE: PRT
<213> ORGANISM: Streptomyces coelicolor

<400> SEQUENCE: 10

Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
        35                  40                  45

Arg Tyr Ala Asn Leu Ala Val Arg Gly Lys Leu Ile Gly Gln Ile Val
    50                  55                  60

Asp Glu Gln Val Asp Val Ala Ala Ala Met Gly Ala Asp Val Ile Thr
65                  70                  75                  80

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Arg Thr Ala Asp Val Arg Phe Ala
    210                 215                 220

Arg Gln His Leu Leu Pro Trp Ile Gly Arg Arg Leu Thr Gly Arg Ser
225                 230                 235                 240

```
Ser Gly Asp Gly Leu Pro Ala Lys Arg Pro Asp Leu Leu Pro Tyr Glu
                245                 250                 255

Asp Pro Ala Arg
            260

<210> SEQ ID NO 11
<211> LENGTH: 454
<212> TYPE: PRT
<213> ORGANISM: Streptomyces coelicolor

<400> SEQUENCE: 11

Met Thr Arg Gly Arg Asp Gly Gly Ala Gly Ala Pro Pro Thr Lys His
1               5                   10                  15

Arg Ala Leu Leu Ala Ala Ile Val Thr Leu Ile Val Ala Ile Ser Ala
                20                  25                  30

Ala Ile Tyr Ala Gly Ala Ser Ala Asp Asp Gly Ser Arg Asp His Ala
                35                  40                  45

Leu Gln Ala Gly Gly Arg Leu Pro Arg Gly Asp Ala Ala Pro Ala Ser
        50                  55                  60

Thr Gly Ala Trp Val Gly Ala Trp Ala Thr Ala Pro Ala Ala Ala Glu
65              70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
                100                 105                 110

Leu Tyr Gly Gln Ser Pro Leu Thr Val Thr His Ala Ser Ile Ala Leu
            115                 120                 125

Ala Ala Gly Pro Asp Thr Ala Ala Ile Ala Asp Thr Met Arg Arg
        130                 135                 140

Leu Thr Phe Gly Gly Ser Ala Arg Val Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
        195                 200                 205

Asp Val Thr Ala Val Ala Tyr Thr Thr Pro Thr Pro Tyr Trp Arg Tyr
    210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
                245                 250                 255

Asn His Arg Trp Thr Asp Val Leu Ala Ala Arg Leu His Glu Ala Ala
                260                 265                 270

Gly Asp Gly Arg Asp Thr Pro Arg Tyr Ser Val Val Asn Glu Gly Ile
            275                 280                 285

Ser Gly Asn Arg Leu Leu Thr Ser Arg Pro Gly Arg Pro Ala Asp Asn
        290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
                325                 330                 335

Pro Glu Leu Ala Asp Arg Asp Ala Ile Leu Thr Gly Leu Arg Thr Leu
            340                 345                 350
```

Val Asp Arg Ala His Ala Arg Gly Leu Arg Val Val Gly Ala Thr Ile
        355                 360                 365

Thr Pro Phe Gly Gly Tyr Gly Gly Tyr Thr Glu Ala Arg Glu Thr Met
    370                 375                 380

Arg Gln Glu Val Asn Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415

Met Arg Ser Asp Tyr Asp Ser Gly Asp His Leu His Pro Gly Asp Lys
            420                 425                 430

Gly Tyr Ala Arg Met Gly Ala Val Ile Asp Leu Ala Ala Leu Lys Gly
        435                 440                 445

Ala Ala Pro Val Lys Ala
    450

<210> SEQ ID NO 12
<211> LENGTH: 340
<212> TYPE: PRT
<213> ORGANISM: Streptomyces coelicolor

<400> SEQUENCE: 12

Met Thr Ser Met Ser Arg Ala Arg Val Ala Arg Arg Ile Ala Ala Gly
1               5                   10                  15

Ala Ala Tyr Gly Gly Gly Gly Ile Gly Leu Ala Gly Ala Ala Ala Val
            20                  25                  30

Gly Leu Val Val Ala Glu Val Gln Leu Ala Arg Arg Val Gly Val
        35                  40                  45

Gly Thr Pro Thr Arg Val Pro Asn Ala Gln Gly Leu Tyr Gly Gly Thr
    50                  55                  60

Leu Pro Thr Ala Gly Asp Pro Pro Leu Arg Leu Met Met Leu Gly Asp
65                  70                  75                  80

Ser Thr Ala Ala Gly Gln Gly Val His Arg Ala Gly Gln Thr Pro Gly
                85                  90                  95

Ala Leu Leu Ala Ser Gly Leu Ala Ala Val Ala Glu Arg Pro Val Arg
            100                 105                 110

Leu Gly Ser Val Ala Gln Pro Gly Ala Cys Ser Asp Asp Leu Asp Arg
        115                 120                 125

Gln Val Ala Leu Val Leu Ala Glu Pro Asp Arg Val Pro Asp Ile Cys
    130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Arg Leu Arg Thr Ala
                165                 170                 175

Gly Ala Glu Val Val Val Gly Thr Cys Pro Asp Leu Gly Thr Ile Glu
            180                 185                 190

Arg Val Arg Gln Pro Leu Arg Trp Leu Ala Arg Arg Ala Ser Arg Gln
        195                 200                 205

Leu Ala Ala Ala Gln Thr Ile Gly Ala Val Glu Gln Gly Gly Arg Thr
    210                 215                 220

Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala
                245                 250                 255

Thr Ala Ala Met Ala Val Leu Pro Ser Val Cys Ala Ala Leu Gly Leu
            260                 265                 270

```
Trp Pro Ala Asp Glu Glu His Pro Asp Ala Leu Arg Arg Glu Gly Phe
            275                 280                 285

Leu Pro Val Ala Arg Ala Ala Glu Ala Ala Ser Glu Ala Gly Thr
        290                 295                 300

Glu Val Ala Ala Ala Met Pro Thr Gly Pro Gly Pro Trp Ala Leu
305                 310                 315                 320

Leu Lys Arg Arg Arg Arg Arg Val Ser Glu Ala Glu Pro Ser Ser
        325                 330                 335

Pro Ser Gly Val
        340

<210> SEQ ID NO 13
<211> LENGTH: 305
<212> TYPE: PRT
<213> ORGANISM: Streptomyces coelicolor

<400> SEQUENCE: 13

Met Gly Arg Gly Thr Asp Gln Arg Thr Arg Tyr Gly Arg Arg Ala
1               5                   10                  15

Arg Val Ala Leu Ala Ala Leu Thr Ala Ala Val Leu Gly Val Gly Val
            20                  25                  30

Ala Gly Cys Asp Ser Val Gly Gly Asp Ser Pro Ala Pro Ser Gly Ser
        35                  40                  45

Pro Ser Lys Arg Thr Arg Thr Ala Pro Ala Trp Asp Thr Ser Pro Ala
    50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
                85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
    130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270

Thr Asp Gln Leu Ser His Trp Asp Trp Phe His Pro Ser Val Asp Gly
        275                 280                 285

Gln Ala Arg Leu Ala Glu Ile Ala Tyr Arg Ala Val Thr Ala Lys Asn
    290                 295                 300
```

Pro
305

<210> SEQ ID NO 14
<211> LENGTH: 268
<212> TYPE: PRT
<213> ORGANISM: Streptomyces rimosus

<400> SEQUENCE: 14

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
        35                  40                  45

Val Gly Ala Gly Ser Tyr Asp Ser Ser Gly Ser Cys Lys Arg Ser
    50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Leu Gly Tyr Pro
                165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Asp Asp Ile Asn Ala Val Thr
        195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
            260                 265

<210> SEQ ID NO 15
<211> LENGTH: 336
<212> TYPE: PRT
<213> ORGANISM: Aeromonas salmonicida subsp.Salmonicida

<400> SEQUENCE: 15

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
 50                  55                  60

Val Trp Leu Glu Gln Leu Thr Lys Gln Phe Pro Gly Leu Thr Ile Ala
 65                  70                  75                  80

Asn Glu Ala Glu Gly Gly Ala Thr Ala Val Ala Tyr Asn Lys Ile Ser
                     85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
        130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
                180                 185                 190

His Val Ser Ala Tyr His Asn Lys Leu Leu Asn Leu Ala Arg Gln
            195                 200                 205

Leu Ala Pro Thr Gly Met Val Lys Leu Phe Glu Ile Asp Lys Gln Phe
        210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
        290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 16
<211> LENGTH: 318
<212> TYPE: PRT
<213> ORGANISM: Aeromonas salmonicida

<400> SEQUENCE: 16

Ala Asp Thr Arg Pro Ala Phe Ser Arg Ile Val Met Phe Gly Asp Ser
 1               5                  10                  15

Leu Ser Asp Thr Gly Lys Met Tyr Ser Lys Met Arg Gly Tyr Leu Pro
                20                  25                  30

Ser Ser Pro Pro Tyr Tyr Glu Gly Arg Phe Ser Asn Gly Pro Val Trp
            35                  40                  45

Leu Glu Gln Leu Thr Lys Gln Phe Pro Gly Leu Thr Ile Ala Asn Glu
 50                  55                  60

Ala Glu Gly Gly Ala Thr Ala Val Ala Tyr Asn Lys Ile Ser Trp Asp
 65                  70                  75                  80

Pro Lys Tyr Gln Val Ile Asn Asn Leu Asp Tyr Glu Val Thr Gln Phe
                85                  90                  95

```
Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                     135                 140

Asn Gly Ala Lys Gln Ile Leu Leu Phe Asn Leu Pro Asp Leu Gly Gln
145                     150                 155                 160

Asn Pro Ser Ala Arg Ser Gln Lys Val Val Glu Ala Val Ser His Val
                    165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
210                     215                 220

Cys Tyr Asp Gly Gly Tyr Val Trp Lys Pro Phe Ala Thr Arg Ser Val
225                     230                 235                 240

Ser Thr Asp Arg Gln Leu Ser Ala Phe Ser Pro Gln Glu Arg Leu Ala
                    245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
            275                 280                 285

Gln Val His Pro Thr Thr Val Val His Ala Ala Leu Ser Glu Arg Ala
            290                 295                 300

Ala Thr Phe Ile Glu Thr Gln Tyr Glu Phe Leu Ala His Gly
305                     310                 315

<210> SEQ ID NO 17
<211> LENGTH: 465
<212> TYPE: PRT
<213> ORGANISM: Candida parapsilosis

<400> SEQUENCE: 17

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Ser Phe Thr Val
145                 150                 155                 160
```

```
Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe
465

<210> SEQ ID NO 18
<211> LENGTH: 471
<212> TYPE: PRT
<213> ORGANISM: Candida parapsilosis

<400> SEQUENCE: 18

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60
```

-continued

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
            85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
            115                 120                 125

Thr Gln Gly Glu Met Tyr Tyr Ile Ser Ala Leu Leu Asp Gln Gly Tyr
        130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
            275                 280                 285

Gly Gly Ile Ala Tyr Phe Gly Lys Ser Phe Phe Ser Arg Ile Ile Arg
        290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
        370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
450                 455                 460

Phe His His His His His
465                 470

<210> SEQ ID NO 19

```
<211> LENGTH: 261
<212> TYPE: PRT
<213> ORGANISM: Streptomyces coelicolor

<400> SEQUENCE: 19

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
```

<400> SEQUENCE: 23

000

<210> SEQ ID NO 24

<400> SEQUENCE: 24

000

<210> SEQ ID NO 25
<211> LENGTH: 347
<212> TYPE: PRT
<213> ORGANISM: Aeromonas hydrophila

<400> SEQUENCE: 25

```
Met Phe Lys Phe Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
                20                  25                  30

Ser Arg Pro Ala Phe Ser Arg Ile Val Met Phe Gly Asp Ser Leu Ser
            35                  40                  45

Asp Thr Gly Lys Met Tyr Ser Lys Met Arg Gly Tyr Leu Pro Ser Ser
        50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
        115                 120                 125

Lys Asp Ser Phe Lys Pro Asp Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255

Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
    290                 295                 300

Ser Ala Ser Pro Leu Asn Cys Glu Gly Lys Met Phe Trp Asp Gln Val
305                 310                 315                 320
```

```
His Pro Thr Thr Val Val His Ala Ala Leu Ser Glu Arg Ala Ala Thr
                325                 330                 335
Phe Ile Ala Asn Gln Tyr Glu Phe Leu Ala His
        340                 345
```

<210> SEQ ID NO 26
<211> LENGTH: 267
<212> TYPE: PRT
<213> ORGANISM: Streptomyces sp.

<400> SEQUENCE: 26

```
Met Arg Leu Thr Arg Ser Leu Ser Ala Ala Ser Val Ile Val Phe Ala
 1               5                  10                  15
Leu Leu Leu Ala Leu Leu Gly Ile Ser Pro Ala Gln Ala Ala Gly Pro
                20                  25                  30
Ala Tyr Val Ala Leu Gly Asp Ser Tyr Ser Ser Gly Asn Gly Ala Gly
                35                  40                  45
Ser Tyr Ile Asp Ser Ser Gly Asp Cys His Arg Ser Asn Asn Ala Tyr
    50                  55                  60
Pro Ala Arg Trp Ala Ala Ala Asn Ala Pro Ser Ser Phe Thr Phe Ala
65                  70                  75                  80
Ala Cys Ser Gly Ala Val Thr Thr Asp Val Ile Asn Asn Gln Leu Gly
                85                  90                  95
Ala Leu Asn Ala Ser Thr Gly Leu Val Ser Ile Thr Ile Gly Gly Asn
                100                 105                 110
Asp Ala Gly Phe Ala Asp Ala Met Thr Thr Cys Val Thr Ser Ser Asp
            115                 120                 125
Ser Thr Cys Leu Asn Arg Leu Ala Thr Ala Thr Asn Tyr Ile Asn Thr
    130                 135                 140
Thr Leu Leu Ala Arg Leu Asp Ala Val Tyr Ser Gln Ile Lys Ala Arg
145                 150                 155                 160
Ala Pro Asn Ala Arg Val Val Val Leu Gly Tyr Pro Arg Met Tyr Leu
                165                 170                 175
Ala Ser Asn Pro Trp Tyr Cys Leu Gly Leu Ser Asn Thr Lys Arg Ala
                180                 185                 190
Ala Ile Asn Thr Thr Ala Asp Thr Leu Asn Ser Val Ile Ser Ser Arg
            195                 200                 205
Ala Thr Ala His Gly Phe Arg Phe Gly Asp Val Arg Pro Thr Phe Asn
    210                 215                 220
Asn His Glu Leu Phe Phe Gly Asn Asp Trp Leu His Ser Leu Thr Leu
225                 230                 235                 240
Pro Val Trp Glu Ser Tyr His Pro Thr Ser Thr Gly His Gln Ser Gly
                245                 250                 255
Tyr Leu Pro Val Leu Asn Ala Asn Ser Ser Thr
                260                 265
```

<210> SEQ ID NO 27
<211> LENGTH: 548
<212> TYPE: PRT
<213> ORGANISM: Thermobifida sp

<400> SEQUENCE: 27

```
Met Leu Pro His Pro Ala Gly Glu Arg Gly Glu Val Gly Ala Phe Phe
 1               5                  10                  15
Ala Leu Leu Val Gly Thr Pro Gln Asp Arg Arg Leu Arg Leu Glu Cys
                20                  25                  30
His Glu Thr Arg Pro Leu Arg Gly Arg Cys Gly Cys Gly Glu Arg Arg
```

-continued

```
                35                  40                  45
Val Pro Pro Leu Thr Leu Pro Gly Asp Gly Val Leu Cys Thr Thr Ser
 50                  55                  60

Ser Thr Arg Asp Ala Glu Thr Val Trp Arg Lys His Leu Gln Pro Arg
 65                  70                  75                  80

Pro Asp Gly Gly Phe Arg Pro His Leu Gly Val Gly Cys Leu Leu Ala
                 85                  90                  95

Gly Gln Gly Ser Pro Gly Val Leu Trp Cys Gly Arg Glu Gly Cys Arg
                100                 105                 110

Phe Glu Val Cys Arg Arg Asp Thr Pro Gly Leu Ser Arg Thr Arg Asn
                115                 120                 125

Gly Asp Ser Ser Pro Pro Phe Arg Ala Gly Trp Ser Leu Pro Pro Lys
130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Leu Phe Leu Gly
                180                 185                 190

Ile Pro Ala Leu Val Leu Val Thr Ala Leu Thr Leu Val Leu Ala Val
                195                 200                 205

Pro Thr Gly Arg Glu Thr Leu Trp Arg Met Trp Cys Glu Ala Thr Gln
                210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
                260                 265                 270

Asp Tyr Tyr Pro Gly Thr Ala Val Lys Gly Gly Cys Trp Arg Ser Ala
                275                 280                 285

Asn Ala Tyr Pro Glu Leu Val Ala Glu Ala Tyr Asp Phe Ala Gly His
                290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
                340                 345                 350

Val Leu Lys Thr Cys Met Val Arg Val Pro Leu Leu Asp Ser Lys Ala
                355                 360                 365

Cys Thr Asp Gln Glu Asp Ala Ile Arg Lys Arg Met Ala Lys Phe Glu
370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
                420                 425                 430

Glu Thr Ile Gln Glu Phe Asn Gln Gln Leu Ala Glu Ala Val Ala Val
                435                 440                 445

His Asp Glu Glu Ile Ala Ala Ser Gly Gly Val Gly Ser Val Glu Phe
                450                 455                 460
```

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
            485                 490                 495

Val Asp Arg Ser Thr Phe His Pro Asn Ala Ala Gly His Arg Ala Val
        500                 505                 510

Gly Glu Arg Val Ile Glu Gln Ile Glu Thr Gly Pro Gly Arg Pro Leu
    515                 520                 525

Tyr Ala Thr Phe Ala Val Val Ala Gly Ala Thr Val Asp Thr Leu Ala
        530                 535                 540

Gly Glu Val Gly
545

<210> SEQ ID NO 28
<211> LENGTH: 372
<212> TYPE: PRT
<213> ORGANISM: Thermobifida sp.

<400> SEQUENCE: 28

Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
    115                 120                 125

Leu Ser Phe Leu Ala Cys Ser Gly Gln Arg Gly Tyr Ala Met Leu Asp
130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
    195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
    275                 280                 285

```
Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                    325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
            355                 360                 365

Gly Glu Val Gly
    370

<210> SEQ ID NO 29
<211> LENGTH: 300
<212> TYPE: PRT
<213> ORGANISM: Corynebacterium efficiens

<400> SEQUENCE: 29

Met Arg Thr Thr Val Ile Ala Ala Ser Ala Leu Leu Leu Ala Gly
1               5                  10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
        50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
        275                 280                 285
```

```
Val Arg Asp Ala Leu Gly Leu Glu Pro Val Gln Pro
    290             295             300
```

<210> SEQ ID NO 30
<211> LENGTH: 284
<212> TYPE: PRT
<213> ORGANISM: Novosphingobium aromaticivorans

<400> SEQUENCE: 30

```
Met Gly Gln Val Lys Leu Phe Ala Arg Arg Cys Ala Pro Val Leu Leu
1               5                   10                  15

Ala Leu Ala Gly Leu Ala Pro Ala Ala Thr Val Ala Arg Glu Ala Pro
            20                  25                  30

Leu Ala Glu Gly Ala Arg Tyr Val Ala Leu Gly Ser Ser Phe Ala Ala
        35                  40                  45

Gly Pro Gly Val Gly Pro Asn Ala Pro Gly Ser Pro Glu Arg Cys Gly
    50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
            100                 105                 110

Thr Arg Leu Val Thr Leu Thr Ile Gly Gly Asn Asp Val Ser Phe Val
        115                 120                 125

Gly Asn Ile Phe Ala Ala Ala Cys Glu Lys Met Ala Ser Pro Asp Pro
    130                 135                 140

Arg Cys Gly Lys Trp Arg Glu Ile Thr Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Asp Tyr Ile Thr Val Leu Pro Pro Ser
            180                 185                 190

Gly Thr Cys Ala Ala Met Ala Ile Ser Pro Asp Arg Leu Ala Gln Ser
        195                 200                 205

Arg Ser Ala Ala Lys Arg Leu Ala Arg Ile Thr Ala Arg Val Ala Arg
    210                 215                 220

Glu Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
            260                 265                 270

Ala Ala Ala Leu Val Lys Leu Val Lys Leu Met Lys
        275                 280
```

<210> SEQ ID NO 31
<211> LENGTH: 268
<212> TYPE: PRT
<213> ORGANISM: Streptomyces coelicolor

<400> SEQUENCE: 31

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Gln Pro
            20                  25                  30

Ala Ala Ala Asp Gly Tyr Val Ala Leu Gly Asp Ser Tyr Ser Ser Gly
```

```
                35                  40                  45
Val Gly Ala Gly Ser Tyr Ile Ser Ser Ser Gly Asp Cys Lys Arg Ser
 50                  55                  60

Thr Lys Ala His Pro Tyr Leu Trp Ala Ala His Ser Pro Ser Thr
 65                  70                  75                  80

Phe Asp Phe Thr Ala Cys Ser Gly Ala Arg Thr Gly Asp Val Leu Ser
                 85                  90                  95

Gly Gln Leu Gly Pro Leu Ser Ser Gly Thr Gly Leu Val Ser Ile Ser
                100                 105                 110

Ile Gly Gly Asn Asp Ala Gly Phe Ala Asp Thr Met Thr Thr Cys Val
                115                 120                 125

Leu Gln Ser Glu Ser Ser Cys Leu Ser Arg Ile Ala Thr Ala Glu Ala
130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
                180                 185                 190

Arg Thr Ala Ile Asn Lys Ala Ser Asp His Leu Asn Thr Val Leu Ala
                195                 200                 205

Gln Arg Ala Ala Ala His Gly Phe Thr Phe Gly Asp Val Arg Thr Thr
                210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
                260                 265

<210> SEQ ID NO 32
<211> LENGTH: 269
<212> TYPE: PRT
<213> ORGANISM: Streptomyces avermitilis

<400> SEQUENCE: 32

Met Arg Arg Ser Arg Ile Thr Ala Tyr Val Thr Ser Leu Leu Leu Ala
 1               5                  10                  15

Val Gly Cys Ala Leu Thr Gly Ala Ala Thr Ala Gln Ala Ser Pro Ala
                20                  25                  30

Ala Ala Thr Gly Tyr Val Ala Leu Gly Asp Ser Tyr Ser Ser Gly
                35                  40                  45

Val Gly Ala Gly Ser Tyr Leu Ser Ser Ser Gly Asp Cys Lys Arg Ser
 50                  55                  60

Ser Lys Ala Tyr Pro Tyr Leu Trp Gln Ala Ala His Ser Pro Ser Ser
 65                  70                  75                  80

Phe Ser Phe Met Ala Cys Ser Gly Ala Arg Thr Gly Asp Val Leu Ala
                 85                  90                  95

Asn Gln Leu Gly Thr Leu Asn Ser Ser Thr Gly Leu Val Ser Leu Thr
                100                 105                 110

Ile Gly Gly Asn Asp Ala Gly Phe Ser Asp Val Met Thr Thr Cys Val
                115                 120                 125

Leu Gln Ser Asp Ser Ala Cys Leu Ser Arg Ile Asn Thr Ala Lys Ala
130                 135                 140

Tyr Val Asp Ser Thr Leu Pro Gly Gln Leu Asp Ser Val Tyr Thr Ala
```

```
            145                 150                 155                 160
Ile Ser Thr Lys Ala Pro Ser Ala His Val Ala Val Leu Gly Tyr Pro
                    165                 170                 175

Arg Phe Tyr Lys Leu Gly Gly Ser Cys Leu Ala Gly Leu Ser Glu Thr
                180                 185                 190

Lys Arg Ser Ala Ile Asn Asp Ala Ala Asp Tyr Leu Asn Ser Ala Ile
                195                 200                 205

Ala Lys Arg Ala Ala Asp His Gly Phe Thr Phe Gly Asp Val Lys Ser
            210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                    245                 250                 255

Gln Ser Gly Gly Tyr Leu Pro Val Met Asn Ser Val Ala
                260                 265

<210> SEQ ID NO 33
<211> LENGTH: 267
<212> TYPE: PRT
<213> ORGANISM: Streptomyces sp.

<400> SEQUENCE: 33

Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
                20                  25                  30

Ala Tyr Val Ala Leu Gly Asp Ser Tyr Ser Ser Gly Asn Gly Ala Gly
                35                  40                  45

Ser Tyr Ile Asp Ser Ser Gly Asp Cys His Arg Ser Asn Asn Ala Tyr
            50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
                100                 105                 110

Asp Ala Gly Phe Ala Asp Ala Met Thr Thr Cys Val Thr Ser Ser Asp
                115                 120                 125

Ser Thr Cys Leu Asn Arg Leu Ala Thr Ala Thr Asn Tyr Ile Asn Thr
            130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                    165                 170                 175

Ala Ser Asn Pro Trp Tyr Cys Leu Gly Leu Ser Asn Thr Lys Arg Ala
                180                 185                 190

Ala Ile Asn Thr Thr Ala Asp Thr Leu Asn Ser Val Ile Ser Ser Arg
                195                 200                 205

Ala Thr Ala His Gly Phe Arg Phe Gly Asp Val Arg Pro Thr Phe Asn
            210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                    245                 250                 255

Tyr Leu Pro Val Leu Asn Ala Asn Ser Ser Thr
```

<210> SEQ ID NO 34
<211> LENGTH: 317
<212> TYPE: PRT
<213> ORGANISM: Aeromonas hydrophila

<400> SEQUENCE: 34

```
Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Gln Arg Asn Ala
    210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
        275                 280                 285

Gln Val His Pro Thr Thr Val Val His Ala Ala Leu Ser Glu Pro Ala
    290                 295                 300

Ala Thr Phe Ile Glu Ser Gln Tyr Glu Phe Leu Ala His
305                 310                 315
```

<210> SEQ ID NO 35
<211> LENGTH: 318
<212> TYPE: PRT
<213> ORGANISM: Aeromonas salmonicida

<400> SEQUENCE: 35

```
Ala Asp Thr Arg Pro Ala Phe Ser Arg Ile Val Met Phe Gly Asp Ser
1               5                   10                  15
```

Leu Ser Asp Thr Gly Lys Met Tyr Ser Lys Met Arg Gly Tyr Leu Pro
        20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
 50                  55                  60

Ala Glu Gly Gly Ala Thr Ala Val Ala Tyr Asn Lys Ile Ser Trp Asn
 65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
            130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
        210                 215                 220

Cys Tyr Asp Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
        290                 295                 300

Ala Thr Phe Ile Glu Thr Gln Tyr Glu Phe Leu Ala His Gly
305                 310                 315

<210> SEQ ID NO 36
<211> LENGTH: 1371
<212> TYPE: DNA
<213> ORGANISM: Streptomyces thermosacchari

<400> SEQUENCE: 36
acaggccgat gcacggaacc gtaccttccc gcagtgaagc gctctccccc catcgttcgc        60
cgggacttca tccgcgattt tggcatgaac acttccttca acgcgcgtag cttgctacaa       120
gtgcggcagc agaccccgct cgttggaggct cagtgagatt gacccgatcc ctgtcggccg      180
catccgtcat cgtcttcgcc ctgctgctcg cgctgctggg catcagcccg gcccaggcag       240
ccggcccggc ctatgtggcc ctgggggatt cctattcctc gggcaacggc gccggaagtt       300
acatcgattc gagcggtgac tgtcaccgca gcaacaacgc gtaccccgcc cgctgggcgg       360
cggccaacgc accgtcctcc ttcaccttcg cggcctgctc gggagcggtg accacggatg       420

-continued

```
tgatcaacaa tcagctgggc gccctcaacg cgtccaccgg cctggtgagc atcaccatcg    480
gcggcaatga cgcgggcttc gcggacgcga tgaccacctg cgtcaccagc tcggacagca    540
cctgcctcaa ccggctggcc accgccacca actacatcaa caccaccctg ctcgcccggc    600
tcgacgcggt ctacagccag atcaaggccc gtgcccccaa cgcccgcgtg gtcgtcctcg    660
gctacccgcg catgtacctg gcctcgaacc cctggtactg cctgggcctg agcaacacca    720
agcgcgcggc catcaacacc accgccgaca ccctcaactc ggtgatctcc tcccgggcca    780
ccgcccacgg attccgattc ggcgatgtcc gcccgacctt caacaaccac gaactgttct    840
tcggcaacga ctggctgcac tcactcaccc tgccggtgtg ggagtcgtac cacccccacca    900 gcacgggcca tcagagcggc tatctgccgg tcctcaacgc caacagctcg acctgatcaa    960
cgcacggccg tgcccgcccc gcgcgtcacg ctcggcgcgg gcgccgcagc gcgttgatca   1020
gcccacagtg ccggtgacgg tcccaccgtc acggtcgagg gtgtacgtca cggtggcgcc   1080
gctccagaag tggaacgtca gcaggaccgt ggagccgtcc ctgacctcgt cgaagaactc   1140
cggggtcagc gtgatcaccc ctcccccgta gccgggggcg aaggcggcgc cgaactcctt   1200
gtaggacgtc cagtcgtgcg gcccggcgtt gccaccgtcc gcgtagaccg cttccatggt   1260
cgccagccgg tccccgcgga actcggtggg gatgtccgtg cccaaggtgg tcccggtggt   1320
gtccgagagc accgggggct cgtaccggat gatgtgcaga tccaaagaat t            1371
```

<210> SEQ ID NO 37
<211> LENGTH: 267
<212> TYPE: PRT
<213> ORGANISM: Streptomyces thermosacchari

<400> SEQUENCE: 37

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
```

-continued

```
              210                 215                 220
Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
                260                 265

<210> SEQ ID NO 38
<211> LENGTH: 548
<212> TYPE: PRT
<213> ORGANISM: Thermobifida fusca

<400> SEQUENCE: 38

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
                20                  25                  30

His Glu Thr Arg Pro Leu Arg Gly Arg Cys Gly Cys Gly Glu Arg Arg
            35                  40                  45

Val Pro Pro Leu Thr Leu Pro Gly Asp Gly Val Leu Cys Thr Thr Ser
50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
    290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
```

```
                 325                 330                 335
Ser Leu Val Thr Ile Gly Ile Gly Gly Asn Asp Leu Gly Phe Ser Thr
            340                 345                 350

Val Leu Lys Thr Cys Met Val Arg Val Pro Leu Leu Asp Ser Lys Ala
            355                 360                 365

Cys Thr Asp Gln Glu Asp Ala Ile Arg Lys Arg Met Ala Lys Phe Glu
            370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
            420                 425                 430

Glu Thr Ile Gln Glu Phe Asn Gln Gln Leu Ala Glu Ala Val Ala Val
            435                 440                 445

His Asp Glu Glu Ile Ala Ala Ser Gly Gly Val Gly Ser Val Glu Phe
            450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
            515                 520                 525

Tyr Ala Thr Phe Ala Val Val Ala Gly Ala Thr Val Asp Thr Leu Ala
            530                 535                 540

Gly Glu Val Gly
545

<210> SEQ ID NO 39
<211> LENGTH: 3000
<212> TYPE: DNA
<213> ORGANISM: Thermobifida fusca

<400> SEQUENCE: 39
ggtggtgaac cagaacaccc ggtcgtcggc gtgggcgtcc aggtgcaggt gcaggttctt      60
caactgctcc agcaggatgc cgccgtggcc gtgcacgatg ccttgggca ggcctgtggt     120 ccccgacgag tacagcaccc atagcggatg gtcgaacggc agcggggtga actccagttc     180
cgcgccttcg cccgcggctt cgaactccgc ccaggacagg gtgtcggcga cagggccgca     240
gcccaggtac ggcaggacga cggtgtgctg caggctgggc atgccgtcgc gcagggcttt     300
gagcacgtca cggcggtcga agtccttacc gccgtagcgg tagccgtcca cggccagcag     360
cactttcggt tcgatctgcg cgaaccggtc gaggacgctg cgcacccga gtcgggggga     420 acaggacgac caggtcgcac cgatcgcggc gcaggcgagg aatgcggccg tcgcctcggc     480
gatgttcggc aggtaggcca cgacccgtc gccgggccc accccgaggc tgcggagggc     540
cgcagcgatc gcggcggtgc gggtccgcag ttctccccag gtccactcgg tcaacggccg     600
gagttcggac gcgtgccgga tcgccacggc tgatgggtca cggtcgcgga agatgtgctc     660
ggcgtagttg agggtggcgc cggggaacca gacggcgccg ggcatggcgt cggaggcgag     720
cactgtggtg tacggggtgg cggcgcgcac ccggtagtac tcccagatcg cggaccagaa     780
tccttcgagg tcggttaccg accagcgcca cagtgcctcg tagtccggtg cgtccacacc     840
```

| | |
|---|---:|
| gcggtgctcc cgcacccagc gggtgaacgc ggtgaggttg gcgcgttctt tgcgctcctc | 900 |
| gtcgggactc cacaggatcg gcggctgcgg cttgagtgtc atgaaacgcg accccttcgt | 960 |
| ggacggtgcg gatgcggtga gcgtcgggtg cctcccctaa cgctccccgg tgacggagtg | 1020 |
| ttgtgcacca catctagcac gcgggacgcg gaaaccgtat ggagaaaaca cctacaaccc | 1080 |
| cggccggacg gtgggtttcg gccacactta ggggtcgggt gcctgcttgc cgggcagggc | 1140 |
| agtcccgggg tgctgtggtg cgggcgggag ggctgtcgct tcgaggtgtg ccggcggac | 1200 |
| actccgggcc tcagccgtac ccgcaacggg gacagttctc ctcccttccg ggctggatgg | 1260 |
| tcccttcccc cgaaatgcgg cgagatctcc cagtcagccc ggaaaacacc cgctgtgccc | 1320 |
| aggtactctt tgcttcgaac agacaggccg gacggtccac gggggaggtt tgtgggcagc | 1380 |
| ggaccacgtg cggcgaccag acgacggttg ttcctcggta tccccgctct tgtacttgtg | 1440 |
| acagcgctca cgctggtctt ggctgtcccg acggggcgcg agacgctgtg gcgcatgtgg | 1500 |
| tgtgaggcca cccaggactg gtgcctgggg gtgccggtcg actcccgcgg acagcctgcg | 1560 |
| gaggacggcg agtttctgct gctttctccg gtccaggcag cgacctgggg gaactattac | 1620 |
| gcgctcgggg attcgtactc ttcgggggac ggggcccgcg actactatcc cggcaccgcg | 1680 |
| gtgaagggcg gttgctggcg gtccgctaac gcctatccgg agctggtcgc cgaagcctac | 1740 |
| gacttcgccg gacacttgtc gttcctggcc tgcagcggcc agcgcggcta cgccatgctt | 1800 |
| gacgctatcg acgaggtcgg ctcgcagctg gactggaact cccctcacac gtcgctggtg | 1860 |
| acgatcggga tcggcggcaa cgatctgggg ttctccacgg ttttgaagac ctgcatggtg | 1920 |
| cgggtgccgc tgctggacag caaggcgtgc acggaccagg aggacgctat ccgcaagcgg | 1980 |
| atggcgaaat tcgagacgac gtttgaagag ctcatcagcg aagtgcgcac ccgcgcgccg | 2040 |
| gacgcccgga tccttgtcgt gggctacccc cggattttc cggaggaacc gaccggcgcc | 2100 |
| tactacacgc tgaccgcgag caaccagcgg tggctcaacg aaaccattca ggagttcaac | 2160 |
| cagcagctcg ccgaggctgt cgcggtccac gacgaggaga ttgccgcgtc gggcggggtg | 2220 |
| ggcagcgtgg agttcgtgga cgtctaccac gcgttggacg gccacgagat cggctcggac | 2280 |
| gagccgtggg tgaacggggt gcagttgcgg gacctcgcca ccggggtgac tgtggaccgc | 2340 |
| agtaccttcc accccaacgc cgctgggcac cgggcggtcg gtgagcgggt catcgagcag | 2400 |
| atcgaaaccg gccgggccg tccgctctat gccactttcg cggtggtggc gggggcgacc | 2460 |
| gtggacactc tcgcgggcga ggtggggtga cccggcttac cgtccggccc gcaggtctgc | 2520 |
| gagcactgcg gcgatctggt ccactgccca gtgcagttcc tcttcggtga tgaccagcgg | 2580 |
| cggggagagc cggatcgttg agccgtgcgt gtctttgacg agcacacccc gctgcaggag | 2640 |
| ccgttcgcac agttctcttc cggtggccag agtcgggtcg acgtcgatcc cagcccacag | 2700 |
| gccgatgctg cgggccgcga ccacgccgtt gccgaccagt tggtcgaggc gggcgcgcag | 2760 |
| cacggggcag agggcgcgga catggtccag gtaaggcccg tcgcggacga ggctcaccac | 2820 |
| ggcagtgccg accgcgcagg cgagggcgtt gccgccgaag gtgctgccgt gctggccggg | 2880 |
| gcggatcacg tcgaagactt ccgcgtcgcc taccgccgcc gccacgggca ggatgccgcc | 2940 |
| gcccagcgct tgccgaaaca ggtagatatc ggcgtcgact ccgctgtggt cgcaggcccg | 3000 |

<210> SEQ ID NO 40
<211> LENGTH: 372
<212> TYPE: PRT
<213> ORGANISM: Thermobifida fusca

<400> SEQUENCE: 40

```
Val Gly Ser Gly Pro Arg Ala Ala Thr Arg Arg Leu Phe Leu Gly
  1               5                  10                  15

Ile Pro Ala Leu Val Leu Val Thr Ala Leu Thr Leu Val Leu Ala Val
             20                  25                  30

Pro Thr Gly Arg Glu Thr Leu Trp Arg Met Trp Cys Glu Ala Thr Gln
         35                  40                  45

Asp Trp Cys Leu Gly Val Pro Val Asp Ser Arg Gly Gln Pro Ala Glu
     50                  55                  60

Asp Gly Glu Phe Leu Leu Leu Ser Pro Val Gln Ala Ala Thr Trp Gly
 65                  70                  75                  80

Asn Tyr Tyr Ala Leu Gly Asp Ser Tyr Ser Gly Gly Ala Arg
                 85                  90                  95

Asp Tyr Tyr Pro Gly Thr Ala Val Lys Gly Gly Cys Trp Arg Ser Ala
             100                 105                 110

Asn Ala Tyr Pro Glu Leu Val Ala Glu Ala Tyr Asp Phe Ala Gly His
             115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
                180                 185                 190

Cys Thr Asp Gln Glu Asp Ala Ile Arg Lys Arg Met Ala Lys Phe Glu
                195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
                275                 280                 285

Val Asp Val Tyr His Ala Leu Asp Gly His Glu Ile Gly Ser Asp Glu
                290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
                355                 360                 365

Gly Glu Val Gly
        370

<210> SEQ ID NO 41
<211> LENGTH: 300
<212> TYPE: PRT
<213> ORGANISM: Corynebacterium efficiens

<400> SEQUENCE: 41
```

-continued

```
Met Arg Thr Thr Val Ile Ala Ala Ser Ala Leu Leu Leu Ala Gly
1               5                   10                  15

Cys Ala Asp Gly Ala Arg Glu Glu Thr Ala Gly Ala Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
                100                 105                 110

Thr Leu Pro Ala Gln Val Asp Ala Leu Thr Glu Asp Thr Thr Leu Val
            115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
                180                 185                 190

Val Val Val Thr Gly Tyr Leu Pro Leu Val Ser Ala Gly Asp Cys Pro
            195                 200                 205

Glu Leu Gly Asp Val Ser Glu Ala Asp Arg Arg Trp Ala Val Glu Leu
210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
                260                 265                 270

Tyr Pro Leu His Pro Thr Ser Ala Gly His Glu Ala Met Ala Ala Ala
            275                 280                 285

Val Arg Asp Ala Leu Gly Leu Glu Pro Val Gln Pro
290                 295                 300

<210> SEQ ID NO 42
<211> LENGTH: 3000
<212> TYPE: DNA
<213> ORGANISM: Corynebacterium efficiens

<400> SEQUENCE: 42
ttctggggtg ttatggggtt gttatcggct cgtcctgggt ggatcccgcc aggtggggta      60
ttcacggggg actttttgtgt ccaacagccg agaatgagtg ccctgagcgg tgggaatgag     120
gtgggcgggg ctgtgtcgcc atgaggggc ggcgggctct gtggtgcccc gcgaccccg       180 gccccggtga gcggtgaatg aaatccggct gtaatcagca tcccgtgccc accccgtcgg     240
ggaggtcagc gcccggagtg tctacgcagt cggatcctct cggactcggc catgctgtcg     300
gcagcatcgc gctcccgggt cttggcgtcc ctcggctgtt ctgcctgctg tccctggaag     360
gcgaaatgat caccggggag tgatacaccg gtggtctcat cccggatgcc cacttcggcg     420
ccatccggca attcgggcag ctccgggtgg aagtaggtgg catccgatgc gtcggtgacg     480
```

```
ccatagtggg cgaagatctc atcctgctcg agggtgctca ggccactctc cggatcgata    540 tcggggcgt ccttgatggc gtccttgctg aaaccgaggt gcagcttgtg ggcttccaat     600
ttcgcaccac ggagcgggac gaggctggaa tgacggccga agagcccgtg gtggacctca    660
acgaaggtgg gtagtcccgt gtcatcattg aggaacacgc cctccaccgc acccagcttg    720
tggccggagt tgtcgtaggc gctggcatcc agaagggaaa cgatctcata tttgtcggtg    780
tgctcagaca tgatcttcct tgctgtcgg tgtctggtac taccacggta gggctgaatg     840
caactgttat ttttctgtta ttttaggaat tggtccatat cccacaggct ggctgtggtc    900
aaatcgtcat caagtaatcc ctgtcacaca aaatgggtgg tgggagccct ggtcgcggtt    960
ccgtgggagg cgccgtgccc cgcaggatcg tcggcatcgg cggatctggc cggtaccccg   1020
cggtgaataa aatcattctg taaccttcat cacggttggt tttaggtatc cgccccttc    1080 gtcctgaccc cgtccccggc gcgcgggagc ccgcggttg cggtagacag gggagacgtg    1140
gacaccatga ggacaacggt catcgcagca agcgcattac tccttctcgc cggatgcgcg   1200 gatgggccc gggaggagac cgccggtgca ccgccgggtg agtcctccgg gggcatccgg    1260
gaggaggggg cggaggcgtc gacaagcatc accgacgtct acatcgccct cggggattcc   1320
tatgcggcga tgggcgggcg ggatcagccg ttacggggtg agccgttctg cctgcgctcg   1380
tccggtaatt acccggaact cctccacgca gaggtcaccg atctcacctg ccaggggcg    1440 gtgaccgggg atctgctcga acccaggacg ctggggagc gcacgctgcc ggcgcaggtg    1500
gatgcgctga cggaggacac caccctggtc accctctcca tcgggggcaa tgacctcgga   1560
ttcggggagg tggcgggatg catccgggaa cggatcgccg gggagaacgc tgatgattgc   1620
gtggacctgc tgggggaaac catcggggag cagctcgatc agcttccccc gcagctggac   1680
cgcgtgcacg aggctatccg ggaccgcgcc ggggacgcgc aggttgtggt caccggttac   1740
ctgccgctcg tgtctgccgg ggactgcccc gaactggggg atgtctccga gcggatcgt    1800 cgttgggcgg ttgagctgac cgggcagatc aacgagaccg tgcgcgaggc ggccgaacga   1860
cacgatgccc tctttgtcct gcccgacgat gccgatgagc acaccagttg tgcaccccca   1920
cagcagcgct gggcggatat ccagggccaa cagaccgatg cctatccgct gcacccgacc   1980
tccgccggcc atgaggcgat ggccgccgcc gtccgggacg cgctgggcct ggaaccggtc   2040
cagccgtagc gccgggcgcg cgcttgtcga cgaccaaccc atgccaggct gcagtcacat   2100
ccgcacatag cgcgcgcggg cgatggagta cgcaccatag aggatgagcc cgatgccgac   2160
gatgatgagc agcacactgc cgaagggttg ttccccgagg gtgcgcagag ccgagtccag   2220
acctgcggcc tgctccggat catgggccca accggcgatg acgatcaaca cccccaggat   2280
cccgaaggcg ataccacggg cgacataacc ggctgttccg gtgatgatga tcgcggtccc   2340
gacctgccct gaccccgcac ccgcctccag atcctcccgg aaatcccggg tggcccctt    2400 ccagaggttg tagacacccg ccccccagtac caccagcccg gcgaccacaa ccagcaccac   2460
accccagggt tgggataggga cggtggcggt gacatcggtg gcggtctccc catcggaggt   2520
gctgccgccc cgggcgaagg tggaggtggt caccgccagg gagaagtaga ccatggccat   2580
gaccgccccc ttggcccttt ccttgaggtc ctcgcccgcc agcagctggc tcaattgcca   2640
gagtcccagg gccgccaggg cgatgacggc aacccacagg aggaactgcc cacccggagc   2700
ctccgcgatg gtggccaggg cacctgaatt cgaggcctca tcacccgaac cgccggatcc   2760
agtggcgatg cgcaccgcga tccacccgat gaggatgtgc agtatgccca ggacaatgaa   2820
accacctctg gccagggtgg tcagcgcggg gtggtcctcg gcctggtcgg cagcccgttc   2880
```

```
gatcgtccgt tcgcggatc tggtgtcgcc cttatccata gctcccattg aaccgccttg   2940
aggggtgggc ggccactgtc agggcggatt gtgatctgaa ctgtgatgtt ccatcaaccc   3000
```

<210> SEQ ID NO 43
<211> LENGTH: 268
<212> TYPE: PRT
<213> ORGANISM: Streptomyces coelicolor

<400> SEQUENCE: 43

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
    130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265
```

<210> SEQ ID NO 44
<211> LENGTH: 2000
<212> TYPE: DNA
<213> ORGANISM: Streptomyces coelicolor

<400> SEQUENCE: 44

```
cccggcggcc cgtgcaggag cagcagccgg cccgcgatgt cctcgggcgt cgtcttcatc    60
aggccgtcca tcgcgtcggc gaccggcgcc gtgtagttgg cccggacctc gtcccaggtg   120
cccgcggcga tctggcgggt ggtgcggtgc gggccgcgcc gagggagac gtaccagaag   180 cccatcgtca cgttctccgg ctgcggttcg ggctcgtccg ccgctccgtc cgtcgcctcg   240
```

```
ccgagcacct tctcggcgag gtcggcgctg gtcgccgtca ccgtgacgtc ggcgccccgg    300
ctccagcgcg agatcagcag cgtccagccg tcgccctccg ccagcgtcgc gctgcggtcg    360
tcgtcgcggg cgatccgcag cacgcgcgcg ccgggcggca gcagcgtggc gccggaccgt    420
acgcggtcga tgttcgccgc gtgcgagtac ggctgctcac ccgtggcgaa acggccgagg    480
aacagcgcgt cgacgacgtc ggacggggag tcgctgtcgt ccacgttgag ccggatcggc    540
agggcttcgt gcgggttcac ggacatgtcg ccatgatcgg gcaccggcc gccgcgtgca    600
cccgctttcc cgggcacgca cgacaggggc tttctcgccg tcttccgtcc gaacttgaac    660
gagtgtcagc catttcttgg catggacact tccagtcaac gcgcgtagct gctaccacgg    720
ttgtggcagc aatcctgcta agggaggttc catgagacgt ttccgacttg tcggcttcct    780
gagttcgctc gtcctcgccg ccggcgccg cctcaccggg gcagcgaccg cccaggcggc    840
ccaacccgcc gccgccgacg gctatgtggc cctcggcgac tcctactcct ccggggtcgg    900
agcgggcagc tacatcagct cgagcggcga ctgcaagcgc agcacgaagg cccatcccta    960
cctgtgggcg gccgcccact cgccctccac gttcgacttc accgcctgtt ccggcgcccg   1020
tacgggtgat gttctctccg gacagctcgg cccgctcagc tccggcaccg gctcgtctc    1080
gatcagcatc ggcggcaacg acgccggttt cgccgacacc atgacgacct gtgtgctcca   1140
gtccgagagc tcctgcctgt cgcggatcgc caccgccgag gcgtacgtcg actcgacgct   1200
gcccggcaag ctcgacggcg tctactcggc aatcagcgac aaggcgccga acgcccacgt   1260
cgtcgtcatc ggctacccgc gcttctacaa gctcggcacc acctgcatcg gcctgtccga   1320
gaccaagcgg acggcgatca caaggcctc cgaccacctc aacaccgtcc tcgcccagcg   1380
cgccgccgcc cacggcttca ccttcggcga cgtacgcacc accttcaccg gccacgagct   1440
gtgctccggc agcccctggc tgcacagcgt caactggctg aacatcggcg agtcgtacca   1500
ccccaccgcg gccggccagt ccggtggcta cctgccggtc ctcaacggcg ccgcctgacc   1560
tcaggcggaa ggagaagaag aaggagcgga gggagacgag gagtgggagg ccccgcccga   1620
cggggtcccc gtccccgtct ccgtctccgt cccggtcccg caagtcaccg agaacgccac   1680
cgcgtcggac gtggcccgca ccggactccg cacctccacg cgcacggcac tctcgaacgc   1740
gccggtgtcg tcgtgcgtcg tcaccaccac gccgtcctgg cgcgagcgct gccgcccga    1800
cgggaaggac agcgtccgcc accccggatc ggagaccgac ccgtccgcgg tcacccaccg   1860
gtagccgacc tccgcgggca gccgcccgac cgtgaacgtc gccgtgaacg cgggtgcccg   1920
gtcgtgcggc ggcggacagg ccccccagta gtgggtgcgc gagcccacca cggtcacctc   1980
caccgactgc gctgcggggc                                              2000
```

<210> SEQ ID NO 45
<211> LENGTH: 269
<212> TYPE: PRT
<213> ORGANISM: Streptomyces avermitilis

<400> SEQUENCE: 45

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
    50                  55                  60

```
Ser Lys Ala Tyr Pro Tyr Leu Trp Gln Ala Ala His Ser Pro Ser Ser
 65                  70                  75                  80

Phe Ser Phe Met Ala Cys Ser Gly Ala Arg Thr Gly Asp Val Leu Ala
             85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 46
<211> LENGTH: 1980
<212> TYPE: DNA
<213> ORGANISM: Streptomyces avermitilis

<400> SEQUENCE: 46
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggccct     120
tgcccttgct cgacgcggcc ttgaagccgg tgcccttctt gagcgtgacg atgtagctgc     180
ccttgatcgc ggtgggggag ccggcggcga gcaccgtgcc ctcggccggg gtggcctggg     240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacggggt ggctcaaggg      480 agttgagacc ctgtcatgag tctgacatga gcacgcaatc aacggggccg tgagcacccc     540
ggggcgaccc cggaaagtgc cgagaagtct tggcatggac acttcctgtc aacacgcgta     600
gctggtacga cggttacggc agagatcctg ctaaagggag gttccatgag acgttcccga     660
attacggcat acgtgacctc actcctcctc gccgtcggct cgccctcac cggggcagcg      720 acggcgcagg cgtccccagc cgccgcggcc acgggctatg tggccctcgg cgactcgtac     780
tcgtccggtg tcggcgccgg cagctacctc agctccagcg gcgactgcaa gcgcagttcg     840
aaggcctatc cgtacctctg gcaggccgcg cattcaccct cgtcgttcag tttcatggct     900
tgctcgggcg ctcgtacggg tgatgtcctg gccaatcagc tcggcaccct gaactcgtcc     960
accggcctgg tctccctcac catcggaggc aacgacgcgg gcttctccga cgtcatgacg    1020
```

```
acctgtgtgc tccagtccga cagcgcctgc ctctcccgca tcaacacggc gaaggcgtac   1080
gtcgactcca ccctgcccgg ccaactcgac agcgtgtaca cggcgatcag cacgaaggcc   1140
ccgtcggccc atgtggccgt gctgggctac ccccgcttct acaaactggg cggctcctgc   1200
ctcgcgggcc tctcggagac caagcggtcc gccatcaacg acgcggccga ctatctgaac   1260
agcgccatcg ccaagcgcgc cgccgaccac ggcttcacct cggcgacgt caagagcacc    1320 ttcaccggcc atgagatctg ctccagcagc acctggctgc acagtctcga cctgctgaac   1380
atcggccagt cctaccaccc gaccgcggcc ggccagtccg gcggctatct gccggtcatg   1440
aacagcgtgg cctgagctcc cacggcctga attttaagg cctgaatttt taaggcgaag    1500
gtgaaccgga agcggaggcc ccgtccgtcg gggtctccgt cgcacaggtc accgagaacg   1560
gcacggagtt ggacgtcgtg cgcaccgggt cgcgcacctc gacggcgatc tcgttcgaga   1620
tcgttccgct cgtgtcgtac gtggtgacga cacctgctt ctgctgggtc tttccgccgc    1680
tcgccgggaa ggacagcgtc ttccagcccg gatccgggac ctcgcccttc ttggtcaccc   1740
agcggtactc cacctcgacc ggcacccggc ccaccgtgaa ggtcgccgtg aacgtgggcg   1800
cctgggcggt gggcggcggg caggcaccgg agtagtcggt gtgcacgccg gtgaccgtca   1860
ccttcacgga ctgggccggc ggggtcgtcg taccgccgcc gccaccgccg cctcccggag   1920
tggagcccga gctgtggtcg cccccgccgt cggcgttgtc gtcctcgggg gttttcgaac   1980
```

<210> SEQ ID NO 47
<211> LENGTH: 372
<212> TYPE: PRT
<213> ORGANISM: Thermobifida fusca

<400> SEQUENCE: 47

```
Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln
        35                  40                  45

Asp Trp Cys Leu Gly Val Pro Val Asp Ser Arg Gly Gln Pro Ala Glu
    50                  55                  60

Asp Gly Glu Phe Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205
```

| Thr | Thr | Phe | Glu | Glu | Leu | Ile | Ser | Glu | Val | Arg | Thr | Arg | Ala | Pro | Asp |
|---|---|---|---|---|---|---|---|---|---|---|---|---|---|---|---|
| | 210 | | | | 215 | | | | | 220 | | | | | |

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
            245                 250                 255

Glu Thr Ile Gln Glu Phe Asn Gln Gln Leu Ala Glu Ala Val Ala Val
        260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
        290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
            355                 360                 365

Gly Glu Val Gly
    370

<210> SEQ ID NO 48
<211> LENGTH: 968
<212> TYPE: DNA
<213> ORGANISM: Thermobifida fusca

<400> SEQUENCE: 48

```
ctgcagacac ccgccccgcc ttctcccgga tcgtcatgtt cggcgactcc ctcagcgaca    60
ccggcaagat gtactccaag atgcgcggct acctgccgtc ctccccgccg tactacgagg   120
gccgcttctc gaacggcccg gtctggctgg agcagctgac gaagcagttc cccggcctga   180
cgatcgccaa cgaggccgag gggggcgcga ccgcagtcgc ctacaacaag atctcctgga   240
acccgaagta ccaggtcatt aacaacctcg actacgaggt cacccagttc ttgcagaagg   300
actcgttcaa gcccgacgac ctggtcatcc tgtgggtggg cgccaacgac tacctggcct   360
acggttggaa cacggagcag gacgccaagc gggtgcgcga cgccatctcg gacgcggcaa   420
accgcatggt cctgaacggc gcgaagcaga tcctgctgtt caacctgccc gacctgggcc   480
agaacccgtc cgcccgctcc cagaaggtcg tcgaggccgt ctcgcacgtg tccgcctacc   540
acaacaagct gctcctcaac ctcgcccggc agctcgcccc gacgggcatg gtcaagctgt   600
tcgagatcga caagcagttc gcggagatgc tgcgcgaccc ccagaacttc ggcctgagcg   660
acgtggagaa cccgtgctac gacggcggct acgtgtggaa gccgttcgcc acccggtccg   720
tctcgaccga ccggcagctg tcggccttct cgccccagga gcgcctggcg atcgctggca   780
acccgctcct ggcacaggcg gtagcttcgc cgatggcccg ccgctcggcc tcgcccctca   840
actgcgaggg caagatgttc tgggaccagg tccaccccac caccgtggtc cacgccgccc   900
tctcggagcg cgccgccacc ttcatcgaga cccagtacga gttcctcgcc cactagtcta   960
gaggatcc                                                            968
```

<210> SEQ ID NO 49
<211> LENGTH: 232
<212> TYPE: PRT
<213> ORGANISM: Artificial Sequence

```
<220> FEATURE:
<223> OTHER INFORMATION: structural model sequence for homology mapping

<400> SEQUENCE: 49

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
    210                 215                 220

Thr Thr Ser Phe Glu Gly Thr Cys
225                 230

<210> SEQ ID NO 50
<211> LENGTH: 184
<212> TYPE: PRT
<213> ORGANISM: Artificial Sequence
<220> FEATURE:
<223> OTHER INFORMATION: structural model sequence for homology mapping

<400> SEQUENCE: 50

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110
```

Tyr Gly Arg Arg Tyr Asn Glu Ala Phe Ser Ala Ile Tyr Pro Lys Leu
            115                 120                 125

Ala Lys Glu Phe Asp Val Pro Leu Leu Pro Phe Phe Met Glu Glu Val
130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Lys Gln Leu Gln Pro
                165                 170                 175

Leu Val Asn His Asp Ser Leu Glu
            180

<210> SEQ ID NO 51
<211> LENGTH: 225
<212> TYPE: PRT
<213> ORGANISM: Artificial Sequence
<220> FEATURE:
<223> OTHER INFORMATION: consensus sequence

<400> SEQUENCE: 51

Met Arg Arg Ser Arg Phe Leu Ala Ala Leu Ile Leu Leu Thr Leu Ala
1               5                   10                  15

Ala Leu Gly Ala Ala Ala Arg Ala Ala Pro Ala Ala Tyr Val Ala Leu
            20                  25                  30

Gly Asp Ser Tyr Ser Ser Gly Ala Gly Ser Tyr Ser Ser Gly Asp
            35                  40                  45

Cys Arg Ser Thr Lys Ala Tyr Pro Ala Leu Trp Ala Ala Ala His Ala
        50                  55                  60

Ser Ser Phe Ser Phe Ala Cys Ser Gly Ala Arg Thr Tyr Asp Val Leu
65                  70                  75                  80

Ala Gln Leu Leu Asn Ser Thr Leu Val Ser Ile Thr Ile Gly Gly Asn
                85                  90                  95

Asp Ala Gly Phe Ala Asp Met Thr Thr Cys Val Leu Ser Asp Ser Ala
            100                 105                 110

Cys Leu Arg Ile Ala Ala Lys Tyr Ile Thr Leu Pro Ala Arg Leu Asp
            115                 120                 125

Ser Val Tyr Ser Ala Ile Thr Arg Ala Pro Ala Arg Val Val Val Leu
        130                 135                 140

Gly Tyr Pro Arg Ile Tyr Ser Gly Leu Gly Leu Ser Thr Lys Arg Ala
145                 150                 155                 160

Ala Ile Asn Asp Ala Ala Asp Leu Asn Ser Val Ile Ala Lys Arg Ala
                165                 170                 175

Ala Asp His Gly Phe Thr Phe Gly Asp Val Thr Phe Gly His Glu Leu
            180                 185                 190

Cys Ser Ala Pro Trp Leu His Ser Leu Thr Leu Pro Val Ser Tyr His
            195                 200                 205

Pro Thr Ala Gly His Ala Ala Gly Tyr Leu Pro Val Leu Asn Ser Ile
        210                 215                 220

Thr
225

<210> SEQ ID NO 52
<211> LENGTH: 4
<212> TYPE: PRT
<213> ORGANISM: Artificial Sequence
<220> FEATURE:
<223> OTHER INFORMATION: sequence motif
<220> FEATURE:
<221> NAME/KEY: SITE

```
-continued

<222> LOCATION: (4)..(4)
<223> OTHER INFORMATION: Leu, Ala, Val, Ile, Phe, Tyr, His, Gln, Thr,
      Asn, Met or Ser

<400> SEQUENCE: 52

Gly Asp Ser Xaa
1

<210> SEQ ID NO 53
<211> LENGTH: 5
<212> TYPE: PRT
<213> ORGANISM: Artificial Sequence
<220> FEATURE:
<223> OTHER INFORMATION: sequence motif
<220> FEATURE:
<221> NAME/KEY: SITE
<222> LOCATION: (2)..(2)
<223> OTHER INFORMATION: Ala or Gly.
<220> FEATURE:
<221> NAME/KEY: SITE
<222> LOCATION: (5)..(5)
<223> OTHER INFORMATION: Tyr, Ala or Leu.

<400> SEQUENCE: 53

Gly Ala Asn Asp Tyr
1               5
```

The invention claimed is:

1. A process of enzymatic degumming an edible oil, comprising treating the edible oil with a lipid acyltransferase, wherein the lipid acyltransferase:
   (a) transfers an acyl group from a phospholipid to one or more acyl acceptors selected from sterol and stanol to form an ester;
   (b) comprises an amino acid sequence motif GDSX, wherein X is an amino acid residue selected from L, A, V, I, F, Y, H, Q, T, N, M and S;
   (c) when aligned to either SEQ ID NO: 2 or SEQ ID NO: 37 has a GANDY block; and
   (d) has at least 5% acyltransferase activity when reacted with a substrate, wherein the substrate is soya bean oil supplemented with 1% plant sterol and 2% phosphatidylcholine, wherein:
      (i) the substrate to which no enzyme has been added is a control;
      (ii) in an enzymatic reaction with the substrate, lipid material from the reaction and the control are analyzed; and
      (iii) acyltransferase activity is calculated as a percentage of total enzymatic activity using the formula:

$(\Delta \times 100)/((\Delta + \Delta \% \text{ fatty acid})/\text{Mv fatty acid})$, wherein:
      $\Delta$ % fatty acid=% fatty acid(enzyme)−% fatty acid (control);
      Mv fatty acid=average molecular weight of the fatty acids; and
      $\Delta = \Delta$ % sterol ester/Mv sterol ester,
         wherein:
         $\Delta$ % sterol ester=% sterol/stanol ester(enzyme)−% sterol/stanol ester(control); and
         Mv sterol ester=average molecular weight of the sterol/stanol esters.

2. A process according to claim 1, wherein a sterol ester, a stanol ester, or both a sterol ester and a stanol ester is formed.

3. A process according to claim 1, wherein the acyl acceptor is a sterol.

4. A process according to claim 1, wherein the phospholipid is a lecithin.

5. A process according to claim 1, wherein the lipid acyltransferase transfers the acyl group from a lipid to one or more acyl acceptors selected from a carbohydrate, a protein, a protein subunit, and glycerol.

6. A process according to claim 1, wherein the lipid acyltransferase is a natural lipid acyltransferase.

7. A process according to claim 1, wherein the lipid acyltransferase is a variant lipid acyltransferase.

8. A process according to claim 1 wherein, the lipid acyltransferase is obtained from an organism selected from: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

9. A process according to claim 1, wherein the lipid acyltransferase is obtained from an organism selected from: *Aeromonas hydrophila, Aeromonas salmonicida, Striptomyces coelicolor, Streptomyces rimosus, Streptomyces thermosacchari, Streptomyces avermitilis, Mycobacterium, Streptococcus pyogenes, Lactococcus lactis, Streptococcus pyogenes, Streptococcus thermophilus, Lactobacillus helveticus, Desulfitobacterium dehalogenans, Bacillus* sp, *Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis, Thermobifida fusca* and *Corynebacterium efficiens*.

10. A process according to claim 1, wherein the X of the GDSX motif is L.

11. A process according to claim 1, wherein the lipid acyltransferase is selected from: SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, or SEQ ID No. 15, SEQ ID No. 16, SEQ ID No. 17, SEQ ID No. 18, SEQ ID No. 36, SEQ ID No. 38, SEQ ID No. 40, SEQ ID No. 41, SEQ ID No 45, SEQ ID No. 47, SEQ ID No. 50, and an amino acid sequence which has 95% or more identity thereto.

12. A process according to claim 1 wherein the lipid acyltransferase has the amino acid sequence shown as SEQ ID No. 16, or an amino acid sequence which has 95% or more homology thereto.

13. A process according to claim 12, wherein the lipid acyltransferase has the amino acid sequence shown as SEQ ID No. 16.

14. A process according to claim 7, wherein the variant lipid acyltransferase comprises the amino acid sequence motif GDSX, wherein:

X is an amino acid residue selected from L, A, V, I, F, Y, H, Q, T, N, M and S; and the variant lipid acyltransferase comprises one or more amino acid modifications compared with a parent sequence at any one or more of the amino acid residues defined in set 2 or set 4 or set 6 or set 7.

15. A process according to claim 7, wherein the variant lipid acyltransferase has the amino acid sequence shown as SEQ ID No. 16, or an amino acid sequence with 95% or more homology thereto.

16. A process according to claim 15, wherein the variant lipid acyltransferase has the amino acid sequence shown as SEQ ID No. 16.

17. A process according to claim 1, wherein there is less than 1% water in the edible oil.

18. A process according to claim 17, wherein there is less than 0.5% water in the edible oil.

19. A process according to claim 18, wherein there is less than 0.1% water in the edible oil.

20. A process according to claim 1, further comprising removing by filtration the lysophospholipids produced by action of the lipid acyltransferase.

\* \* \* \* \*